US012571016B2

(12) United States Patent
Yu et al.

(10) Patent No.: US 12,571,016 B2
(45) Date of Patent: *Mar. 10, 2026

(54) METHODS AND COMPOSITIONS FOR NUCLEIC ACID AMPLIFICATION

(71) Applicant: LIFE TECHNOLOGIES CORPORATION, Carlsbad, CA (US)

(72) Inventors: Hua Yu, Durham, NC (US); Theo Nikiforov, Carlsbad, CA (US); Abraham Rosenbaum, Passaic, NJ (US)

(73) Assignee: Life Technologies Corporation, Carlsbad, CA (US)

( * ) Notice: Subject to any disclaimer, the term of this patent is extended or adjusted under 35 U.S.C. 154(b) by 1039 days.

This patent is subject to a terminal disclaimer.

(21) Appl. No.: 17/667,334

(22) Filed: Feb. 8, 2022

(65) Prior Publication Data

US 2022/0162660 A1    May 26, 2022

Related U.S. Application Data

(63) Continuation of application No. 16/308,803, filed as application No. PCT/US2017/036842 on Jun. 9, 2017, now Pat. No. 11,268,117.

(60) Provisional application No. 62/348,402, filed on Jun. 10, 2016.

(51) Int. Cl.
| | |
|---|---|
| *C12P 19/34* | (2006.01) |
| *C12Q 1/6844* | (2018.01) |
| *C12Q 1/6853* | (2018.01) |

(52) U.S. Cl.
CPC ............ *C12P 19/34* (2013.01); *C12Q 1/6844* (2013.01); *C12Q 1/6853* (2013.01)

(58) Field of Classification Search
CPC ..... C12P 19/34; C12Q 1/6844; C12Q 1/6853; C12Q 2521/101; C12Q 2521/327; C12Q 2521/507; C12Q 2525/121; C12Q 2525/186; C12Q 2521/301
See application file for complete search history.

(56) References Cited

U.S. PATENT DOCUMENTS

| | | | |
|---|---|---|---|
| 5,223,414 | A | 6/1993 | Zarling et al. |
| 5,273,881 | A | 12/1993 | Sena et al. |
| 5,670,316 | A | 9/1997 | Sena et al. |
| 7,270,981 | B2 | 9/2007 | Armes et al. |
| 7,323,305 | B2 | 1/2008 | Leamon et al. |
| 7,399,590 | B2 | 7/2008 | Piepenburg et al. |
| 7,435,561 | B2 | 10/2008 | Piepenburg et al. |
| 7,601,499 | B2 | 10/2009 | Berka et al. |
| 7,622,280 | B2 | 11/2009 | Holliger et al. |
| 7,666,598 | B2 | 2/2010 | Piepenburg et al. |
| 7,763,427 | B2 | 7/2010 | Piepenburg et al. |
| 7,948,015 | B2 | 5/2011 | Rothberg et al. |
| 8,017,339 | B2 | 9/2011 | Piepenburg et al. |
| 8,030,000 | B2 | 10/2011 | Piepenburg et al. |
| 8,062,850 | B2 | 11/2011 | Piepenburg et al. |
| 8,071,308 | B2 | 12/2011 | Piepenburg et al. |
| 8,911,948 | B2 | 12/2014 | Walder et al. |
| 8,936,921 | B2 | 1/2015 | Hicke et al. |
| 2008/0009420 | A1 | 1/2008 | Schroth et al. |
| 2008/0166727 | A1 | 7/2008 | Esfandyarpour et al. |
| 2009/0026082 | A1 | 1/2009 | Rothberg et al. |
| 2010/0311127 | A1 | 12/2010 | Piepenburg et al. |
| 2011/0123991 | A1* | 5/2011 | Houser et al. |
| 2011/0262903 | A1 | 10/2011 | Davidson et al. |
| 2011/0294674 | A1 | 12/2011 | Cheung et al. |
| 2014/0329245 | A1 | 11/2014 | Spier et al. |
| 2015/0344938 | A1 | 12/2015 | Bramlett et al. |
| 2016/0040219 | A1 | 2/2016 | Johnson et al. |
| 2017/0218438 | A1 | 8/2017 | Dobosy et al. |

FOREIGN PATENT DOCUMENTS

| | | |
|---|---|---|
| WO | WO-03072805 A2 | 9/2003 |
| WO | WO-2009135093 A2 | 11/2009 |
| WO | WO-2009150467 A1 | 12/2009 |
| WO | WO-2011060014 A1 | 5/2011 |
| WO | WO-2012083189 A2 | 6/2012 |
| WO | WO-2012135053 A2 | 10/2012 |
| WO | WO-2013023176 A2 | 2/2013 |
| WO | WO-2013123238 A1 | 8/2013 |
| WO | WO-2013142364 A1 | 9/2013 |

(Continued)

OTHER PUBLICATIONS

Anderson E.P., et al., "A System For Multiplexed Direct Electrical Detection Of DNA Synthesis," Sensors and actuators. B, Chemical, Jan. 2008, vol. 129, No. 1, pp. 79-86.
Dobosy J.R et al., "RNase H-Dependent PCR (rhPCR): Improved Specificity and Single Nucleotide Polymorphism Detection Using Blocked Cleavable Primers", BMC Biotechnology, 2011, vol. 11, No. 80, pp. 1-18, URL: https://doi.org/10.1186/1472-6750-11-80.
Dobosy J.R et al., "RNase H-Dependent PCR (rhPCR): Improved Specificity and Single Nucleotide Polymorphism Detection Using Blocked Cleavable Primers (Supplementary Material)", BMC Biotechnology, 2011, vol. 11, No. 80, pp. 1-13, URL: https://doi.org/10.1186/1472-6750-11-80.

(Continued)

*Primary Examiner* — Cynthia B Wilder

(57) ABSTRACT

Methods as well as related compositions and kits for recombinase-mediated nucleic acid amplification, such as recombinase-polymerase amplification (RPA), of a nucleic acid template using at least one blocked primer that contains a 5' domain, at least one nucleotide that is cleavable by an RNase H enzyme, a 3' domain, wherein the primer is not extendable by a polymerase, and wherein the 3' domain has a length of 7-100 nucleotides, for example 10-30 nucleotides. These methods and the use of a blocked primer reduce or eliminate non-specific amplification products, such as primer dimers, which are generated in RPA reactions.

21 Claims, 18 Drawing Sheets

Specification includes a Sequence Listing.

(56) References Cited

FOREIGN PATENT DOCUMENTS

| WO | WO-2014110528 | A1 | 7/2014 |
| WO | WO-2015195949 | A2 | 12/2015 |

OTHER PUBLICATIONS

EP17811116.7, Extended Search Report, Feb. 4, 2020, 14 pages.
Hoser, M.J., et al. (2014) PLoS ONE 9(11): e112656. doi:10.1371/journal.pone.0112656 "Strand Invasion Based Amplification (SIBA): A Novel Isothermal DNA Amplification Technology Demonstrating High Specificity and Sensitivity for a Single Molecule of Target Analyte", Supplemental Information.
International Preliminary Report on Patentability for International Application No. PCT/US2017/036842 mailed Dec. 11, 2018, 25 pages.
International Search Report and Written Opinion for Application No. PCT/US2017/036842, mailed Aug. 29, 2017, 28 pages.
Kanaya et al., "Expression, Purification, and Characterization of a Recombinant Ribonuclease H from Thermus thermophilus HB8,"
The Journal of Biological Chemistry, May 15, 1992 (May 15, 1992), vol. 267, pp. 10184-10192.
Piepenburg O., et al., "DNA Detection Using Recombination Proteins," PLoS Biology, Jul. 1, 2006, vol. 4, No. 7, pp. 1115-1121, XP002501560.
Pourmand N., et aL, "Direct Electrical Detection of DNA Synthesis," Proceedings of the National Academy of Sciences, Apr. 25, 2006, vol. 103, No. 17, pp. 6466-6470.
Purushothaman S., et aL, "Towards Fast Solid State DNA Sequencing," IEEE ISCAS Proceedings, Circuits and Systems, 2002, vol. 4, pp. IV-169-IV-172.
Sakata T., et al., "DNA Sequencing Based on Intrinsic Molecular Charges," Angewandte Chemie International, 2006, vol. 118, pp. 2283-2286.
Sakurai T., et al., "Real-Time Monitoring of DNA Polymerase Reactions by a Micro ISFET pH Sensor," Analytical Chemistry, Sep. 1992, vol. 64, No. 17, pp. 1996-1997.
Simsek, M. et al., "Effect of Single Mismatches at 3'-end of Primers on Polymerase Chain Reaction", Journal for Scientific Research Medical Sciences, vol. 2, No. 1, Jan. 2000, pp. 11-14, ISSN: 1029-4066.

* cited by examiner

| Lane | Primer configuration |
|---|---|
| M | NEB Low MW ladder |
| 1 | Regular short (20mer) primers |
| 2 | Regular long (46-53mer) primers |
| 3 | Blocked primers V1-rC |
| 4 | Blocked primers V2-rC |
| 5 | Blocked primers V2-MM-rC |
| 6 | Blocked primers V2-rU |
| 7 | Blocked primers V3 |

Figure 4
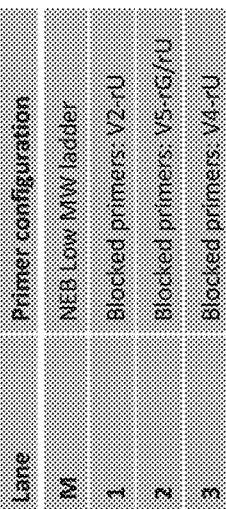
| Lane | Primer configuration |
|------|---------------------|
| M | NEB Low MW ladder |
| 1 | Blocked primers V2-rU |
| 2 | Blocked primers V5-rG/rU |
| 3 | Blocked primers V4-rU |
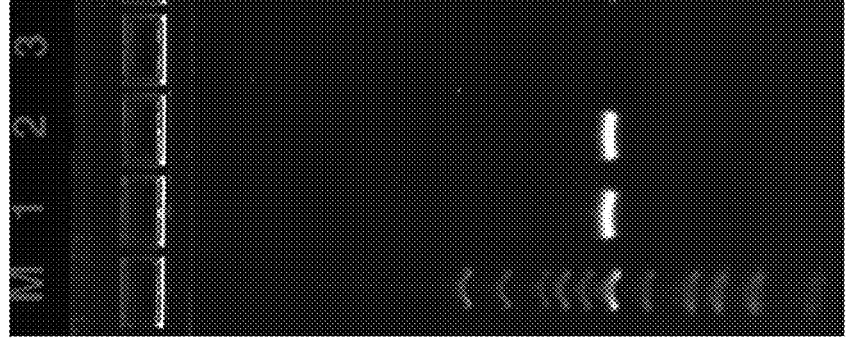

| Lane | Primer configuration |
|---|---|
| M | NEB Low MW ladder |
| 1 | Blocked primers: V2-rU |
| 2 | Blocked primers: V5 -G/rU |
| 3 | Blocked primers: V4-rU |

Figure 6
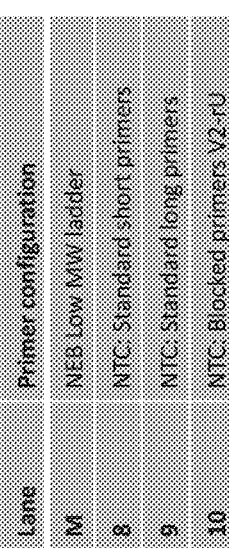
| Lane | Primer configuration |
|---|---|
| M | NEB Low MW ladder |
| 8 | NTC: Standard short primers |
| 9 | NTC: Standard long primers |
| 10 | NTC: Blocked primers V2-rU |
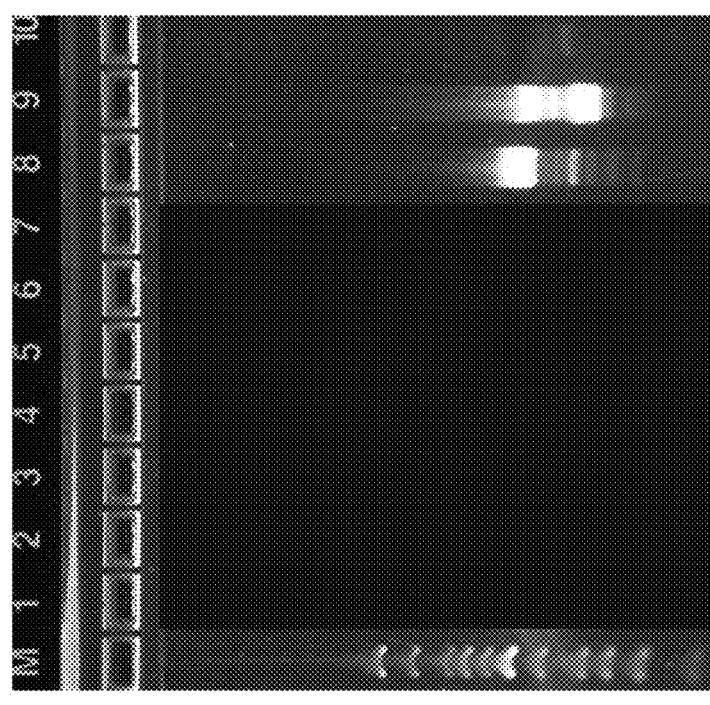

| Lane | Primer & Exp. configuration |
|------|------------------------------|
| M | NEB low molecular weight ladder |
| 1 | Standard primers; 5 μL loaded |
| 2 | Blocked primers; with RNaseH enzyme; 5 μL loaded |
| 3 | Blocked primer; No RNaseH enzyme control; 5 μL loaded |
| 4 | Standard primers; 15 μL loaded |
| 5 | Blocked primers; with RNaseH enzyme; 15 μL loaded |
| 6 | Blocked primers; No RNaseH enzyme control; 15 μL loaded |

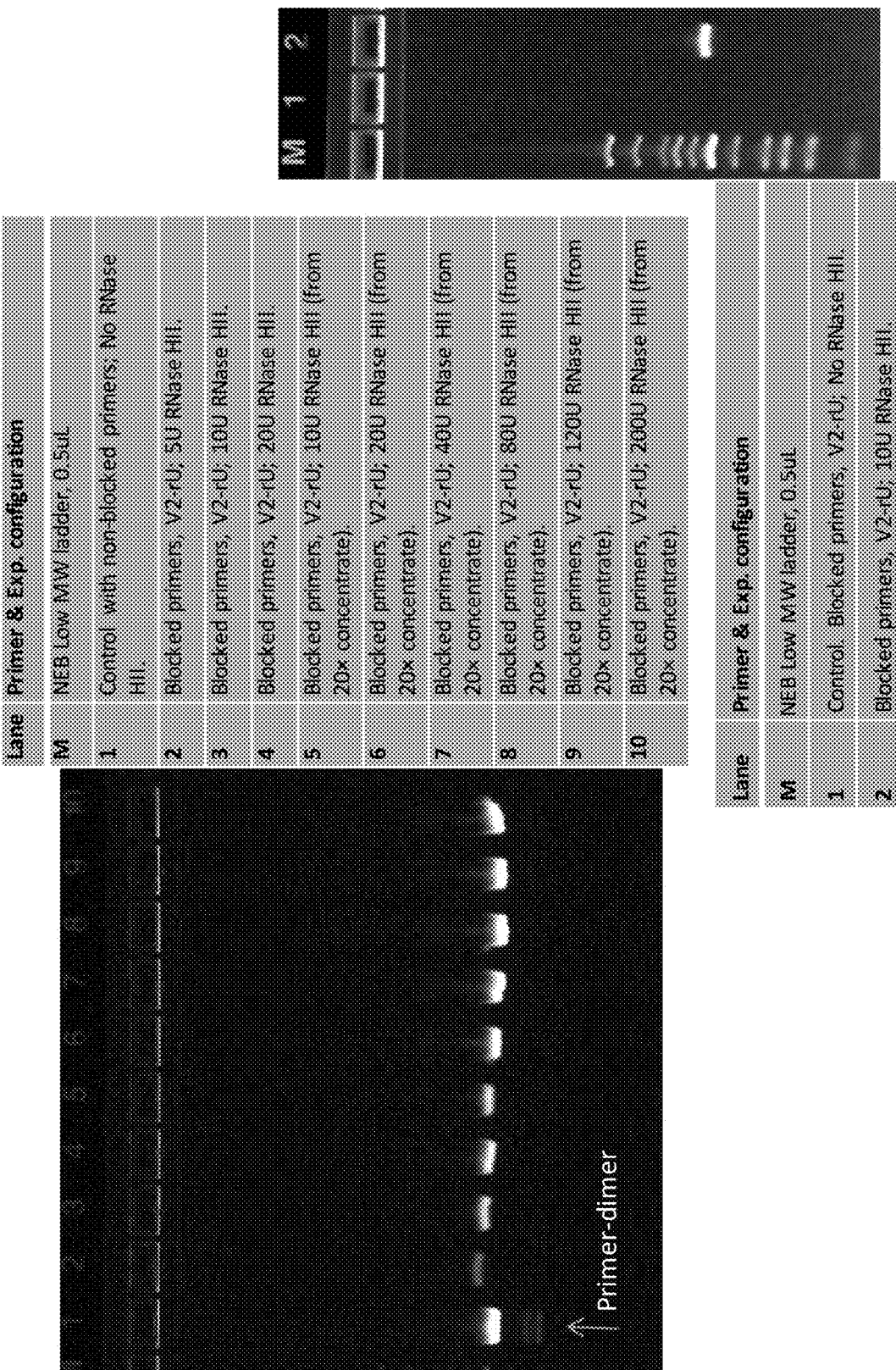

Figure 8A

| Lane | Primer & Exp. configuration |
|---|---|
| M | NEB Low MW ladder, 0.5uL |
| 1 | Control with non-blocked primers; No RNase HII. |
| 2 | Blocked primers, V2-rU, 5U RNase HII. |
| 3 | Blocked primers, V2-rU, 10U RNase HII. |
| 4 | Blocked primers, V2-rU, 20U RNase HII. |
| 5 | Blocked primers, V2-rU, 10U RNase HII (from 20x concentrate). |
| 6 | Blocked primers, V2-rU, 20U RNase HII (from 20x concentrate). |
| 7 | Blocked primers, V2-rU, 40U RNase HII (from 20x concentrate). |
| 8 | Blocked primers, V2-rU, 80U RNase HII (from 20x concentrate). |
| 9 | Blocked primers, V2-rU, 120U RNase HII (from 20x concentrate). |
| 10 | Blocked primers, V2-rU, 200U RNase HII (from 20x concentrate). |

| Lane | Primer & Exp. configuration |
|---|---|
| M | NEB Low MW ladder, 0.5uL |
| 1 | Control, Blocked primers, No RNase HII |
| 2 | Blocked primers, V2-rU, 10U RNase HII. |

Primer-dimer

Figure 8B

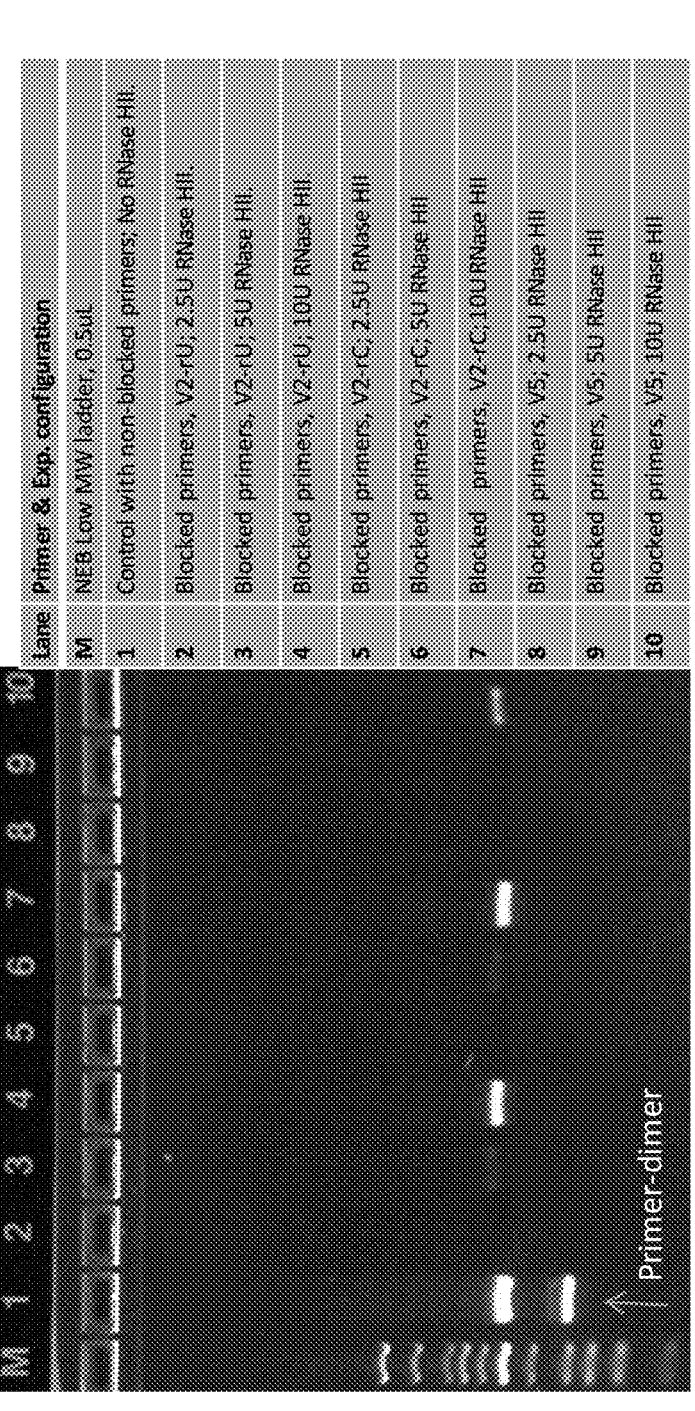

| Lane | Primer & Exp. configuration |
|---|---|
| M | NEB Low MW ladder, 0.5uL |
| 1 | Control with non-blocked primers, No RNase HII |
| 2 | Blocked primers, V2-rU, 2.5U RNase HII |
| 3 | Blocked primers, V2-rU, 5U RNase HII |
| 4 | Blocked primers, V2-rU, 10U RNase HII |
| 5 | Blocked primers, V2-rC, 2.5U RNase HII |
| 6 | Blocked primers, V2-rC, 5U RNase HII |
| 7 | Blocked primers, V2-rC, 10U RNase HII |
| 8 | Blocked primers, V5, 2.5U RNase HII |
| 9 | Blocked primers, V5, 5U RNase HII |
| 10 | Blocked primers, V5, 10U RNase HII |

| Lane | Primer & Exp. configuration |
| --- | --- |
| M | NEB Low MW ladder, 0.5uL |
| 1 | Control no RNase HII, Blocked primers, V2-rU, Incubation at 37C. |
| 2 | Blocked primers, V2-rU, 10U RNase HII, Incubation at 37C. |
| 3 | Blocked primers, V2-rU, 10U RNase HII, Incubation at 40C. |
| 4 | Blocked primers, V2-rU, 10U RNase HII, Incubation at 42C. |

Figure 9

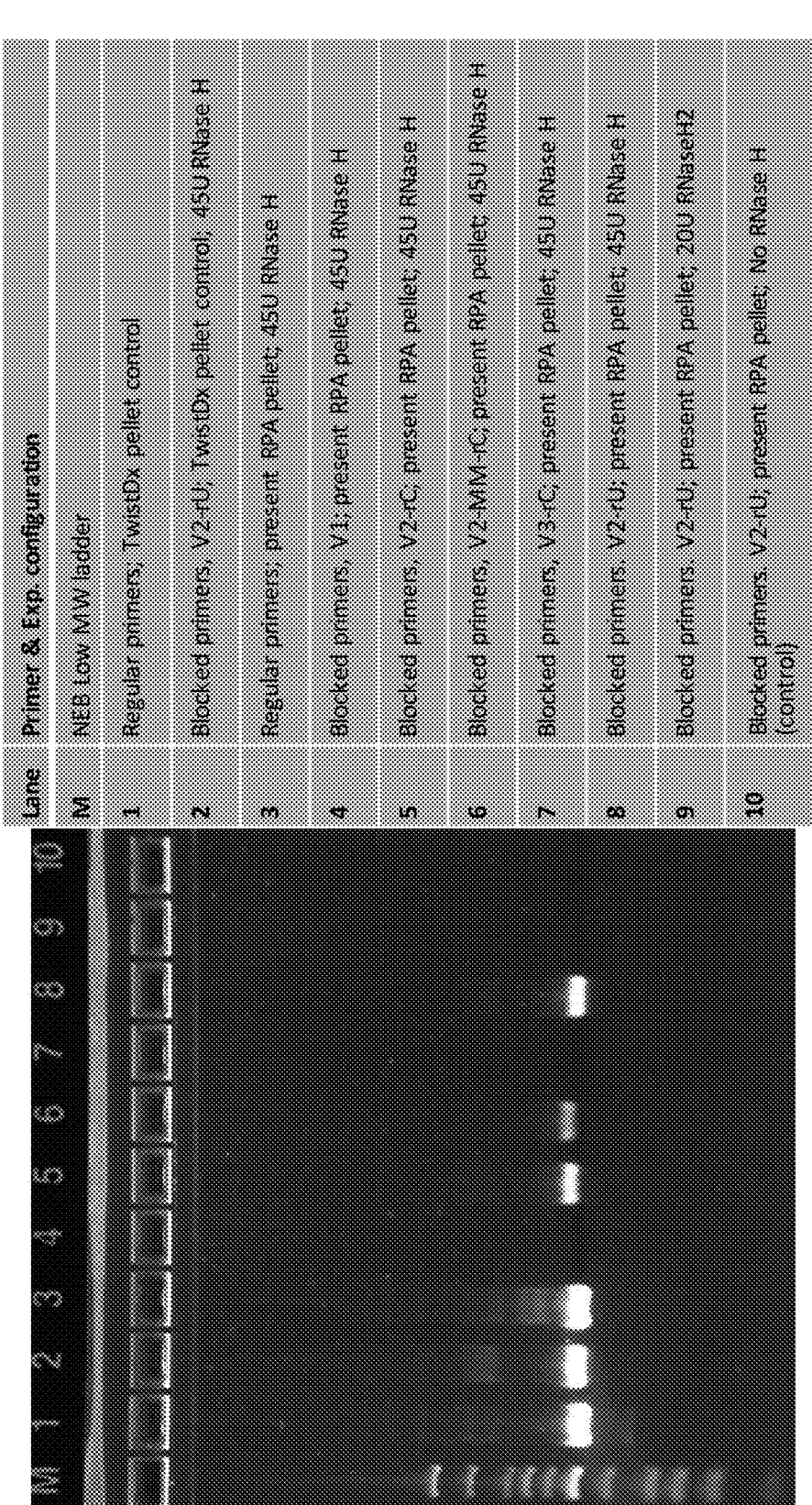

| Lane | Primer & Exp. configuration |
|---|---|
| M | NEB Low MW ladder |
| 1 | Regular primers; TwistDx pellet control |
| 2 | Blocked primers; V2-rU; TwistDx pellet control; 45U RNase H |
| 3 | Regular primers; present RPA pellet; 45U RNase H |
| 4 | Blocked primers; V1; present RPA pellet; 45U RNase H |
| 5 | Blocked primers; V2-rC; present RPA pellet; 45U RNase H |
| 6 | Blocked primers; V2-MM-rC; present RPA pellet; 45U RNase H |
| 7 | Blocked primers; V3-rC; present RPA pellet; 45U RNase H |
| 8 | Blocked primers; V2-rU; present RPA pellet; 45U RNase H |
| 9 | Blocked primers; V2-rU; present RPA pellet; 20U RNaseH2 |
| 10 | Blocked primers; V2-rU; present RPA pellet; No RNase H (control) |

Figure 10

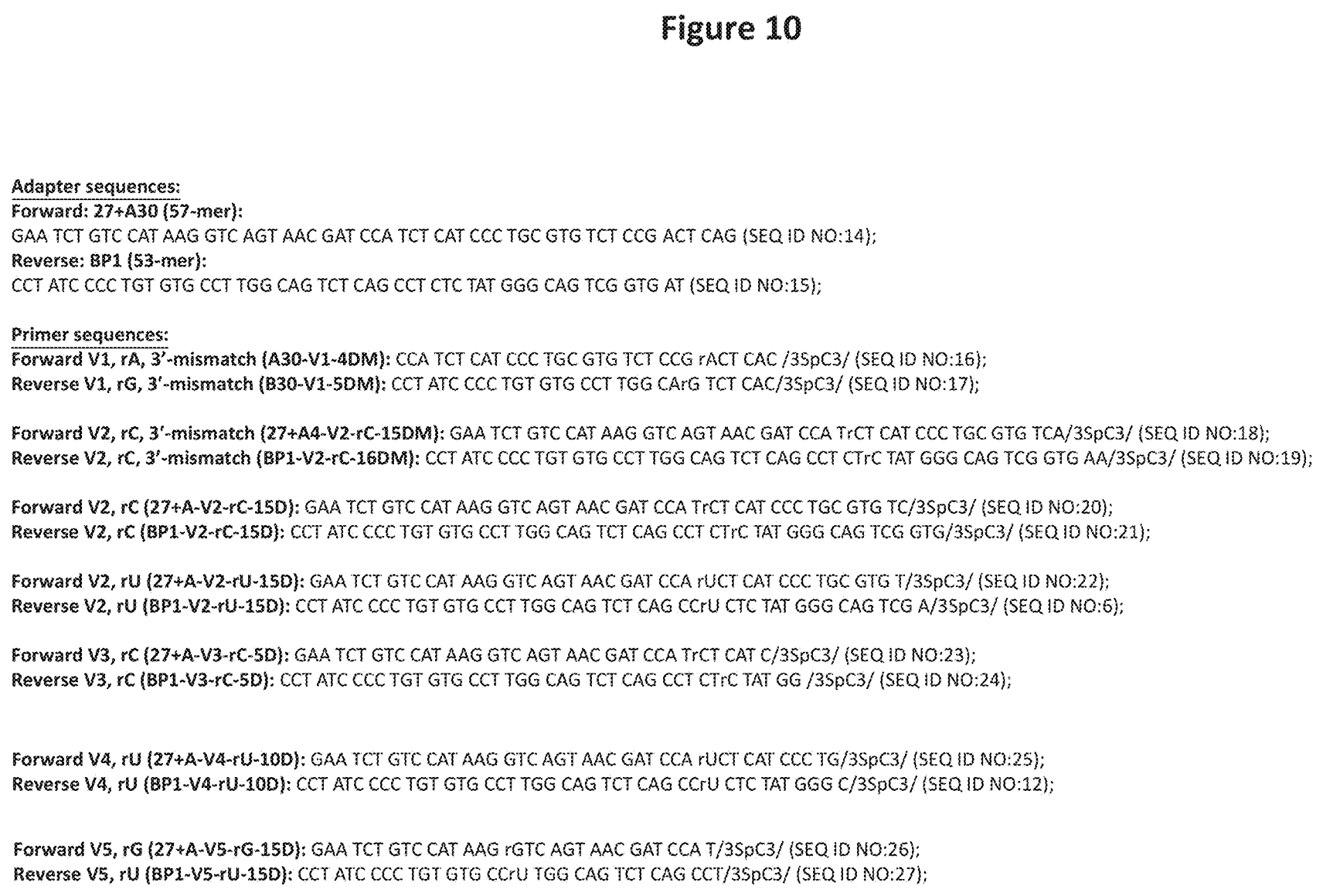

Adapter sequences:
Forward: 27+A30 (57-mer):
GAA TCT GTC CAT AAG GTC AGT AAC GAT CCA TCT CAT CCC TGC GTG TCT CCG ACT CAG (SEQ ID NO:14);
Reverse: BP1 (53-mer):
CCT ATC CCC TGT GTG CCT TGG CAG TCT CAG CCT CTC TAT GGG CAG TCG GTG AT (SEQ ID NO:15);

Primer sequences:
Forward V1, rA, 3'-mismatch (A30-V1-4DM): CCA TCT CAT CCC TGC GTG TCT CCG rACT CAC /3SpC3/ (SEQ ID NO:16);
Reverse V1, rG, 3'-mismatch (B30-V1-5DM): CCT ATC CCC TGT GTG CCT TGG CArG TCT CAC/3SpC3/ (SEQ ID NO:17);

Forward V2, rC, 3'-mismatch (27+A4-V2-rC-15DM): GAA TCT GTC CAT AAG GTC AGT AAC GAT CCA TrCT CAT CCC TGC GTG TCA/3SpC3/ (SEQ ID NO:18);
Reverse V2, rC, 3'-mismatch (BP1-V2-rC-16DM): CCT ATC CCC TGT GTG CCT TGG CAG TCT CAG CCT CTrC TAT GGG CAG TCG GTG AA/3SpC3/ (SEQ ID NO:19);

Forward V2, rC (27+A-V2-rC-15D): GAA TCT GTC CAT AAG GTC AGT AAC GAT CCA TrCT CAT CCC TGC GTG TC/3SpC3/ (SEQ ID NO:20);
Reverse V2, rC (BP1-V2-rC-15D): CCT ATC CCC TGT GTG CCT TGG CAG TCT CAG CCT CTrC TAT GGG CAG TCG GTG/3SpC3/ (SEQ ID NO:21);

Forward V2, rU (27+A-V2-rU-15D): GAA TCT GTC CAT AAG GTC AGT AAC GAT CCA rUCT CAT CCC TGC GTG T/3SpC3/ (SEQ ID NO:22);
Reverse V2, rU (BP1-V2-rU-15D): CCT ATC CCC TGT GTG CCT TGG CAG TCT CAG CCrU CTC TAT GGG CAG TCG A/3SpC3/ (SEQ ID NO:6);

Forward V3, rC (27+A-V3-rC-5D): GAA TCT GTC CAT AAG GTC AGT AAC GAT CCA TrCT CAT C/3SpC3/ (SEQ ID NO:23);
Reverse V3, rC (BP1-V3-rC-5D): CCT ATC CCC TGT GTG CCT TGG CAG TCT CAG CCT CTrC TAT GG /3SpC3/ (SEQ ID NO:24);

Forward V4, rU (27+A-V4-rU-10D): GAA TCT GTC CAT AAG GTC AGT AAC GAT CCA rUCT CAT CCC TG/3SpC3/ (SEQ ID NO:25);
Reverse V4, rU (BP1-V4-rU-10D): CCT ATC CCC TGT GTG CCT TGG CAG TCT CAG CCrU CTC TAT GGG C/3SpC3/ (SEQ ID NO:12);

Forward V5, rG (27+A-V5-rG-15D): GAA TCT GTC CAT AAG rGTC AGT AAC GAT CCA T/3SpC3/ (SEQ ID NO:26);
Reverse V5, rU (BP1-V5-rU-15D): CCT ATC CCC TGT GTG CCrU TGG CAG TCT CAG CCT/3SpC3/ (SEQ ID NO:27);

Figure 11

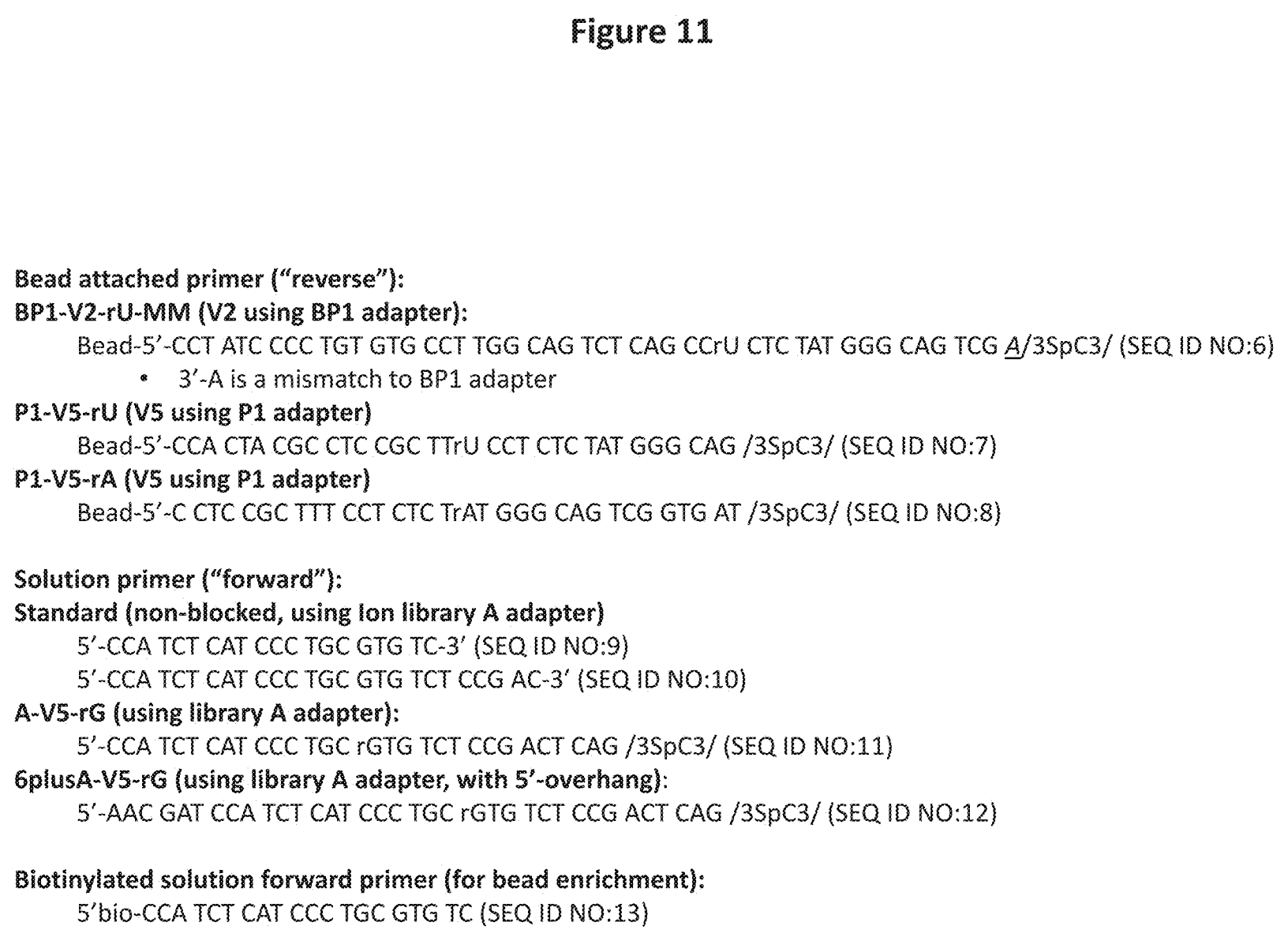

Bead attached primer ("reverse"):

BP1-V2-rU-MM (V2 using BP1 adapter):

Bead-5'-CCT ATC CCT TGT GTG CCT TGG CAG TCT CAG CCrU CTC TAT GGG CAG TCG A/3SpC3/ (SEQ ID NO:6)

• 3'-A is a mismatch to BP1 adapter

P1-V5-rU (V5 using P1 adapter)

Bead-5'-CCA CTA CGC CTC CGC TTrU CCT CTC TAT GGG CAG /3SpC3/ (SEQ ID NO:7)

P1-V5-rA (V5 using P1 adapter)

Bead-5'-C CTC CGC TTT CCT CTC TrAT GGG CAG TCG GTG AT /3SpC3/ (SEQ ID NO:8)

Solution primer ("forward"):

Standard (non-blocked, using Ion library A adapter)

5'-CCA TCT CAT CCC TGC GTG TC-3' (SEQ ID NO:9)

5'-CCA TCT CAT CCC TGC GTG TCT CCG AC-3' (SEQ ID NO:10)

A-V5-rG (using library A adapter):

5'-CCA TCT CAT CCC TGC rGTG TCT CCG ACT CAG /3SpC3/ (SEQ ID NO:11)

6plusA-V5-rG (using library A adapter, with 5'-overhang):

5'-AAC GAT CCA TCT CAT CCC TGC rGTG TCT CCG ACT CAG /3SpC3/ (SEQ ID NO:12)

Biotinylated solution forward primer (for bead enrichment):

5'bio-CCA TCT CAT CCC TGC GTG TC (SEQ ID NO:13)

Figure 12A

| Sample | Barcode | RNase H used | Reaction volume | Reaction time |
|---|---|---|---|---|
| 1 | IonXpress_055 | 2 µL | 300 µL | 40 min |
| 2 | IonXpress_056 | 4 µL | 300 µL | 40 min |
| 3 | IonXpress_057 | 2 µL | 300 µL | 60 min |
| 4 | IonXpress_058 | 4 µL | 300 µL | 60 min |

Figure 12B

| Library barcode Name | Sample | Bases | >=Q20 Bases | Reads | Mean Read Length with Ion quality trimming |
|---|---|---|---|---|---|
| No barcode | None | 47,429,386 | 24,749,762 | 832,036 | 57 bp |
| IonXpress_055 | Sample 1 | 39,545,473 | 26,090,942 | 541,554 | 73 bp |
| IonXpress_056 | Sample 2 | 177,244,735 | 119,598,023 | 2,356,364 | 75 bp |
| IonXpress_057 | Sample 3 | 27,505,867 | 18,323,107 | 367,846 | 75 bp |
| IonXpress_058 | Sample 4 | 192,246,272 | 128,539,252 | 2,579,667 | 75 bp |

Figure 13
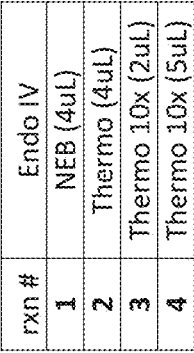
| rxn # | Endo IV |
|-------|---------|
| 1 | NEB (4uL) |
| 2 | Thermo (4uL) |
| 3 | Thermo 10x (2uL) |
| 4 | Thermo 10x (5uL) |
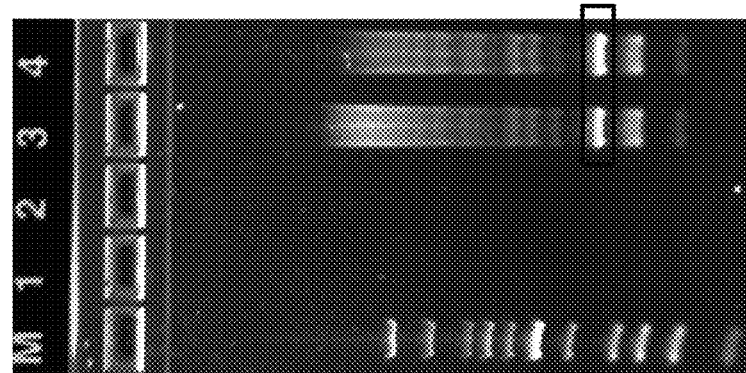

Figure 14

| Lane | Primer & Exp. configuration |
|---|---|
| M | NEB Low MW ladder |
| 1 | Blocked ribo primers (V2-rC-MM; 100 nM) each RNase H2 4 µL (20J) |
| 2 | Blocked ribo primers V2-rC-MM; 200 nM each RNase H2 4 µL (22J) |
| 3 | Blocked ribo primers V2-rC-MM; 400 nM each RNase H2 4 µL (20J) |
| 4 | Blocked ribo primers V2-rC-MM; 800 nM each RNase H2 4 µL (20J) |
| 5 | Blocked ribo primers V2-rC-MM; 100 nM each 9x RNase H2 1 µL (45J) |
| 6 | Blocked ribo primers V2-rC-MM; 200 nM each 9x RNase H2 1 µL (45J) |
| 7 | Blocked ribo primers V2-rC-MM; 400 nM each 9x RNase H2 1 µL (45J) |
| 8 | Blocked ribo primers V2-rC-MM; 800 nM each 9x RNase H2 1 µL (45J) |
| 9 | Blocked AP primers; 100 nM, APE1 4 µL (40J) |
| 10 | Blocked AP primers; 400 nM, APE1 4 µL (40J) |

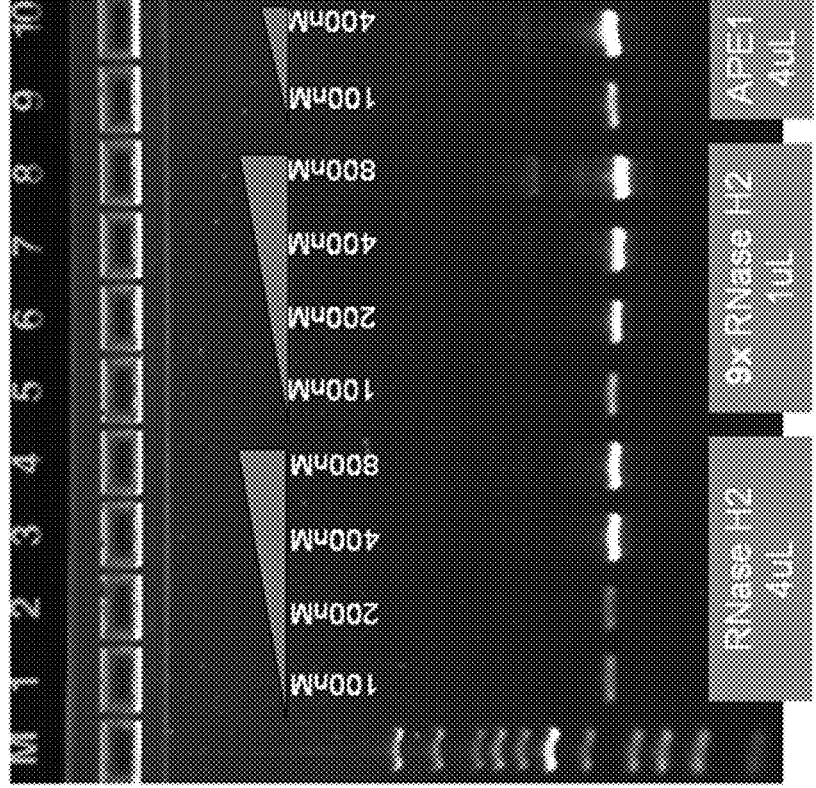

Figure 15
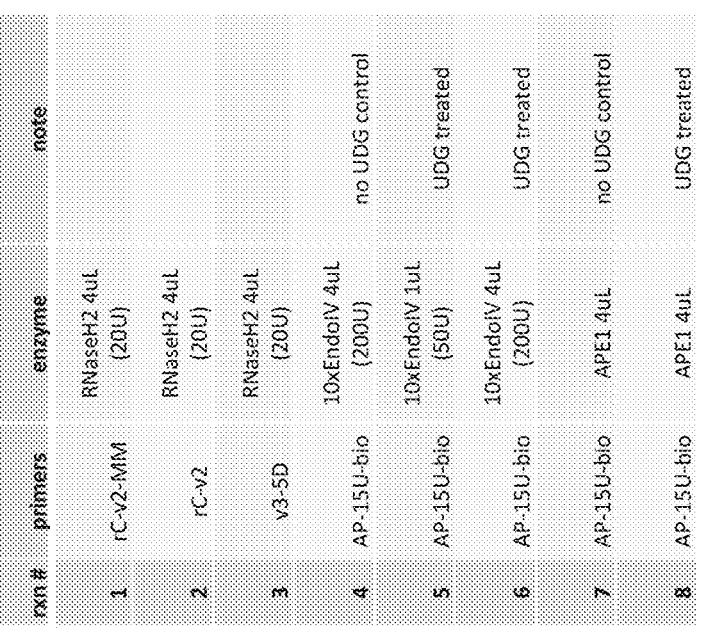
| rxn # | primers | enzyme | note |
|---|---|---|---|
| 1 | rC-v2-MM | RNaseH2 4uL (20U) | |
| 2 | rC-v2 | RNaseH2 4uL (20U) | |
| 3 | v3-5D | RNaseH2 4uL (20U) | |
| 4 | AP-15U-bio | 10xEndoIV 4uL (200U) | no UDG control |
| 5 | AP-15U-bio | 10xEndoIV 1uL (50U) | UDG treated |
| 6 | AP-15U-bio | 10xEndoIV 4uL (200U) | UDG treated |
| 7 | AP-15U-bio | APE1 4uL | no UDG control |
| 8 | AP-15U-bio | APE1 4uL | UDG treated |
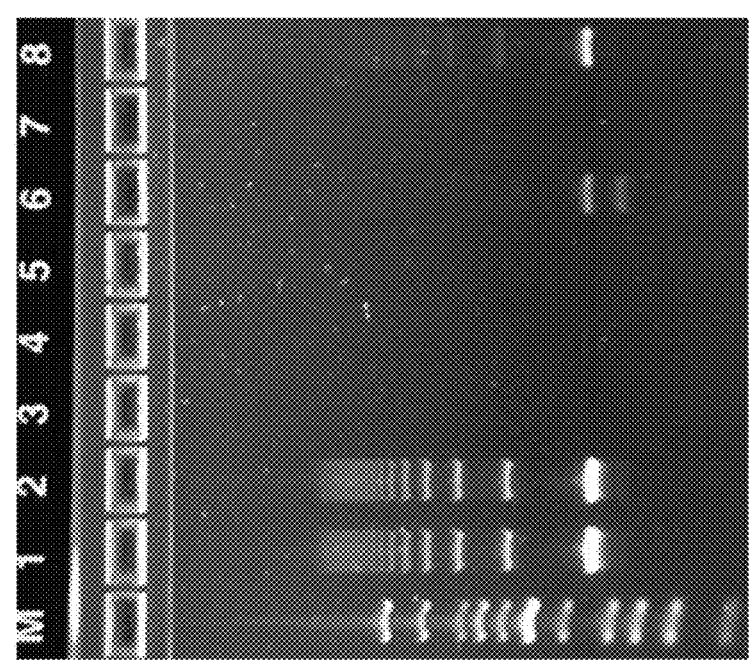

METHODS AND COMPOSITIONS FOR NUCLEIC ACID AMPLIFICATION

CROSS-REFERENCE TO RELATED APPLICATIONS

This application is a continuation of U.S. application Ser. No. 16/308,803, filed Dec. 10, 2018, which is a U.S. National Application filed under 35 U.S.C. § 371 of International Application No. PCT/US2017/036842, filed on Jun. 9, 2017, which claims the benefit of priority under 35 U.S.C. § 119 to U.S. provisional application No. 62/348, 402, filed Jun. 10, 2016; the disclosures of all the aforementioned applications are incorporated by reference in their entireties.

Throughout this application, various publications, patents, and/or patent applications are referenced. The disclosures of the publications, patents and/or patent applications in their entireties are hereby incorporated by reference into this application in order to more fully describe the state of the art to which this invention pertains.

REFERENCE TO SEQUENCE LISTING SUBMITTED VIA EFS-WEB

This application includes an electronically submitted sequence listing in .txt format. The .txt file contains a sequence listing entitled "LT01140US_ST25.txt" created on Dec. 10, 2018 and is 6,000 bytes in size. The sequence listing contained in this .txt file is part of the specification and is hereby incorporated by reference herein in its entirety.

BACKGROUND

Nucleic acid amplification is very useful in molecular biology and has wide applicability in practically every aspect of biology, therapeutics, diagnostics, forensics and research. Generally, amplicons are generated from a starting template using one or more primers, where the amplicons are homologous or complementary to the template from which they were generated. Multiplexed amplification can also streamline processes and reduce overheads. This application relates to methods and reagents for nucleic acid amplification and/or analysis using cleavable primers.

One example of such amplification is Recombinase Polymerase Amplification (RPA) which is a DNA amplification process that utilizes enzymes that hybridize oligonucleotide primers to their complementary partners in DNA (e.g., duplex DNA) followed by isothermal amplification. RPA offers a number of advantages over traditional methods of DNA amplification. These advantages include the lack of a need for any initial thermal or chemical denaturation, the ability to operate at low constant temperatures (e.g., isothermal conditions) without a need for absolute temperature control, as well as the observation that complete reactions (lacking target) can be stored in a dried condition. These characteristics demonstrate that RPA is a uniquely powerful tool for developing portable, accurate, and instrument-free nucleic acid detection tests. However, use of standard primers in RPA methods may result in nonspecific amplification product and/or primer dimer products, which reduce the efficiency of the reaction especially in the instance of next gen sequencing. Furthermore, primer design constraints are a drawback of RPA.

SUMMARY

Herein are provided blocked primers (e.g., oligonucleotide primers) containing a ribose base separating a 5' domain and a 3' domain of the primers, optionally for use in amplification reactions, especially isothermal reactions such as recombinase polymerase amplification (RPA). The ribose base moiety can be cleaved by certain endonuclease enzymes such as RNase H. The use of at least one such blocked primer (e.g., forward and/or reverse oligonucleotide primers), and an endonuclease that cleaves ribobase(s) (e.g. RNase H) after primer binding to a template DNA, reduces nonspecific amplification products providing an improved method for amplification of nucleic acid. Specific and surprising configurations for such primers have been identified, that provide effective primers for reactions that involve endonuclease cleavage of the primers, such as amplification reactions. Amplification reactions can include but are not limited to PCR (Polymerase Chain Reaction), HCR (Hybridization Chain Reaction), RCA (Rolling Circle Amplification), RPA (Recombinase Polymerase Amplification), LAMP (Loop mediated isothermal amplification), HDA (Helicase Dependent Amplification), cluster-generation methods such as bridge amplification (e.g. U.S. Pat. Appln. No. 2008/0009420 (Schroth et al.)) and "template-walking" (e.g. U.S. Pat. Appln. No. 2012/083189 (Li et al.)).

Methods, reagents and products of nucleic acid amplification and/or analysis are provided herein. In some embodiments, the present teachings provide compositions, systems, methods, apparatuses and kits for nucleic acid amplification.

Methods are provided for cleaving a double-stranded nucleic acid with an endonuclease, comprising the steps of (1) forming a reaction mixture comprising template nucleic acids (e.g., nucleic acid templates) and primers which include a cleavable moiety (e.g., a ribose base), wherein the primers are at least partly complementary to the template nucleic acid, (2) exposing the resulting mixture to conditions suitable for hybridization between the primers and the template nucleic acids, and (3) cleaving the primers at the cleavable moiety with the endonuclease, where the primers are at least partly hybridized to the template nucleic acids. In some embodiments, the endonuclease selectively cleaves the primers. In some embodiments, the endonuclease does not cleave the primers at other nucleotide positions. In some embodiments, the endonuclease cleaves a significant fraction of primers. In some embodiments, the endonuclease cleaves the primers less efficiently at elevated temperatures. In some embodiments, the endonuclease is RNase H2. In some embodiments, the cleavable moiety is a ribose base (e.g., a ribonucleotide). In some embodiments, the cleaving step is performed at a temperature below 60° C. (e.g. at room temperature or about 20-50° C., 20-30° C., 20-40° C., 25-40° C., 30-40° C., 35-40° C., or 40-50° C.). In some embodiments, the reaction mixture is contacted with amplification reagents and/or subjected to amplification conditions. In some embodiments, the reaction mixture further comprises a plurality of second primers that are reverse-complementary to the template nucleic acid, and the second primers optionally comprise a cleavable moiety (e.g., a ribose base), where the cleavable moiety is situated more than 5 nucleotides away from the 3' end of the oligonucleotide (e.g., at least 7, 10, 12, 15 or 20 nucleotides).

In some embodiments, the disclosure relates to methods for cleaving one or more blocked primers, comprising the steps of forming a reaction mixture by combining a nucleic acid template, a forward primer, a reverse primer, an RNase H enzyme, and optionally a source of reactive nucleotides such as dNTPs, and optionally a buffer, wherein the forward primer binds to a forward primer binding site on the nucleic acid template and the reverse primer binds to a reverse primer binding site on the nucleic acid template, wherein one or both of the forward or reverse primers is blocked, and wherein the blocked primer comprises a 5' domain and a 3' domain separated by at least one cleavable nucleotide (e.g., a ribobase), wherein the 5' domain is at least 10 nucleotides in length (e.g. 10 to 100 nucleotides in length) and the 3' domain is at least 10 nucleotides in length (e.g. 10 to 100, 10 to 90, 10 to 80, 10 to 75, 10 to 60, or 10 to 50 nucleotides in length); and optionally incubating the reaction mixture under substantially isothermal, or isothermal, amplification conditions between 20° C. and 50° C. (e.g. 25° C. and 40° C., 30° C. and 40° C., or 35° C. and 40° C.) for 10 minutes to 120 minutes, thereby amplifying the nucleic acid template. In an embodiment the reaction mixture optionally comprises at least one or more of: a polymerase, a recombinase, a single-stranded binding protein, or a recombinase loading protein.

In some embodiments, the disclosure relates to methods for cleaving a blocked primer, comprising the steps of forming a reaction mixture by combining a nucleic acid template having a forward primer binding sequence and a reverse primer binding sequence, and a blocked forward primer (i.e. non-extendable primer; i.e. forward primer that is not extendable by a polymerase), a reverse primer which is optionally blocked, an RNase H enzyme, and optionally a buffer comprising a divalent cation, wherein the forward primer binding sequence is complementary or identical to at least a portion of the blocked forward primer and the reverse primer binding sequence is complementary or identical to at least a portion of the blocked reverse primer, and wherein the blocked forward primer and the blocked reverse primer comprise a 5' domain and a 3' domain separated by at least one cleavable nucleotide (e.g. comprising a ribobase), wherein the 5' domain is at least 10 (e.g. 10 to 70, 10 to 60, 10 to 50, or 10 to 40) nucleotides in length and the 3' domain is at least 10 (e.g. 10 to 70, 10 to 60, 10 to 50, 10 to 40 or 10 to 25) nucleotides in length; and optionally incubating the reaction mixture under substantially isothermal amplification conditions (e.g., between 20° C. and 50° C. (e.g. 25° C. and 40° C., 30° C. and 40° C., or 35° C. and 40° C.)) for 15 minutes to 60 minutes, thereby amplifying the nucleic acid template. In some embodiments, the reaction mixture optionally comprises at least one or more of: a polymerase, a recombinase, a single-stranded binding protein, or a recombinase loading protein.

In some embodiments, the disclosure relates to methods for nucleic acid amplification, comprising the steps of forming a reaction mixture by combining at least two different polynucleotide templates comprising both a first primer binding sequence and a second primer binding sequence, a recombinase, a recombinase accessory protein, a polymerase, a first blocked universal primer, a second optionally blocked universal primer, an RNase H enzyme, and optionally dNTPs and a buffer, wherein the reaction mixture is in contact with a support having the first blocked universal primer bound (e.g., immobilized) thereto, wherein the first primer binding sequence is complementary or identical to at least a portion of the first blocked universal primer and the second primer binding sequence is complementary or identical to at least a portion of the second blocked universal primer, and wherein the first blocked universal primer and the second blocked universal primer comprise a 5' domain and a 3' domain separated by a nucleotide comprising a ribobase, w wherein the 5' domain is 10 to 70, 10 to 60, 10 to 50, or 10 to 40 nucleotides in length and the 3' domain is 10 to 70, 10 to 60, 10 to 50, 10 to 40 or 10 to 25 nucleotides in length; and forming at least two substantially monoclonal nucleic acid populations by using the polymerase to amplify each of said at least two different polynucleotide templates onto different sites on the solid support, within the same reaction mixture of step (a) under substantially isothermal conditions. The amplified monoclonal nucleic acid populations may be sequenced.

In some embodiments, the blocked forward primer and the blocked reverse primer comprise a 5' domain and a 3' domain separated by a nucleotide comprising a ribobase, wherein the 5' domain is 10 to 100 nucleotides in length and the 3' domain is 11 to 30 nucleotides in length. In embodiments the 5' domain is 15 to 25 nucleotides in length or greater than 25 nucleotides. In some embodiments, the 5' domain 15 to 50 nucleotides in length. In some embodiments, the ribobase is rU, rG, rC or rA.

In some embodiments, the 3' domain is 14 to 25 nucleotides in length or 15 to 25 nucleotides in length. In some embodiments, a 3' nucleotide of the 3' domain of the forward primer is mismatched to the forward primer binding sequence.

In some embodiments the recombinase is selected from the group consisting of uvsX, RecA, RadA, RadB, Rad 51, a homologue thereof, a functional analog thereof and a combination thereof. In some embodiments, the reaction mixture comprises uvsY accessory protein and uvsX recombinase.

In some embodiments, the RNase H enzyme is RNase HII. In some embodiments, the RNase H enzyme is RNase HII and the incubating temperature is between 35° C. and 42° C.

In some embodiments, the RNase H enzyme is present at a concentration from 5 U to 200 U/50 μL, or from 10 to 90 U/50 μL.

BRIEF DESCRIPTION OF THE DRAWINGS

FIG. 4 is a photo of a gel showing the results of blocked primer configuration screening with V4 and V5 primers by comparing DNA template amplification using the blocked primers.

FIG. 6 is a photo of a gel showing the results of DNA template amplification wherein nonspecific amplification using a non-template control reduced or eliminated using blocked primers of the invention.

FIG. 8A is a photo of two gels showing the results of RNase H enzyme unit titration by analyzing DNA amplification using various concentrations of RNase H enzyme in an RPA reaction with blocked primers.

FIG. 8B is a photo of a gel showing the results of RNase H enzyme unit titration by analyzing DNA amplification using various concentrations of RNase H enzyme in an RPA reaction with blocked primers.

FIG. 9 is a photo of a gel showing the results of DNA amplification using two different pellet formulations of enzymes rehydrated in an RPA reaction with blocked primers of the invention and regular primer controls.

FIG. 10 is a list of exemplary blocked primer and adapter sequences.

FIG. 11 is a list of exemplary primer sequences for amplification on a solid surface.

FIG. 12A is a table showing the reaction volumes and times for an amplification sequencing reaction with results shown in FIG. 12B.

FIG. 12B is a table that lists a comparison of DNA template amplification on a solid support using RNase H cleavable blocked primers of the invention followed by sequencing of the amplified template.

FIG. 13 is a photo of a gel showing the results of DNA amplification using Endo IV endonuclease and an abasic cleavable blocked primer in an RPA reaction.

FIG. 14 is a photo of a gel showing the results of DNA amplification using APE 1 endonuclease and an abasic cleavable blocked primer in a RPA reaction as compared to a ribobase cleavable blocked primer and RNase HII enzyme.

FIG. 15 is a photo of a gel showing the results of DNA amplification using the endonuclease APE 1 or Endo IV and an abasic blocked primer in a RPA reaction as compared to a ribobase cleavable blocked primer and RNase HII enzyme and controls.

DETAILED DESCRIPTION

Figure 1:
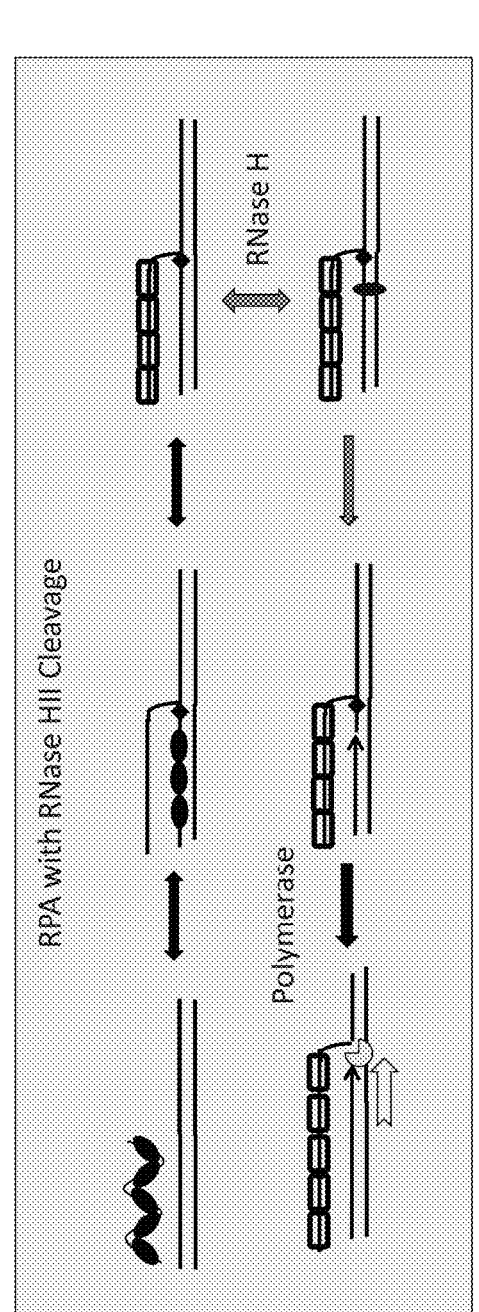
FIG. 1 is a non-limiting schematic of RPA with RNase H enzyme cleavage methods. A standard RPA is shown in the top portion of FIG. 1. An RPA with RNase H cleavage is shown in the lower portion of FIG. 1. The two inverted ovals around single chain represent recombinase bound to oligonucleotide. The open rectangles represent single stranded binding protein. The solid diamond represents a blocking moiety. The single vertical oval across two strands represents RNase bound to double stranded nucleic acid. The ¾ open circle represents a polymerase.

In some embodiments, reducing nonspecific amplification including reducing primer dimer formation in nucleic acid amplification reactions. In some embodiments, the reduced non-specific amplification can be achieved in an isothermal amplification reaction, for example using a recombinase-mediated amplification reaction such as RPA (recombinase-polymerase amplification). In some embodiments, simplified primer designs can be used for such reactions. In some embodiments, the methods, compositions, and kits use blocked primers that comprise one or more cleavable moieties (e.g., ribose bases) that separate a 5' domain and 3' domain of the primer, wherein an enzyme (e.g., ribo-endo-nuclease, such as RNase H), cleaves the primer at the cleavable moiety location thereby removing the blocking moiety. The 5' domain of the primer remains hybridized to the template nucleic acid while the 3' domain is removed. In some embodiments, the methods, compositions and kits identify surprising ranges for 5' and especially 3' domain nucleotide lengths of the blocked primers. These domain lengths, discussed below in detail, surprisingly result in efficient amplification of the template nucleic acid and surprisingly reduce or even eliminate primer dimer product formation and nonspecific amplification. In some embodiments, the methods include clonal amplification that utilize recombinase-mediated amplification and the improved blocked primers. In some embodiments, the methods include using especially effective concentration ranges (excess concentration) for RNase H in such recombinase amplification reactions using blocked primers that include a ribobase.

In some embodiments, therefor amplifying a nucleic acid template, that includes forming a reaction mixture by combining the nucleic acid template (e.g., a template polynucleotide), a polymerase, a recombinase, a forward primer, a reverse primer, wherein at least one of the forward primer or the reverse primer is a blocked primer, dNTPs, an RNase H enzyme, and a buffer. In some embodiments, the blocked primer is a blocked forward primer that binds to a forward primer binding site on the nucleic acid template and the reverse primer binds to a reverse primer binding site on the reverse complement of the nucleic acid template. The blocked forward primer comprises a 5' domain and a 3' domain separated by at least one nucleotide comprising a ribobase and a blocking group on the 3' end of the primer. The reaction mixture, in some embodiments, is incubated under substantially isothermal amplification conditions to amplify the nucleic acid template.

In some embodiments, methods for amplifying nucleic acid template(s) upstream of sequencing methods. Nucleic acid templates for these embodiments can be at least some, and typically all members of a nucleic acid sequencing template library. In some embodiments, the method includes forming a reaction mixture by combining at least two different polynucleotide templates comprising both a first primer binding sequence and a second primer binding sequence, a recombinase, a recombinase accessory protein, a polymerase, a first blocked universal primer attached to a support, a second optionally blocked universal primer, dNTPs, an RNase H enzyme, and a buffer, wherein the reaction mixture is in contact with the support, wherein the first primer binding sequence is complementary or identical to at least a portion of the first blocked universal primer and the second primer binding sequence is complementary or identical to at least a portion of the second blocked universal primer. The polymerase, by amplifying the at least two different polynucleotide templates, forms at least two substantially monoclonal nucleic acid populations onto different sites on the solid support, within the same reaction mixture of the first step under substantially isothermal conditions. This multi-clonal population of amplified nucleic acid template may then be used in sequencing workflow methods, such as high throughput sequencing methods.

In some embodiments, the methods use recombinase to denature, or partially denature, double stranded nucleic acid templates, which can be carried out at isothermal conditions with a polymerase, and is referred to as recombinase-polymerase amplification (RPA) (see, e.g., WO2003072805, hereby incorporated by reference in its entirety). In some embodiments, the partial denaturation and/or amplification, including any one or more steps or methods described in the teachings herein, can be achieved using a recombinase and/or single-stranded binding protein. Suitable recombinases include RecA and its prokaryotic or eukaryotic homologues, or functional fragments or variants thereof, optionally in combination with one or more single-strand binding proteins (SSBs). In some embodiments, the recombinase optionally binds single-stranded DNA (ssDNA) such as the blocked primers, to form a nucleoprotein filament strand which invades a double-stranded region of homology on a template. See FIG. 1. This optionally creates a short hybrid and a displaced strand bubble known as a D-loop. In FIG. 1, the free 3'-end of the hybridized primer after cleavage by the RNase H enzyme is extended by DNA polymerases to synthesize a new complementary strand. The complementary strand displaces the originally-paired partner strand of the template as it elongates. In some embodiments, the one or more of a pair of blocked primers are contacted with one or more recombinases before being contacted with a template which is optionally double-stranded.

In any of the methods described herein, amplification of a template optionally comprises contacting at least one blocked primer with a template strand, which optionally has a region of complementarity to at least one blocked primer. After hybridization of the blocked primer to the template DNA, the blocked primer is cleaved at the cleavable moiety (e.g., ribose base) location thereby liberating the 3' domain of the blocked primer. The newly formed 3' end of the 5' domain of the primer is then extended along the template with one or more polymerases (e.g., in the presence of dNTPs) to generate a double stranded nucleic acid and a displaced template strand. The amplification reaction can comprise repeated cycles of such contacting and extending until a desired degree of amplification is achieved, including, In some embodiments, substantially monoclonal amplification of the template DNA. Optionally the displaced strand of nucleic acid is amplified by a concurrent amplification reaction. Optionally, the displaced strand of nucleic acid is amplified by contacting it in turn with one or more complementary blocked primers and extending the complementary primer (after cleavage with an RNase H enzyme) by any strategy described herein. Optionally before a blocked primer is contacted with a template nucleic acid, it is first contacted with an amplification enzyme (e.g. a recombinase or a polymerase) which binds to the primer. Any amplification enzyme that has not associated with the one or more blocked primers is optionally removed.

In some embodiments, the disclosure relates generally to methods, as well as related compositions and kits which utilize at least one blocked RNase cleavable primer in the amplification of template nucleic acid. The blocked primer can be the forward primer, reverse primer or both. A forward primer and reverse primer typically form a primer pair for amplification. The forward primer binds a forward primer binding sequence in a forward direction on a forward strand. The reverse primer binds to a reverse primer binding sequence in a reverse direction on the complement strand of the forward strand. The blocked primers can be universal primers, which can, for example, bind to a target sequence in a gene or other sequence of interest, bind to a sequence found in a plasmid cloning vector, or in some embodiments, bind to universal adaptors found on or near the ends of template nucleic acids of a nucleic acid library. In some embodiments, one or more of the universal primers does not contain any target (template) specific sequences. In some embodiments, both the forward and reverse blocked primers of the invention are universal primers, which hybridize to a universal adapter sequence in the nucleic acid template. See Example 5. In some embodiments, only one of the forward and reverse blocked primers of the invention is a universal primer. Provided at least one primer is a blocked primer, then the other primers, forward or reverse, can be standard (non-blocked) primers. In some embodiments, the disclosure relates generally to methods, as well as related compositions and kits, wherein blocked primers that are cleavable by RNase H. In some embodiments, the blocked primers contain at least four components; a 5' domain, at least one ribobase, which is part of a cleavable segment, a 3' domain and a blocking moiety (See FIG. 2). Such primers can be referred to herein, for example, as "blocked primers", "non-extendable primer" or "blocked RNase cleavable primers." The ribobase, for example a ribonucleotide, when the primer is hybridized to a DNA template, is susceptible to cleavage by ribo-endonucleases, thereby separating the 5' domain and the 3' domain. See FIG. 2. Surprisingly, primers that included long domains, especially long 3' domains, were effective in reducing or eliminating primer dimer product formation. In some embodiments, the 3' domain is at least 7, 10, 12 or 14 nucleotides long, e.g. 14 to 30 nucleotides in length. In some embodiments, the blocked primer is between 15 and 200 nucleotides long, and includes a ribobase that is more than 5, 6, 7, 8, 9, 10, 11, 12, 13, 14, or 15 nucleotides away from the 3' terminus of the blocked primer, referred to in the alternative embodiment herein, as the oligonucleotide. It is noteworthy that the Alternative Embodiments herein include oligonucleotides that are not extendable by a polymerase (i.e. blocked oligonucleotides). Such blocked oligonucleotides include blocked primers that are cleavable by RNase H, as well as other oligonucleotides that are cleavable by other enzymes, as provided in the Alternative Embodiments section herein.

In some embodiments, the disclosure relates generally to methods, as well as related compositions and kits, which use at least oligonucleotide that is not extendable by a polymerase, such as one blocked primer that is cleavable by RNase H. In some embodiments, the blocked primer is a blocked forward primer. In some embodiments, the blocked primer is a blocked reverse primer. In some embodiments the blocked primers are complementary or identical to the template nucleic acid. In some embodiments, the blocked primers are universal forward and/or reverse primers, i.e., complementary or identical to multiple different templates that comprise different sequences. In some embodiments, the forward or the reverse primer is blocked. In some embodiments, both the forward and reverse primers are blocked.

In some embodiments, the one or more blocked primers comprise a "forward" primer and a "reverse" primer. Placing both primers and the template in contact optionally results in a first double stranded structure at a first portion of said first strand and a double stranded structure at a second portion of said second strand. Optionally, the 3' end of the forward and/or reverse primer (after cleavage by RNase H enzyme) is extended with one or more polymerases to generate a first and second double stranded nucleic acid and a first and second displaced strand of nucleic acid. Optionally, the second displaced strand is at least partially complementary to each other and can hybridize to form a daughter double stranded nucleic acid which can serve as double stranded template nucleic acid in a subsequent amplification cycles.

In some embodiments, In some embodiments, a blocked primer, forward primer and/or reverse primer, used in any of the methods provided herein includes a 5' domain and a 3' domain separated by at least one nucleotide comprising a ribobase. In some embodiments, the 5' domain and 3' domain are separated by a single ribobase. In some embodiments, the 5' domain and 3' domain are separated by consecutive ribobases, such as two, three, four, five or more ribobases. For example, the 5' domain and 3' domain can be separated by between 1 and 5 consecutive ribobases. In some embodiments, the ribobases are rU, rG, rA, or rC.

In some embodiments, the 3' domain of the blocked primers contain a blocking moiety, which is removed after cleavage at the ribobase location, once hybridized to the DNA template, with an RNase H enzyme. The block, or blocking group, is a chemical moiety on the end of the 3' primer and prevents primer extension, effectively blocking nucleic acid amplification. Once the blocking group is removed, the hybridized 5' domain of the primer is capable of participating in primer extension and RPA nucleic acid amplification. In some embodiments, the blocking group can be any moiety that prevents or blocks primer extension. In some embodiments, the block is a C3 spacer, a phosphate, biotin, or amine moiety.

In some embodiments, the 5' domain of the blocked primer can be any length, but is typically at least 10 nucleotides in length. In some embodiments, the 5' domain is between 10, 11, 12, 13, 14, 15, 16, 17, 18, 19, 20, 25, 30, 35, 40, 45, 50, 60, 70, 80 or 90 nucleotides on the low end of the range, and 11, 12, 13, 14, 15, 16, 17, 18, 19, 20, 25, 30, 35, 40, 45, 50, 60, 70, 80, 90, or 100 nucleotides on the high end of the range. In some embodiments, the 5' domain is typically at least 15 nucleotides in length and accordingly, in some embodiments is between 15, 16, 17, 18, 19, 20, 21, 22, 23, 24, 25, 26, 27, 28, 29, 30, 35, 40, 45, 50, 55, 60, 70, 80 or 90 nucleotides on the low end of the range, and 16, 17, 18, 19, 20, 21, 22, 23, 24, 25, 26, 27, 28, 29, 30, 35, 40, 45, 50, 55, 60, 70, 80, 90, or 100 nucleotides on the high end of the range. In some embodiments, the 5' domain can be at least 25 nucleotides in length and accordingly, in some embodiments the 5' domain is between 25, 26, 27, 28, 29, 30, 31, 32, 33, 34, 35, 36, 37, 38, 39, 40, 45, 50, 55, 60, 65, 70, 80 or 90 nucleotides on the low end of the range, and 26, 27, 28, 29, 30, 31, 32, 33, 34, 35, 36, 37, 38, 39, 40, 45, 50, 55, 60, 65, 70, 80, 90, or 100 nucleotides on the high end of the range. In some embodiments, the 5' domain is 30 nucleotides in length.

In some embodiments, the 5' domain can be between 10 and 60 nucleotides in length, and accordingly In some embodiments, the 5' domain is between 10, 11, 12, 13, 14, 15, 16, 17, 18, 19, 20, 25, 30, 35, 40, 45, 50 or 55 nucleotides on the low end of the range, and 11, 12, 13, 14, 15, 16, 17, 18, 19, 20, 25, 30, 35, 40, 45, 50, 55 or 60 nucleotides on the high end of the range. In some embodiments, the 5' domain can be between 15 and 60 nucleotides in length, and accordingly in some embodiments, the 5' domain is between 15, 16, 17, 18, 19, 20, 21, 22, 23, 24, 25, 30, 35, 40, 45, 50 or 55 nucleotides on the low end of the range, and 16, 17, 18, 19, 20, 21, 22, 23, 24, 25, 30, 35, 40, 45, 50, 55 or 60 nucleotides on the high end of the range. In some embodiments, the 5' domain can be between 25 and 60 nucleotides in length, and accordingly In some embodiments, the 5' domain is between 25, 26, 27, 28, 29, 30, 31, 32, 33, 34, 34, 35, 40, 45, 50 or 55 nucleotides on the low end of the range, and 26, 27, 28, 29, 30, 31, 32, 33, 34, 35, 40, 45, 50, 55 or 60 nucleotides on the high end of the range. In some embodiments, the 5' domain can be between 10 and 40 nucleotides in length, and accordingly In some embodiments, the 5' domain is between 10, 11, 12, 13, 14, 15, 16, 17, 18, 19, 20, 25, 30 or 35 nucleotides on the low end of the range, and 11, 12, 13, 14, 15, 16, 17, 18, 19, 20, 21, 22, 23, 24, 25, 30, 35 or 40 nucleotides on the high end of the range. In some embodiments, the 5' domain can be between 15 and 40 nucleotides in length, and accordingly in some embodiments, the 5' domain is between 15, 16, 17, 18, 19, 20, 25, 30 or 35 nucleotides on the low end of the range, and 16, 17, 18, 19, 20, 21, 22, 23, 24, 25, 30, 35 or 40 nucleotides on the high end of the range. In some embodiments, the 5' domain can be between 25 and 40 nucleotides in length, and accordingly in some embodiments, the 5' domain is 25, 26, 27, 28, 29, 30, 31, 32, 33, 34, 35, 36, 37, 38, 39 or 40 nucleotides in length.

In some embodiments, the 5' domain can be between 10 and 30 nucleotides in length, and accordingly in in some embodiments, the 5' domain is between 10, 11, 12, 13, 14, 15, 16, 17, 18, 19, 20, 21, 22, 23, 24, 25, 26, 27, 28 or 29 nucleotides on the low end of the range, and 11, 12, 13, 14, 15, 16, 17, 18, 19, 20, 21, 22, 23, 24, 25 or 30, nucleotides on the high end of the range. In some embodiments, the 5' domain can be between 15 and 30 nucleotides in length, and accordingly in some embodiments, the 5' domain is between 15, 16, 17, 18, 19, 20, 21, 22, 23, 24, 25, 26, 27, 28 or 29 nucleotides on the low end of the range, and 16, 17, 18, 19, 20, 21, 22, 23, 24, 25 or 30, nucleotides on the high end of the range.

In some embodiments, the blocked primers comprise a 5' domain that has a length of at least 10 nucleotides, at least 15 nucleotides, at least 25 nucleotides or 30 or more nucleotides. In some embodiments, the blocked primers comprise a 5' domain with a range of nucleotide lengths from 10 to 100, 10 to 60, 10 to 50, 10 to 40, 10 to 30 or 10 to 25. In some embodiments, the blocked primers comprise a 5' domain with a range of nucleotide lengths from 15 to 100, 15 to 60, 15 to 50, 15 to 40, 15 to 30 or 15 to 25. In some embodiments, the blocked primers comprise a 5' domain with a range of nucleotide lengths from 25 to 100, 25 to 60, 25 to 50, 25 to 40 or 25 to 30.

In some embodiments, the 5' domain can be between 15 and 25 nucleotides in length. See V5 primer configuration of FIG. 2, FIG. 10, Table 2 of Example 1 and corresponding FIGS. 4 and 5. In some embodiments, the 5' domain can be 15, 16, 17, 18, 19, 20, 21, 22, 23, 24, or 25 nucleotides in length. In some embodiments, the 5' domain can be 15 or 17 nucleotides in length. In some embodiments, the 5' domain of the blocked primers can be at least 25 nucleotides in length. See V2 primer configuration of FIG. 2, FIG. 10, Table 1 of Example 1 and corresponding FIG. 3. In some embodiments, the 5' domain can be between 25, 26, 27, 28, 29, 30, 31, 32, 33, 34, 35, 36, 37, 38, 39, 40, 45, 50 or 55 nucleotides on the low end of the range, and 26, 27, 28, 29, 30, 31, 32, 33, 34, 35, 36, 37, 38, 39, 40, 45, 50, 55, 60, 70, 75, or 80 nucleotides on the high end of the range. In some embodiments, the 5' domain can be between 30, 31, 32, 33 or 34 nucleotides on the low end of the range, and 31, 32, 33, 34 or 35 nucleotides on the high end of the range.

In some embodiments, the 3' domain is at least 10 nucleotides in length, but can be 7, 8 or 9 nucleotides in length. In some embodiments, the 3' domain is not less than 10 nucleotides in length and in some embodiments the 3' domain is not less 6 nucleotides in length. In some embodiments, the 3' domain is between 10 and 30 nucleotides in length, wherein the 3' domain is 10, 11, 12, 13, 14, 15, 16, 17, 18, 19, 20, 21, 22, 23, 24, 25, 26, 27, 28, 29 or 30 nucleotides in length. In some embodiments, the 3' domain is typically at least 14 nucleotides in length. In some embodiments, the 3' domain is between 14 and 30 nucleotides in length, wherein the 3' domain is 14, 15, 16, 17, 18, 19, 20, 21, 22, 23, 24, 25, 26, 27, 28, 29 or 30 nucleotides in length. In some embodiments, the 3' domain of the blocked primers is between 15 and 30 nucleotides in length, and accordingly In some embodiments, the 3' domain is 15, 16, 17, 18, 19, 20, 21, 22, 23, 24, 25, 26, 27, 28, 29 or 30 nucleotides in length. In both the V2 and V5 primer configuration illustrated in FIG. 2 and FIG. 10; and in the Examples section herein, the 3' domain was at least 14 nucleotides in length.

In some embodiments, the 3' domain is between 10 and 25 nucleotides in length, and accordingly in some embodiments, the 3' domain is 10, 11, 12, 13, 14, 15, 16, 17, 18, 19, 20, 21, 22, 23, 24 or 25 nucleotides in length. In some embodiments, the 3' domain is between 14 and 25 nucleotides in length, and accordingly in some embodiments, the 3' domain is 14, 15, 16, 17, 18, 19, 20, 21, 22, 23, 24 or 25 nucleotides in length. In some embodiments, the 3' domain of the blocked primers is between 15 and 25 nucleotides in length, and accordingly in some embodiments, the 3' domain is 15, 16, 17, 18, 19, 20, 21, 22, 23, 24 or 25 nucleotides in length. In some embodiments, the 3' domain of the blocked primers is between 14 and 20 nucleotides in length, and accordingly in some embodiments, the 3' domain is 14, 15, 16, 17, 18, 19 or 20 nucleotides in length. In some embodiments, the 3' domain of the blocked primers is between 15 and 20 nucleotides in length, and accordingly in some embodiments, the 3' domain is 15, 16, 17, 18, 19 or 20 nucleotides in length.

In some embodiments, the blocked primers comprise a 5' domain and a 3' domain with a length as disclosed herein. In some embodiments, the blocked primers comprise a 5' domain with a length between 10 and 100 nucleotides and a 3' domain with a length between 10 and 30 nucleotides, and accordingly in some embodiments, the 5' domain is between 10, 11, 12, 13, 14, 15, 16, 17, 18, 19, 20, 25, 30, 35, 40, 45, 50, 60, 70, 80 or 90 nucleotides on the low end of the range, and 11, 12, 13, 14, 15, 16, 17, 18, 19, 20, 25, 30, 35, 40, 45, 50, 60, 70, 80, 90, or 100 nucleotides on the high end of the range and the 3' domain is between 10 and 30 nucleotides, and accordingly in some embodiments, 10, 11, 12, 13, 14, 15, 16, 17, 18, 19, 20, 21, 22, 23, 24, 25, 26, 27, 28, 29 or 30 nucleotides in length. In some embodiments, the blocked primers comprise a 5' domain with a length between 10 and 100 nucleotides and a 3' domain with a length between 14 and 30 nucleotides, and accordingly in some embodiments, the 5' domain is between 10, 11, 12, 13, 14, 15, 16, 17, 18, 19, 20, 25, 30, 35, 40, 45, 50, 60, 70, 80 or 90 nucleotides on the low end of the range, and 11, 12, 13, 14, 15, 16, 17, 18, 19, 20, 25, 30, 35, 40, 45, 50, 60, 70, 80, 90, or 100 nucleotides on the high end of the range and the 3' domain is between 14 and 30, and accordingly in some embodiments, 14, 15, 16, 17, 18, 19, 20, 21, 22, 23, 24, 25, 26, 27, 28, 29 or 30 nucleotides in length. In some embodiments, the blocked primers comprise a 5' domain with a length between 10 and 100 nucleotides and a 3' domain with a length between 15 and 30 nucleotides, and accordingly in some embodiments, the 5' domain is between 10, 11, 12, 13, 14, 15, 16, 17, 18, 19, 20, 25, 30, 35, 40, 45, 50, 60, 70, 80 or 90 nucleotides on the low end of the range, and 11, 12, 13, 14, 15, 16, 17, 18, 19, 20, 25, 30, 35, 40, 45, 50, 60, 70, 80, 90, or 100 nucleotides on the high end of the range and the 3' domain is between 15 and 30 nucleotides in length, and accordingly in some embodiments, the 3' domain is 15, 16, 17, 18, 19, 20, 21, 22, 23, 24, 25, 26, 27 or 28 on the low end of the range, and 16, 17, 18, 19, 20, 21, 22, 23, 24, 25, 26, 27, 28, 29 or 30 nucleotides in length on the high end of the range. In some embodiments, the blocked primers comprise a 5' domain with a length of 30 nucleotides and a 3' domain with a length of 15 nucleotides.

In some embodiments, the blocked primers comprise a 5' domain with a length between 15 and 60 nucleotides and a 3' domain with a length between 10 and 30 nucleotides, wherein the 5' domain is between 15, 16, 17, 18, 19, 20, 21, 22, 23, 24, 25, 30, 35, 40, 45, 50 or 55 nucleotides on the low end of the range, and 16, 17, 18, 19, 20, 21, 22, 23, 24, 25, 30, 35, 40, 45, 50, 55 or 60 nucleotides on the high end of the range and the 3' domain is 10, 12, 13, 14, 15, 16, 17, 18, 19, 20, 21, 22, 23, 24, or 25 nucleotides on the low end of the range, and 15, 16, 17, 18, 19, 20, 21, 22, 23, 24, 25, 26, 27, 28, 29 or 30 nucleotides in length on the high end of the range. In some embodiments, the blocked primers comprise a 5' domain with a length between 15 and 60 nucleotides and a 3' domain with a length between 14 and 30 nucleotides, wherein the 5' domain is between 15, 16, 17, 18, 19, 20, 21, 22, 23, 24, 25, 30, 35, 40, 45, 50 or 55 nucleotides on the low end of the range, and 16, 17, 18, 19, 20, 21, 22, 23, 24, 25, 30, 35, 40, 45, 50, 55 or 60 nucleotides on the high end of the range and the 3' domain is 14, 15, 16, 17, 18, 19, 20, 21, 22, 23, 24, 25, 26, 27, 28, 29 or 30 nucleotides in length. In some embodiments, the blocked primers comprise a 5' domain with a length between 15 and 60 nucleotides and a 3' domain with a length between 15 and 30 nucleotides, wherein the 5' domain is between 15, 16, 17, 18, 19, 20, 21, 22, 23, 24, 25, 30, 35, 40, 45, 50 or 55 nucleotides on the low end of the range, and 16, 17, 18, 19, 20, 21, 22, 23, 24, 25, 30, 35, 40, 45, 50, 55 or 60 nucleotides on the high end of the range and the 3' domain is 15, 16, 17, 18, 19, 20, 21, 22, 23, 24, 25, 26, 27, 28, 29 or 30 nucleotides in length.

In some embodiments, the blocked primers comprise a 5' domain with a length between 25 and 60 nucleotides in length and a 3' domain with a length between 10 and 30 nucleotides, wherein the 5' domain is between 25, 26, 27, 28, 29, 30, 31, 32, 33, 34, 34, 35, 40, 45, 50 or 55 nucleotides on the low end of the range, and 26, 27, 28, 29, 30, 31, 32, 33, 34, 35, 40, 45, 50, 55 or 60 nucleotides on the high end of the range and the 3' domain is 10, 11, 12, 13, 14, 15, 16, 17, 18, 19, 20, 21, 22, 23, 24, 25, 26, 27, 28, 29 or 30 nucleotides in length. In some embodiments, the blocked primers comprise a 5' domain with a length between 25 and 60 nucleotides in length and a 3' domain with a length between 14 and 30 nucleotides, wherein the 5' domain is between 25, 26, 27, 28, 29, 30, 31, 32, 33, 34, 34, 35, 40, 45, 50 or 55 nucleotides on the low end of the range, and 26, 27, 28, 29, 30, 31, 32, 33, 34, 35, 40, 45, 50, 55 or 60 nucleotides on the high end of the range and the 3' domain is 14, 15, 16, 17, 18, 19, 20, 21, 22, 23, 24, 25, 26, 27, 28, 29 or 30 nucleotides in length. In some embodiments, the blocked primers comprise a 5' domain with a length between 25 and 60 nucleotides in length and a 3' domain with a length between 15 and 30 nucleotides, wherein the 5' domain is between 25, 26, 27, 28, 29, 30, 31, 32, 33, 34, 34, 35, 40, 45, 50 or 55 nucleotides on the low end of the range, and 26, 27, 28, 29, 30, 31, 32, 33, 34, 35, 40, 45, 50, 55 or 60 nucleotides on the high end of the range and the 3' domain is 15, 16, 17, 18, 19, 20, 21, 22, 23, 24, 25, 26, 27, 28, 29 or 30 nucleotides in length.

In some embodiments, the blocked primers comprise a 5' domain with a length between 15 and 30 nucleotides and a 3' domain with a length between 14 and 30 nucleotides, wherein the 5' domain is 15, 16, 17, 18, 19, 20, 21, 22, 23, 24, 25, 26, 27, 28, 29 or 30 nucleotides in length and the 3' domain is 14, 15, 16, 17, 18, 19, 20, 21, 22, 23, 24, 25, 26, 27, 28, 29 or 30 nucleotides in length. In some embodiments, the blocked primers comprise a 5' domain that is 30 nucleotides in length and a 3' domain that is 15 nucleotides in length. See Example 2.

In some embodiments, the blocked primers comprise a 5' domain with a length of 24 or 25 nucleotides, a ribobase such as rA or rG, a 3' domain with a length of 5 or 6 nucleotides and a blocking moiety. See FIG. 10 and V1 primer configuration. In some embodiments, the blocked primers comprise a 5' domain with a length of 30, 31, 32, 33, 34 or 35 nucleotides, a ribobase such as rC or rU, a 3' domain with a length of 15, 16 or 17 nucleotides and a blocking moiety. See FIG. 10 and V2 primer configuration. In some embodiments, the blocking primers comprise a 5' domain with a length of 31 or 35 nucleotides, a ribobase such as rC, a 3' domain with a length of 5 nucleotides and a blocking moiety. See FIG. 10 and V3 primer configuration. In some embodiments, the blocked primers comprise a 5' domain with a length of 30 or 32 nucleotides, a ribobase such as rU, a 3' domain with a length of 10 nucleotides and a blocking moiety. See FIG. 10 and V4 primer configuration. In some embodiments, the blocked primers comprise a 5' domain with a length of 15 or 17 nucleotides, a ribobase such as rG or rU, a 3' domain with a length of 15 nucleotides and a blocking moiety. See FIG. 10 and V5 primer configuration.

In some embodiments, the blocked primers comprise a 5' domain that is at least 25 nucleotides and a 3' domain that is at least 14 nucleotides in length, wherein the 5' domain is between 25, 26, 27, 28, 29, 30, 31, 32, 33, 34, 35, 36, 37, 38, 39, 40, 45, 50, 55, 60, 65, 70, 80 or 90 nucleotides on the low end of the range, and 26, 27, 28, 29, 30, 31, 32, 33, 34, 35, 36, 37, 38, 39, 40, 45, 50, 55, 60, 65, 70, 80, 90, or 100 nucleotides on the high end of the range and the 3' domain is 14, 15, 16, 17, 18, 19, 20, 21, 22, 23, 24, 25, 26, 27, 28, 29 or 30 nucleotides in length. See primer configuration V2 of Example 1. In some embodiments, the blocked primers comprise a 5' domain that is 15 to 25 nucleotides and a 3' domain that is at least 14 nucleotides in length, wherein the 5' domain is 15, 16, 17, 18, 19, 20, 21, 22, 23, 24, 25 nucleotides in length and the 3' domain is 14, 15, 16, 17, 18, 19, 20, 21, 22, 23, 24, 25, 26, 27, 28, 29 or 30 nucleotides in length. See primer configuration V5 of Example 1.

In some embodiments, the blocked primers comprise a 5' domain that is at least 25 nucleotides wherein, the 3' domain is 14 nucleotides; or the 3' domain is 15 nucleotides; or the 3' domain is 16 nucleotides; or the 3' domain is 17 nucleotides; or the 3' domain is 18 nucleotides; or the 3' domain is 19 nucleotides; or the 3' domain is 20 nucleotides; or the 3' domain is 21 nucleotides; or the 3' domain is 22 nucleotides; or the 3' domain is 23 nucleotides; or the 3' domain is 24 nucleotides; or the 3' domain is 25 nucleotides; or the 3' domain is 26 nucleotides; or the 3' domain is 27 nucleotides; or the 3' domain is 28 nucleotides; or the 3' domain is 29 nucleotides; or the 3' domain is 30 nucleotides. In some embodiments, the blocked primers comprise a 5' domain that is between 15 and 25 nucleotides in length, wherein, the 3' domain is 14 nucleotides; or the 3' domain is 15 nucleotides; or the 3' domain is 16 nucleotides; or the 3' domain is 17 nucleotides; or the 3' domain is 18 nucleotides; or the 3' domain is 19 nucleotides; or the 3' domain is 20 nucleotides; or the 3' domain is 21 nucleotides; or the 3' domain is 22 nucleotides; or the 3' domain is 23 nucleotides; or the 3' domain is 24 nucleotides; or the 3' domain is 25 nucleotides; or the 3' domain is 26 nucleotides; or the 3' domain is 27 nucleotides; or the 3' domain is 28 nucleotides; or the 3' domain is 29 nucleotides; or the 3' domain is 30 nucleotides.

In some embodiments, the blocked primers comprise a 5' domain that is 10 to 100 nucleotides in length and a 3' domain that is 11 to 30 nucleotides in length. In some embodiments, the 5' domain is 15 to 50 nucleotides in length. In some embodiments, the 5' domain is 15 to 30 nucleotides. In some embodiments, the 3' domain is 14 to 25 nucleotides in length or 15 to 25 nucleotides length. In some embodiments, the 3' domain is 14 to 20 nucleotides in length wherein the ribobase is rU, rG or rA. In some embodiments, the 3' domain is 15 to 20 nucleotides in length wherein the ribobase is rU, rG or rA.

In some embodiments, the 3' domain optionally comprises a mismatched base pair. In some embodiments, a 3' nucleotide of the 3' domain of a blocked forward primer is mismatched to a forward primer binding sequence. In some embodiments, a 3' nucleotide of the 3' domain of a blocked reverse primer is mismatched to a reverse primer binding sequence. In some embodiments, the 3' domain optionally comprises more than one mismatched base pair.

In some embodiments, the methods, compositions and kits described herein for amplifying nucleic acid template, at least one blocked primer is used wherein the 3' domain is from 10 to 30 nucleotides in length. In some embodiments, the compositions and kits comprise at least one blocked primer wherein the 3' domain is from 10 to 30 nucleotides in length.

In some embodiments, the disclosure relates generally to methods, as well as related compositions and kits for amplifying nucleic acids, a standard (non-blocked) primer can be used in combination with at least one blocked primer. In some embodiments, the non-blocked primers typically have a free 3' hydroxyl. It is understood that use of the term "standard primer" refers to a non-blocked primer (no ribobase cleavage location or blocking moiety) and not a blocked primer of the invention. In some embodiments, standard primers comprise polymers of deoxyribonucleotides or analogs thereof. In some embodiments, standard primers comprise naturally-occurring, synthetic, recombinant, cloned, amplified, or unamplified forms. In some embodiments, non-blocked primers include phosphodiester linkages between all nucleotides.

In some embodiments, standard primers can be any length, including about 5-100 nucleotides, or about 10-100 nucleotides, or about 15-100 nucleotides, or about 20-100 nucleotides, or longer.

In some embodiments, the disclosure relates generally to methods, as well as related compositions and kits for amplifying nucleic acids, wherein in addition to the blocked primers discussed above, a reaction mixture is formed containing the necessary components for amplification of the template nucleic acid. Those components, in some embodiments, include one or more nucleic acid templates, a polymerase, a recombinase, a recombinase accessory protein, a forward primer, a reverse primer, dNTPs, an RNase H enzyme, a buffer, and optionally a sieving agent, and optionally a crowding agent, and optionally a single-stranded binding protein.

In some embodiments, methods for nucleic acid amplification can include at least one co-factor for recombinase or polymerase activity. In some embodiments, a co-factor comprises one or more divalent cation. Examples of divalent cations include magnesium, manganese and calcium. In some embodiments, the reaction mixture comprises a buffer comprising a divalent cation. In embodiments the buffer comprises magnesium or manganese ions.

In some embodiments, the reaction mixture may be formed by the individual addition of each component to an aqueous or emulsion solution. In some embodiments, the reaction mixture can be in the form of a dehydrated pellet that requires rehydration prior to use. In some embodiments, the reaction mixture is in the form of a dehydrated pellet and comprises recombinase, recombinase accessory proteins, gp32, DNA polymerase, dNTPs, ATP, phosphocreatine, a crowding agent and creatine kinase. See Example 1. Rehydration buffer can include, for example, Tris buffer, potassium acetate salt and a crowding agent such as PEG.

In some embodiments, the reaction mixture is in the form of a dehydrated pellet and comprises recombinase, recombinase accessory protein(s), gp32, T7 DNA polymerase, thioredoxin, dNTPs, ATP, phosphocreatine, a crowding agent and creatine kinase. In some embodiments, when a dehydrated pellet is used that includes reaction mixture components, the pellet is rehydrated with a rehydration buffer, template DNA, primers including blocked primers of the invention, RNase H enzyme and additional nuclease-free water are added to a final volume.

In some embodiments, a nucleic acid amplification reaction can be pre-incubated under conditions that inhibit premature reaction initiation. For example, one or more components of a nucleic acid amplification reaction can be withheld from a reaction vessel to prevent premature reaction initiation. To start the reaction, a divalent cation can be added (e.g., magnesium or manganese). In another example, a nucleic acid amplification reaction can be pre-incubated at a temperature that inhibits enzyme activity. The reaction can be pre-incubated at about 0-15° C., or about 15-25° C. to inhibit premature reaction initiation. The reaction can then be incubated at a higher temperature to induce enzymatic activity. In some embodiments, the reaction mixture is not exposed to a temperature above 40° C. during the amplification. Further details and examples of reaction mixtures and components thereof, are found herein, for example in discussions of composition embodiments as well as discussion herein related to individual components of the reaction mixtures and compositions.

In some embodiments, the disclosure relates generally to methods, as well as related compositions and kits for amplifying nucleic acids, wherein the nucleic acid templates (e.g., nucleic acid templates) include a forward primer binding site having a forward primer binding sequence and a reverse primer binding site having a reverse primer binding sequence. In some embodiments, the primers are referred to as a first and a second primer wherein the template comprises a first primer binding sequence and a second primer sequence. In embodiments the first and second primers are blocked universal primers, such as 3' blocked universal primers that are cleavable by RNase H. In some embodiments, the reaction mixture comprises one monoclonal template nucleic acid. In some embodiments, reaction mixture comprises at least two different (polyclonal) polynucleotide or nucleic acid templates.

In some embodiments, the reaction mixture for the methods for nucleic acid amplification comprise a plurality of different polynucleotides. In some embodiments, a plurality of different polynucleotides comprises single-stranded or double-stranded polynucleotides, or a mixture of both. In some embodiments, a plurality of different polynucleotides comprises polynucleotides having the same or different sequences. In some embodiments, a plurality of different polynucleotides comprises polynucleotides having the same or different lengths. In some embodiments, a plurality of different polynucleotides comprises about 2-10, or about 10-50, or about 50-100, or about 100-500, or about 500-1,000, or about 1,000-5,000, or about $10^3$-$10^6$, or about $10^6$-$10^{10}$ or more different polynucleotides. In some embodiments, a plurality of different polynucleotides comprises polymers of deoxyribonucleotides, ribonucleotides, and/or analogs thereof. In some embodiments, a plurality of different polynucleotides comprises naturally-occurring, synthetic, recombinant, cloned, amplified, unamplified or archived (e.g., preserved) forms. In some embodiments, a plurality of different polynucleotides comprises DNA, cDNA RNA or chimeric RNA/DNA, and nucleic acid analogs.

In some embodiments, a plurality of different polynucleotide templates amplified in methods provided herein can comprise a double-stranded polynucleotide library construct having a nucleic acid adaptor sequence on one or both ends. For example, a polynucleotide library construct can comprise a first and second end, where the first end is joined to a first nucleic acid adaptor. A polynucleotide library construct can also include a second end joined to a second nucleic acid adaptor. The first and second adaptors can have the same or different sequence. In some embodiments, at least a portion of the first or second nucleic acid adaptor (i.e., as part of the polynucleotide library construct) can hybridize to the first primer, which can be a universal primer. In some embodiments, a homologous recombination enzyme, as part of a nucleoprotein complex, can bind to a polynucleotide library construct having a first or second nucleic acid adaptor sequence.

In some embodiments, polynucleotide library constructs can be compatible for use in any type of sequencing platform including chemical degradation, chain-termination, sequence-by-synthesis, pyrophosphate, massively parallel, ion-sensitive, single molecule platforms, and combinations thereof.

In some embodiments, methods for nucleic acid amplification include diluting the amount of polynucleotides that are reacted with beads (e.g., beads attached with a plurality of a first primer, such as a first RNase cleavable blocked primer of the invention) to reduce the percentage of beads that react with more than one polynucleotide. In some embodiments, nucleic acid amplification reactions can be conducted with a polynucleotide-to-bead ratio that is selected to optimize the percentage of beads having a monoclonal population of polynucleotides attached thereto. For example, a nucleic acid amplification reaction can be conducted at anyone of polynucleotide-to-bead ratios in a range of about 1:1 or 1:2 to 1:500. In some embodiments, a polynucleotide-to-bead ratio includes about 1:1, or about 1:2, or about 1:5, or about 1:10, or about 1:25, or about 1:50, or about 1:75, or about 1:100, or about 1:125, or about 1:150, or about 1:175, or about 1:200, or about 1:225, or about 1:225, or about 1:250. In some embodiments, a nucleic acid amplification reaction can produce beads having zero types of polynucleotides attached thereto, other beads having one type of polynucleotide attached thereto, and other beads having more than one type of polynucleotides attached thereto.

In some embodiments, the disclosure relates generally to methods, as well as related compositions and kits for amplifying nucleic acids, wherein the reaction mixtures comprise a recombinase. Similarly, compositions and kits provided herein can include a recombinase. The recombinase can include any agent that is capable of inducing, or increasing the frequency of occurrence, of a recombination event. A recombination event includes any event whereby two different polynucleotides strands are recombined with each other. Recombination can include homologous recombination. The recombinase can be an enzyme, or a genetically engineered derivative thereof. The recombinase optionally can associate with (e.g., bind) a single-strand oligonucleotide (e.g., a first primer). In some embodiments, an enzyme that catalyzes homologous recombination can form a nucleoprotein complex by binding a single-stranded oligonucleotide. In some embodiments, a homologous recombination enzyme, as part of a nucleoprotein complex, can bind a homologous portion of a double-stranded polynucleotide. In some embodiments, the homologous portion of the polynucleotide can hybridize to at least a portion of the first primer. In some embodiment, the homologous portion of the polynucleotide can be partially or completely complementary to at least a portion of the first primer.

In some embodiments, a homologous recombination enzyme can catalyze strand invasion by forming a nucleoprotein complex and binding to a homologous portion of a double-stranded polynucleotide to form a recombination intermediate having a triple-strand structure (D-loop formation) (U.S. Pat. No. 5,223,414 to Zarling, U.S. Pat. Nos. 5,273,881 and 5,670,316 both to Sena, and U.S. Pat. Nos. 7,270,981, 7,399,590, 7,435,561, 7,666,598, 7,763,427, 8,017,339, 8,030,000, 8,062,850, and 8,071,308).

In some embodiments, the recombinase of the reaction mixtures, compositions, and kits provided herein can include any suitable agent that can promote recombination between polynucleotide molecules. The recombinase can be an enzyme that catalyzes homologous recombination. For example, the reaction mixture can include a recombinase that includes, or is derived from, a bacterial, eukaryotic or viral (e.g., phage) recombinase enzyme.

In some embodiments, a homologous recombination enzyme comprises wild-type, mutant, recombinant, fusion, or fragments thereof. In some embodiments, a homologous recombination enzyme comprises an enzyme from any organism, including myoviridae (e.g., uvsX from bacteriophage T4, RB69, and the like) *Escherichia coli* (e.g., recA), or human (e.g., RAD51). In some embodiments, the reaction mixture includes one or more recombinases selected from uvsX, RecA, RadA, RadB, Rad51, a homologue thereof, a functional analog thereof or a combination thereof. The recombinase in illustrative examples is uvsX. The UvsX protein can be present, for example, at 50-250 ng/ul or 100-200 ng/ul.

In some embodiments, methods for nucleic acid amplification comprise one or more accessory proteins. For example, an accessory protein can improve the activity of a recombinase enzyme (U.S. Pat. No. 8,071,308 granted to Piepenburg, et al.). In some embodiments, an accessory protein can bind single strands of nucleic acids, or can load a recombinase onto a nucleic acid. In some embodiments, an accessory protein comprises wild-type, mutant, recombinant, fusion, or fragments thereof. In some embodiments, accessory proteins can originate from any combination of the same or different species as the recombinase enzyme that are used to conduct a nucleic acid amplification reaction. Accessory proteins can originate from any bacteriophage including a myoviral phage. Examples of a myoviral phage include T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.8t, Rb49, phage Rb3, and phage LZ2. Accessory proteins can originate from any bacterial species, including *Escherichia coli, Sulfolobus* (e.g., *S. solfataricus*) or *Methanococcus* (e.g., *M. jannaschii*).

In some embodiments, methods for nucleic acid amplification can include single-stranded binding proteins. Single-stranded binding proteins include myoviral gp32 (e.g., T4 or RB69), Sso SSB from *Sulfolobus solfataricus*, MjA SSB from *Methanococcus jannaschii*, or *E. coli* SSB protein.

In some embodiments, methods for nucleic acid amplification can include proteins that can improve recombinase loading onto a nucleic acid. For example, a recombinase loading protein comprises a UvsY protein (U.S. Pat. No. 8,071,308 granted to Piepenburg). In some embodiments, the reaction mixture includes recombinase accessory proteins. In some embodiments, the recombinase accessory protein is uvsY. UvsY can be present, for example, at 20 ng/ul to 100 ng/ul.

In some embodiments, the reaction mixture used herein for nucleic acid amplification may include at least one co-factor for recombinase assembly on nucleic acids or for homologous nucleic acid pairing. In some embodiments, a co-factor comprises any form of ATP including ATP and ATPγS.

In some embodiments, methods for nucleic acid amplification can include at least one co-factor that regenerates ATP. For example, a co-factor comprises an enzyme system that converts ADP to ATP. In some embodiments, a co-factor comprises phosphocreatine and creatine kinase.

The reaction mixture further comprises nucleotides (dNTPs) for strand extension of one or more nucleic acid templates, and in some embodiments resulting in a clonal population of the template nucleic acid sequence. In some embodiments, the nucleotides are not extrinsically labeled. For example, the nucleotides can be naturally occurring nucleotides, or synthetic analogs that do not include fluorescent moieties, dyes, or other extrinsic optically detectable labels. Optionally, the reaction mixture includes nucleotides that are naturally occurring nucleotides. Optionally, the nucleotides do not include groups that terminate nucleic acid synthesis (e.g., dideoxy groups, reversible terminators, and the like).

Optionally, the reaction mixture includes nucleotides that are naturally occurring nucleotides. Optionally, the nucleotides do not include groups that terminate nucleic acid synthesis (e.g., dideoxy groups, reversible terminators, and the like). In some embodiments, the nucleotides comprise a label or tag, described in more detail below.

In some embodiments, the disclosure relates generally to methods, as well as related compositions and kits for nucleic acid amplification which include contacting (e.g., mixing) one or more nucleic acid templates with one or more primers in the presence of one or more enzymes capable of polymerization. In some embodiments, the one or more enzymes capable of polymerization include at least one polymerase and a recombinase. In some embodiments, the at least one polymerase includes a thermostable or thermolabile polymerase. In some embodiments, the at least one polymerase includes a biologically active fragment of a DNA or RNA polymerase that maintains sufficient catalytic activity to polymerize or incorporate at least one nucleotide under any suitable conditions. In one embodiment, the at least one polymerase comprises a mutated DNA or RNA polymerase that maintains sufficient catalytic activity to perform nucleotide polymerization under any suitable conditions. In another embodiment, the at least one polymerase includes one or more amino acid mutations that do not disrupt processivity of the polymerase; and wherein the at least one polymerase having at least one mutation maintains sufficient catalytic activity to perform polymerization.

In some embodiments, a polymerase includes any enzyme, or fragment or subunit of thereof, that can catalyze polymerization of nucleotides and/or nucleotide analogs. In some embodiments, a polymerase requires an extendible 3' end. For example, a polymerase requires a terminal 3' OH of a nucleic acid primer to initiate nucleotide polymerization. The polymerase can be other than a thermostable polymerase. For example, the polymerase can be active at 37° C. and/or more active at 37° C. than at 50° C., 60° C., 70° C. or higher.

In some embodiments, a polymerase comprises any enzyme that can catalyze the polymerization of nucleotides (including analogs thereof) into a nucleic acid strand. Typically, but not necessarily such nucleotide polymerization can occur in a template-dependent fashion. In some embodiments, a polymerase can be a high fidelity polymerase. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide, such as, for example, a reporter enzyme or a processivity-enhancing domain. Typically, the polymerase comprises one or more active sites at which nucleotide binding and/or catalysis of nucleotide polymerization can occur. In some embodiments, a polymerase includes or lacks other enzymatic activities, such as for example, 3' to 5' exonuclease activity or 5' to 3' exonuclease activity. In some embodiments, a polymerase can be isolated from a cell, or generated using recombinant DNA technology or chemical synthesis methods. In some embodiments, a polymerase can be expressed in prokaryote, eukaryote, viral, or phage organisms. In some embodiments, a polymerase can be post-translationally modified proteins or fragments thereof.

In some embodiments, the polymerase can include any one or more polymerases, or biologically active fragment of a polymerase, which is described in U.S. Patent Publ. No. 2011/0262903 to Davidson et al., published Oct. 27, 2011, and/or International PCT Publ. No. WO 2013/023176 to Vander Horn et al., published Feb. 14, 2013.

In some embodiments, a polymerase can be a DNA polymerase and include without limitation bacterial DNA polymerases, eukaryotic DNA polymerases, archaeal DNA polymerases, viral DNA polymerases and phage DNA polymerases.

In some embodiments, a polymerase can be a replicase, DNA-dependent polymerase, primases, RNA-dependent polymerase (including RNA-dependent DNA polymerases such as, for example, reverse transcriptases), a thermo-labile polymerase, or a thermo-stable polymerase. In some embodiments, a polymerase can be any Family A or B type polymerase. Many types of Family A (e.g., *E. coli* Pol I), B (e.g., *E. coli* Pol II), C (e.g., *E. coli* Pol III), D (e.g., Euryarchaeotic Pol II), X (e.g., human Pol beta), and Y (e.g., *E. coli* UmuC/DinB and eukaryotic RAD30/xeroderma pigmentosum variants) polymerases are described in Rothwell and Watsman 2005 Advances in Protein Chemistry 71:401-440. In some embodiments, a polymerase can be a T3, T5, T7, or SP6 RNA polymerase.

In some embodiments, nucleic acid amplification reactions can be conducted with one type or a mixture of polymerases, recombinases and/or ligases. In some embodiments, nucleic acid amplification reactions can be conducted with a low fidelity or high fidelity polymerase.

In some embodiments, the reaction mixture can include a polymerase. The polymerase optionally has, or lacks, exonuclease activity. In some embodiments, the polymerase has 5' to 3' exonuclease activity, 3' to 5' exonuclease activity, or both. Optionally, the polymerase lacks any one or more of such exonuclease activities.

In some embodiments, the polymerase has strand displacing activity. Examples of useful strand-displacing polymerases include Bacteriophage 029 DNA polymerase and Bst DNA polymerase.

An exemplary polymerase is Bst DNA Polymerase (Exonuclease Minus), is a 67 kDa *Bacillus stearothermophilus* DNA Polymerase protein (large fragment), exemplified in accession number 2BDP_A, which has 5'-3' polymerase activity and strand displacement activity but lacks 3'-5' exonuclease activity. Other polymerases include Taq DNA polymerase I from *Thermus aquaticus* (exemplified by accession number 1TAQ), Eco DNA polymerase I from *Escherichia coli* (accession number P00582), Aea DNA polymerase I from *Aquifex aeohcus* (accession number 067779), or functional fragments or variants thereof, e.g., with at least 80%, 85%, 90%, 95% or 99% sequence identity at the nucleotide level.

In some embodiments, the DNA polymerase is a Bsu DNA polymerase (large fragment (NEB). Bsu DNA Polymerase I, Large Fragment retains the 5'→3' polymerase activity of the *Bacillus subtilis* DNA polymerase I (1), but lacks the 5'→3' exonuclease domain. In some embodiments, the Bsu DNA Polymerase large fragment lacks 3'→5' exonuclease activity. In some embodiments, Bsu DNA Polymerase large fragment has optimal activity at 37° C.

In one embodiment, the one or more enzymes capable of polymerization include a T5 or T7 DNA polymerase. In some embodiments, the one or more enzymes capable of polymerization include a T5 or T7 DNA polymerase having one or more amino acid mutations that reduce 3'-5' exonuclease activity. In some embodiments, the T5 or T7 DNA polymerase having one or more amino acid mutations that reduce 3'-5' exonuclease activity, does not contain an amino acid mutation that disrupts processivity of the T5 or T7 DNA polymerase. In some embodiments, the T5 or T7 DNA polymerase can include one or more amino acid mutations that eliminate detectable 3'-5' exonuclease activity; and wherein the one or more amino acid mutations do not disrupt processivity of the T5 or T7 DNA polymerase. In some embodiments, the reaction mixture comprises a Sau polymerase, T7 DNA polymerase with reduced 3' to 5' exonuclease activity, Bsu polymerase, or a combination thereof.

In some embodiments, the one or more enzymes capable of polymerization can include any suitable RNA polymerase. Suitable RNA polymerases include, without limitation, T3, T5, T7, and SP6 RNA polymerases.

In some embodiments, the disclosure relates generally to methods, as well as related compositions and kits, wherein the nucleic acid amplification includes a combination of recombinase-polymerase amplification (RPA) and the blocked primers under isothermal conditions. During amplification, the blocked primers are cleaved at the ribobase by a ribonuclease (RNase) to permit primer extension and template amplification. As is known, RNases are enzymes catalyzing hydrolysis of RNA into smaller components. The use of RNase H enzyme with the blocked primers of the invention provides advantages over methods of the art wherein their use reduces: 1) nonspecific primer tailing via blocked 3' end; and 2) non-templated primer dimer and nonspecific product formation, via specific RNase H cleavage on RNA/RNA duplex between primer and template strands.

In some embodiments, the compositions (e.g. reaction mixtures), methods, and kits, include a ribo-endonuclease that is active at appropriate temperatures for recombinase and polymerase activity and are compatible with those enzymes. The ribo-endonuclease used in the compositions, methods, and kits provided herein, can be an RNase H enzyme, which represents a family of non-sequence specific endonucleases that catalyze the cleavage of RNA via a hydrolytic mechanism wherein the enzyme cleaves the 3'-O—P bond of RNA in a DNA/RNA duplex substrate, provided that the RNase H enzyme is active at appropriate temperatures for recombinase and polymerase activity and is compatible with those enzymes.

The RNase H enzyme and its family of enzymes include two classes, type 1 and type 2 RNase H based on the difference in their amino acid sequence. Type 1 RNases H include prokaryotic and eukaryotic RNases H1 and retroviral RNase H. Type 2 RNases H include prokaryotic and eukaryotic RNases H2 and bacterial RNase H3. These RNases H exist in a monomeric form, except for eukaryotic RNases H2, which exist in a heterotrimeric form. All of these enzymes share the characteristic that they are able to cleave the RNA component of an RNA:DNA heteroduplex or within a DNA:DNA duplex containing RNA base(s) within one or both of the strands. The cleaved product yields a free 3'-OH for both classes of RNase H. RNase H1 requires more than a single RNA base within an RNA:DNA duplex for optimal activity, whereas RNase HII requires only a single RNA base in an RNA:DNA duplex.

In some embodiments, the RNase H enzyme can be any RNase H enzymes, provided that the enzyme retains sufficient activity at appropriate temperatures for recombinase and polymerase activity and is compatible with those enzymes. Therefore, the kits, compositions, and methods can include an RNase H enzyme that has higher activity at 37° C. than it has at least one of the following temperatures: 60° C., 65° C., 70° C., 75° C., or 80° C. For example, an RNase H enzyme used in the kits, compositions, and methods herein can have a higher activity at 37° C. than at 75° C. or have a higher activity at 37° C. than at 70° C. In some embodiments, the RNase H enzyme cleaves the oligonucleotide more efficiently at 37° C. than at 60° C. wherein cleavage of the ribobase present in the primer occurs at a temperature below 42° C. Accordingly, in illustrative examples of any of the embodiments provided herein, the RNase H enzyme is not a thermostable RNase H enzyme (i.e. the RNase H enzyme is other than a thermostable RNase H enzyme). In some embodiments, the RNase H enzyme that has significant activity at 20 to 42° C. The methods, compositions, and kits provided herein can include in illustrative examples, an RNase H enzyme that has significant activity at 37° C. In some embodiments, the RNase H has sufficient activity to carry out the claim methods at 37° C.

As indicated, the RNase H enzyme included in the methods, compositions, and kits provided herein can be any RNase H enzyme that is active at appropriate temperatures for recombinase and polymerase activity and is compatible with those enzymes. In some embodiments, RNase H enzyme comprises RNase H1 (commercially available from NEB, Inc.) or RNase H3. In alternative embodiments, RNase H enzyme does not comprise RNase H1 or RNase H3. An exemplary RNase H enzyme includes *E. coli* RNase HII (available for example from NEB, Inc. (product M0288)). In some embodiments, the endonuclease can be an RNase HII which cleaves a ribobase within a DNA duplex and leaves a 3' hydroxyl end, and temperatures at which it retains high activity are compatible with those of recombinase and recombinase associated proteins. In some embodiments, the RNase can be *E. coli* RNase H (available from NEB, Inc., for example product M0297) (products/m0297-rnase-h), which also cleaves a ribo-base when hybridized to DNA and leaves a 3'-hydroxyl end.

In some embodiments, the methods, as well as related compositions and kits include a blocked primer design with 2-5 consecutive ribobases. RNase H2 from *Pyrococcus abyssi* (P.a.), however, has low activity at room temperature with optimal activity around 70° C., a temperature above the range for the RPA methods. Accordingly, in some embodiments herein, a higher temperature is used for primer activation than used for amplification. For example, a primer amplification step at between 42° C. and 70° C., 45° C. and 70° C., or 50° C. and 70° C., or 50° C. and 65° C., or 60° C. and 70° C. can be performed, before an amplification at temperatures disclosed for the amplification methods herein, such as between 20° C. and 42° C. Some embodiments include performing primer activation and polymerization at two separate temperatures. RNase H2, such as RNase HII, can be used in such 2-step methods as well, since it is known to retain activity even at high temperatures.

The use of blocked primers are a potentially rate limiting step in the RPA methods (See FIG. 1), because the 3' domain and block must be removed before primer extension can proceed. To ensure the PRA reaction proceeds rapidly, in some embodiments an excess (i.e. non-limiting) amount of the RNase enzyme is used. One of skill understands an excess can be determined empirically, see Example 3 for example. However in embodiments between 2x, 3x, 4x, 5x, 6x, 7x, 8x, 9x, 10x, 11x, 12x, 13x, 14x, and 15x on the low end of the range, and 5x, 6x, 7x, 8x, 9x, 10x, 11x, 12x, 13x, 14x, 15x, 16x, 17x, 18x, 19x, 20x or 21x, on the high end of the range concentration of RNase H as compared to a minimally excess concentration, are used in the RPA methods. The exact concentration will depend on the starting concentration and other amplification parameters. One unit of RNase is defined as the amount of enzyme required to yield a fluorescence signal consistent with the nicking of 100 picomol of synthetic double-stranded DNA (dsDNA) substrate containing a single ribonucleotide near the quencher of a fluorophore/quencher pair in 30 minutes at 37° C. in 1× ThermoPol Buffer (NEB, Inc.). The dsDNA substrate can be a 26-mer present at 30 nM in a total reaction volume of 150 μl as indicated in the RNase HII product manual for RNase HII product M0288 of NEB, Inc., and as used to determine unit activity or RNase HII by NEB, Inc.

As described in Example 3, the RNase H enzyme concentration used in the RPA amplification reaction can be characterized as a "prohibiting", "limiting" or "excess" amount. Those concentrations are determined empirically and may be different for different blocked primer configurations, different concentration of starting DNA template or different reaction times or temperature. In some embodiments, an "excess" amount of RNase H enzyme when used with a V2 or V5 primer configuration is 20 U or more in a 50 μL reaction volume. In some embodiments, a "limiting" amount of RNase H enzyme is 5-10 U/50 μL, such as 5, 6, 7, 8, 9, 10 U/50 μL. In some embodiments, a "limiting" amount of RNase H enzyme is less than 20 U/50 μL, such as 19, 18, 17, 16, 15, 14, 13, 12, 11, or 10 U/50 μL. An "excess" amount of RNase H enzyme can be used in any of the embodiments of the invention provided herein. Such excess can be, for example, a concentration of equal to or greater than 20 U/50 μL (See FIGS. 8A and 8B).

In some embodiments, an *E. coli* RNase HII enzyme at a concentration from 2.5 U to 200 U/50 μL can be used. For example, an *E. coli* RNase HII enzyme present in the reaction mixture at a concentration from 5 to 150, 10 to 100, or 10 to 50 U/50 μL can be used. In some embodiments, greater than 10 U of RNase HII can be used.

In some embodiments, the RNase HII enzyme is present in the reaction mixture at an excess concentration. For example, the RNase HII enzyme can be an *E. coli* RNase HII enzyme and can be present at a concentration from 20-250 U/50 μL, 20-200 U/50 μL, 20-150 U/50 μL or 20-100 U/50 μL. As a non-limiting, specific example, the RNase H enzyme can be present in the reaction mixture at a concentration of 20, 25, 30, 40, 50, 75, 100, 150, 200, or 250 U/50 μL. The RNase H enzyme in certain examples of methods, kits, compositions, and reaction mixtures provided herein, is present at 2×, 3×, 4×, 5×, 10×, 20×, 40× or 50× an excessive concentration. For example, the RNase H enzyme can be an *E. coli* RNase HII enzyme present at 200, 250, 300, 400, 500, 750, 1000, 1500, 2000, or 2500 U/50 μL.

In some embodiments, the disclosure relates generally to methods, as well as related compositions and kits, wherein the nucleic acid amplification includes a reaction mixture which can include a diffusion limiting agent. The diffusion limiting agent can be any agent that is effective in preventing or slowing the diffusion of one or more of the polynucleotide templates and/or one or more of the amplification reaction products through the amplification reaction mixture.

In some embodiments, the reaction mixture can include a sieving agent. The sieving agent can be any agent that is effective in sieving one or more polynucleotides present in the amplification reaction mixture, such as for example amplification reaction products and/or polynucleotide templates. In some embodiments, the sieving agent restricts or slows the migration of polynucleotide amplification products through the reaction mixture.

Inclusion of a sieving agent may be advantageous when clonally amplifying two or more nucleic acid templates within a single continuous liquid phase of a reaction mixture. For example, the sieving agent can prevent or slow diffusion of templates, or amplified polynucleotides produced via replication of at least some portion of a template, within the reaction mixture, thus preventing the formation of polyclonal contaminants without requiring compartmentalization of the reaction mixture by physical means or encapsulation means (e.g., emulsions) during the amplification. Such methods of clonally amplifying templates within a single continuous liquid phase of a single reaction mixture without need for compartmentalization greatly reduces the cost, time and effort associated with generation of libraries amenable for high-throughput methods such as digital PCR, next generation sequencing, and the like.

In some embodiments, the average pore size of the sieving agent is such that movement of a target component within the reaction mixture (e.g., a polynucleotide) is selectively retarded or prevented. In one example, the sieving agent comprises any compound that can provide a matrix having a plurality of pores that are small enough to slow or retard the movement of a polynucleotide through a reaction mixture containing the sieving agent. Thus, a sieving agent can reduce Brownian motion of a polynucleotide.

In some embodiments, the amplification includes amplifying a plurality of different polynucleotide templates onto a plurality of different bead supports in the presence of a sieving agent, and recovering a percentage of substantially monoclonal bead supports, each such substantially monoclonal bead support include a bead support attached to a substantially monoclonal polynucleotide population. In some embodiments, the percentage of substantially monoclonal bead supports recovered is substantially greater than 5%, 10%, 15%, 20%, 25%, 30%, 35%, 40%, 50%, 55%, 60%, 65%, 70%, 75%, 89%, 90%, or 95% of total amplified bead supports (i.e., total bead supports including either polyclonal or monoclonal populations) recovered from the reaction mixture. In some embodiments, the percentage of substantially monoclonal bead supports recovered is substantially greater than the percentage of substantially monoclonal bead supports recovered following amplification in the absence of the sieving agent but under otherwise essentially similar or same amplification conditions.

In some embodiments, a sieving agent comprises a polymer compound. In some embodiments, a sieving agent comprises a cross-linked or a non-cross linked polymer compounds. By way of non-limiting examples, the sieving agent can include polysaccharides, polypeptides, organic polymers, etc.

In some embodiments, a sieving agent comprises linear or branched polymers. In some embodiments, a sieving agent comprises charged or neutral polymers.

In some embodiments, the sieving agent can include a blend of one or more polymers, each having an average molecular weight and viscosity.

In some embodiments, the sieving agent comprises a polymer having an average molecular weight of about 10,000-2,000,000, or about 12,000-95,000, or about 13,000-95,000.

In some embodiments, a sieving agent can exhibit an average viscosity range of about 5 centipoise to about 15,000 centipoise when dissolved in water at 2 weight percent measured at about 25° C., or about 10 centipoise to about 10,000 centipoise as a 2% aqueous solutions measured at about 25° C., or about 15 centipoise to about 5,000 centipoise as a 2% aqueous solution measured at about 25° C.

In some embodiments, a sieving agent comprises a viscosity average molecular weight ($M_v$) of about 25 to about 1,5000 k$M_v$, or about 75-1,000 k$M_v$, or about 85-800 k$M_v$. In some embodiments, the reaction mixture comprises a sieving agent at about 0.1 to about 20% weight per volume, or about 1-10% w/v, or about 2-5% w/v.

In some embodiments, a sieving agent comprises a polysaccharide polymer. In some embodiments, a sieving agent comprises a polymer of glucose or galactose. In some embodiments, a sieving agent comprises one or more polymers selected from the group consisting of: cellulose, dextran, starch, glycogen, agar, chitin, pectin or agarose. In some embodiments, the sieving agent comprises a glucopyranose polymer.

In some embodiments, the sieving agent includes a cellulose derivative, such as sodium carboxy methyl cellulose, sodium carboxymethyl 2-hydroxyethyl cellulose, methyl cellulose, hydroxyl ethyl cellulose, 2-hydroxypropyl cellulose, carboxy methyl cellulose, hydroxyl propyl cellulose, hydroxyethyl methyl cellulose, hydroxybutyl methyl cellulose, (hydroxypropyl)methyl cellulose or hydroxyethyl ethyl cellulose, or a mixture including any one or more of such polymers.

In some embodiments, the reaction mixture comprises a mixture of different sieving agents, for example, a mixture of different cellulose derivatives, starch, polyacrylamide, and the like.

In some embodiments, the reaction mixture can include a crowding agent.

In some embodiments, the reaction mixture includes both a crowding agent and a sieving agent.

In some embodiments, the reaction mixture includes at least one diffusion-reducing agent. In some embodiments, a diffusion-reducing agent comprises any compound that reduces migration of polynucleotides from a region of higher concentration to one having a lower concentration. In some embodiments, a diffusion reducing agent comprises any compound that reduces migration of any component of a nucleic acid amplification reaction irrespective of size.

It should be noted that the concepts of a sieving agent and a diffusion-reducing agent are not necessarily mutually exclusive; a sieving agent can frequently be effective in reducing diffusion of target compounds through a reaction mixture, whereas a diffusion reducing agent can frequently have a sieving effect on reaction components. In some embodiments, the same compound or reaction mixture additive can act both as a sieving agent and/or a diffusion reducing agent. Any of the sieving agents disclosed herein can in some embodiments be capable of acting as a diffusion reducing agent and vice versa.

In some embodiments, the diffusion reducing agent and/or sieving agent includes polyacrylamide, agar, agarose or a cellulose polymer such as hydroxyethyl cellulose (HEC), methyl-cellulose (MC) or carboxymethyl cellulose (CMC).

In some embodiments, the sieving agent and/or the diffusion reducing agent is included in the reaction mixture at concentrations of at least 1%, 2%, 5%, 10%, 15%, 20%, 25%, 30%, 40%, 50%, 74%, 90%, or 95% w/v (weight of agent per unit volume of reaction mixture).

In some embodiments, the reaction mixture includes at least one crowding agent. For example, a crowding agent can increase the concentration of one or more components in a nucleic acid amplification reaction by generating a crowded reaction environment. In some embodiments, the reaction mixture includes both a sieving agent and/or diffusion reagent and a crowding agent.

In some embodiments, the nucleic acid amplification methods comprise forming a reaction mixture by combining a nucleic acid template having a forward primer binding sequence and a reverse primer binding sequence, a polymerase, a recombinase, a single-stranded binding protein, a recombinase loading protein, a blocked forward primer, a blocked reverse primer, dNTPs, an RNase H enzyme, and a buffer comprising a divalent cation. In some embodiments, the forward primer binding sequence is complementary or identical to at least a portion of the blocked forward primer and the reverse primer binding sequence is complementary or identical to at least a portion of the blocked reverse primer.

In some embodiments, the blocked forward primer and the blocked reverse primer comprise a 5' domain and a 3' domain separated by a nucleotide comprising a ribobase, wherein the 5' domain is 10 to 40 nucleotides in length and the 3' domain is 10 to 25 nucleotides in length. In some embodiments, the blocked forward primer and the blocked reverse primer comprise a 5' domain and a 3' domain separated by a nucleotide comprising a ribobase, wherein the 5' domain is 10 to 100 nucleotides in length and the 3' domain is 10 to 30 nucleotides in length.

In some embodiments, the reaction mixture further comprises a recombinase accessory protein. In some embodiments, the recombinase accessory protein is a single-stranded binding protein and/or a recombinase loading protein.

In some embodiments, the reaction mixture comprises a blocked primer wherein 5' domain is 15 to 30 nucleotides in length. In some embodiments, the 5' domain of the blocked primers is 15 to 50 nucleotides in length. In some embodiments, the reaction mixture includes a blocked primer wherein the 3' domain is 14 to 25 nucleotides in length. In some embodiments, the 3' domain is 15 to 25 nucleotides in length. In some embodiments, the 5' domain can be at least 15 nucleotides and the 3' domain can be at least 10 nucleotides, wherein the length of the primer does not exceed 100, 90, 80, 75, 70, 60, or 50 nucleotides. In some embodiments, a 3' nucleotide of the 3' domain of the forward primer is mismatched to the forward primer binding sequence.

In some embodiments, the ribobase separating the 5' domain and the 3' domain of the blocked primer comprises rU, rG or rA. In some embodiments, the ribobase separating the 5' domain and the 3' domain of the blocked primer comprises rC. In some embodiments, the 3' domain of the blocked primers is 14 to 20 nucleotides in length and the ribobase is rU, rG, rC or rA.

In some embodiments, the reaction mixture comprises a recombinase accessory protein that is uvsY. In some embodiments, the reaction mixture comprises a recombinase selected from the group consisting of uvsX, RecA, RadA, RadB, Rad 51, a homologue thereof, a functional analog thereof and a combination thereof. In some embodiments, the reaction mixture comprises uvsY recombinase accessory protein and uvsX recombinase.

In some embodiments, the reaction mixture comprises RNase H enzyme that is RNase HII. In some embodiments, the RNase H enzyme is present at a concentration from 20 U to 100 U/50 μL. In some embodiments, the RNase H enzyme is present at a concentration from 40 to 90 U/50 μL.

In some embodiments, the nucleic acid template is a member of a nucleic acid library comprising a population of nucleic acid templates each comprising a forward primer binding sequence, and wherein the blocked forward primer is a blocked universal forward primer that binds the universal forward primer binding sequence. In some embodiments, the nucleic acid templates each comprises a reverse universal primer binding sequence and wherein the blocked reverse primer is a blocked universal reverse primer that binds the universal reverse primer binding sequence.

In some embodiments, either or both of the blocked forward primer and the blocked reverse primer are immobilized on a solid support. In some embodiments, the solid support is a bead.

In some embodiments, the nucleic acid amplification methods comprise forming a reaction mixture by combining at least two different polynucleotide templates comprising both a first primer binding sequence and a second primer binding sequence, a recombinase, a recombinase accessory protein, a polymerase, a first blocked universal primer, a second blocked universal primer, dNTPs, an RNase H enzyme, and a buffer. The reaction mixture is in contact with a support having the first blocked universal primer bound thereto, wherein the first primer binding sequence is complementary or identical to at least a portion of the first blocked universal primer and the second primer binding sequence is complementary or identical to at least a portion of the second blocked universal primer.

In some embodiments, at least two substantially monoclonal nucleic acid populations are formed by using the polymerase to amplify each of said at least two different polynucleotide templates onto different sites on the solid support under substantially isothermal conditions.

In some embodiments, the second blocked universal primer is in solution (e.g., soluble primers). In some embodiments, the second blocked universal primer is immobilized on the support.

In some embodiments, the reaction mixture and the at least two substantially monoclonal nucleic acid populations are formed in the same single continuous liquid phase. In some embodiments, the reaction mixture and the at least two substantially monoclonal nucleic acid populations are formed in a water-in-oil emulsion.

In some embodiments, the at least two different polynucleotide templates are members of a polynucleotide library, wherein each member of the polynucleotide library comprises the first primer binding sequence and the second primer binding sequence. In some embodiments, nucleic acids of the at least two substantially monoclonal nucleic acid populations are sequenced.

In some embodiments, the first blocked universal primer and the second blocked universal primer comprise a 5' domain and a 3' domain separated by a nucleotide comprising a ribobase, wherein the 5' domain is 10 to 40 nucleotides in length and the 3' domain is 10 to 25 nucleotides in length. In some embodiments, the reaction mixture comprises a first and second blocked primer wherein the 5' domain is 15 to 30 nucleotides in length. In some embodiments, the 5' domain of the blocked primers is 15 to 50 nucleotides in length. In some embodiments, the reaction mixture comprises a blocked primer wherein the 3' domain is 14 to 25 nucleotides in length. In some embodiments, the 3' domain is 15 to 25 nucleotides in length. In some embodiments, a 3' nucleotide of the 3' domain of the first primer is mismatched to the first primer binding sequence.

In some embodiments, the ribobase separating the 5' domain and the 3' domain of the blocked primer comprises rU, rG or rA. In embodiments the ribobase separating the 5' domain and the 3' domain of the blocked primer comprises rC. In some embodiments, the 3' domain of the blocked primers is 14 to 20 nucleotides in length and the ribobase is rU, rG, rC or rA.

In some embodiments, the reaction mixture comprises a recombinase accessory protein that is uvsY. In some embodiments, the reaction mixture comprises a recombinase selected from the group consisting of uvsX, RecA, RadA, RadB, Rad 51, a homologue thereof, a functional analog thereof and a combination thereof. In some embodiments, the reaction mixture comprises uvsY recombinase accessory protein and uvsX recombinase.

In some embodiments, the reaction mixture comprises RNase H enzyme that is RNase HII. In some embodiments, the RNase H enzyme is present at a concentration from 20 U to 100 U/50 µL. In some embodiments, the RNase H enzyme is present at a concentration from 40 to 90 U/50 µL.

In some embodiments, the disclosure relates generally to methods, as well as related compositions and kits, wherein the nucleic acid amplification includes the amplification reaction mixture which can include one or more solid or semi-solid supports. In some embodiments, at least one of the supports can include one or more instances of a first blocked primer including a first primer sequence. As used herein, the blocked primers refer to those described above containing a 5' domain, at least one ribobase, a 3' domain and a blocking group. The appropriate length for the 5' and 3' domain the primers are described in detail above, for example the 3' domain has a length of at least 10 nucleotides such as 10 to 30 nucleotides. In the section that follows, the primers that may be attached to a support or surface are those blocked primers described herein. For example, a forward or reverse blocked primer is attached to a solid support via the 5' end of the primer. See FIG. 11 for exemplary blocked primers for use on a solid support.

In some embodiments, at least one polynucleotide template in the reaction mixture includes a first primer binding sequence. The first primer binding sequence can be substantially identical or substantially complementary to the first blocked primer sequence. In some embodiments, at least one, some or all of the supports include a plurality of first blocked primers that are substantially identical to each other. In some embodiments, all of the blocked primers on the supports are substantially identical to each other, or all include a substantially identical first primer sequence.

In some embodiments, at least one of the supports includes two or more different blocked primers attached thereto. For example, the at least one support can include at least one instance of the first blocked primer and at least one instance of a second blocked primer.

In some embodiments, the aqueous phase of the reaction mixture includes a plurality of supports, at least two supports of the plurality being attached to blocked primers including a first priming sequence. In some embodiments, the reaction mixture includes two or more different polynucleotide templates having a first primer binding sequence.

Alternatively, in some embodiments, the reaction mixture does not include any supports. In some embodiments, the at least two different polynucleotide templates are amplified directly onto a surface of the site or reaction chamber of the array. In some embodiments, the reaction chambers are arranged in an array on a support and the reaction chambers are used to conduct sequencing reactions. In some embodiments, the reaction chambers are arranged in an array on a sequencing support.

In some embodiments, methods for nucleic acid amplification comprise one or more surfaces. In some embodiments, a surface can be attached with a plurality of first primers, the first primers of the plurality sharing a common first primer sequence.

In some embodiments, a surface can be an outer or top-most layer or boundary of an object. In some embodiments, a surface can be interior to the boundary of an object.

In some embodiments, the reaction mixture includes multiple different surfaces, for example, the reaction mixture can include a plurality of beads (such as particles, nanoparticles, microparticles, and the like) and at least two different polynucleotide templates can be clonally amplified onto different surfaces, thereby forming at least two different surfaces, each of which is attached to an amplicon. In some embodiments, the reaction mixture includes a signal surface (for example, the surface of a slide or array of reaction chambers) and at least two different polynucleotide templates are amplified onto two different regions or locations on the surface, thereby forming a single surface attached to two or more amplicons.

In some embodiments, a surface can be porous, semi-porous or non-porous. In some embodiments, a surface can be a planar surface, as well as concave, convex, or any combination thereof. In some embodiments, a surface can be a bead, particle, microparticle, sphere, filter, flowcell, well, groove, channel reservoir, gel or inner wall of a capillary. In some embodiments, a surface includes the inner walls of a capillary, a channel, a well, groove, channel, reservoir. In some embodiments, a surface can include texture (e.g., etched, cavitated, pores, three-dimensional scaffolds or bumps).

In some embodiments, a surface can be magnetic or paramagnetic bead (e.g., magnetic or paramagnetic nanoparticles or microparticles). In some embodiments, paramagnetic microparticles can be paramagnetic beads attached with streptavidin (e.g., Dynabeads™ M-270 from Invitrogen, Carlsbad, CA). Particles can have an iron core, or comprise a hydrogel or agarose (e.g., Sepharose™).

In some embodiments, the surface can have immobilized thereon, a plurality of an RNase-cleavable first blocked primer. See Example 5. A surface can be coated with an acrylamide, carboxylic or amine compound for attaching a nucleic acid (e.g., a first primer). In some embodiments, an amino-modified nucleic acid (e.g., primer) can be attached to a surface that is coated with a carboxylic acid. In some embodiments, an amino-modified nucleic acid can be reacted with EDC (or EDAC) for attachment to a carboxylic acid coated surface (with or without NHS). A first blocked primer can be immobilized to an acrylamide compound coating on a surface. Particles can be coated with an avidin-like compound (e.g., streptavidin) for binding biotinylated nucleic acids.

In some embodiments, the surface comprises the surface of a bead. In some embodiments, a bead comprises a polymer material. For example, a bead comprises a gel, hydrogel or acrylamide polymers. A bead can be porous. Particles can have cavitation or pores, or can include three-dimensional scaffolds. In some embodiments, particles can be Ion Sphere™ particles.

In some embodiments, the disclosed methods (as well as related compositions, systems and kits) include immobilizing one or more nucleic acid templates onto one or more supports. Nucleic acids may be immobilized on the solid support by any method including but not limited to physical adsorption, by ionic or covalent bond formation, or combinations thereof. A solid support may include a polymeric, a glass, or a metallic material. Examples of solid supports include a membrane, a planar surface, a microtiter plate, a bead, a filter, a test strip, a slide, a cover slip, and a test tube. A solid support means any solid phase material upon which an oligomer is synthesized, attached, ligated or otherwise immobilized. A support can optionally comprise a "resin", "phase", "surface" and "support". A support may be composed of organic polymers such as polystyrene, polyethylene, polypropylene, polyfluoroethylene, polyethyleneoxy, and polyacrylamide, as well as co-polymers and grafts thereof. A support may also be inorganic, such as glass, silica, controlled-pore-glass (CPG), or reverse-phase silica. The configuration of a support may be in the form of beads, spheres, particles, granules, a gel, or a surface. Surfaces may be planar, substantially planar, or non-planar. Supports may be porous or non-porous, and may have swelling or non-swelling characteristics. A support can be shaped to comprise one or more wells, depressions or other containers, vessels, features or locations. A plurality of supports may be configured in an array at various locations. A support is optionally addressable (e.g., for robotic delivery of reagents), or by detection means including scanning by laser illumination and confocal or deflective light gathering. An amplification support (e.g., a bead) can be placed within or on another support (e.g., within a well of a second support).

In some embodiments, the solid support is a "microparticle," "bead," "microbead," etc., (optionally but not necessarily spherical in shape) having a smallest cross-sectional length (e.g., diameter) of 50 microns or less, preferably 10 microns or less, 3 microns or less, approximately 1 micron or less, approximately 0.5 microns or less, e.g., approximately 0.1, 0.2, 0.3, or 0.4 microns, or smaller (e.g., under 1 nanometer, about 1-10 nanometer, about 10-100 nanometers, or about 100-500 nanometers). Microparticles (e.g., Dynabeads from Dynal, Oslo, Norway) may be made of a variety of inorganic or organic materials including, but not limited to, glass (e.g., controlled pore glass), silica, zirconia, cross-linked polystyrene, polyacrylate, polymehtymethacrylate, titanium dioxide, latex, polystyrene, etc. Magnetization can facilitate collection and concentration of the microparticle-attached reagents (e.g., polynucleotides or ligases) after amplification, and can also facilitate additional steps (e.g., washes, reagent removal, etc.). In some embodiments of the invention a population of microparticles having different shapes sizes and/or colors can be used. The microparticles can optionally be encoded, e.g., with quantum dots such that each microparticle can be individually or uniquely identified.

In some embodiments, a bead surface can be functionalized for attaching a plurality of a first blocked primer. In some embodiments, a bead can be any size that can fit into a reaction chamber. For example, one bead can fit in a reaction chamber. In some embodiments more than one bead can fit in a reaction chamber. In some embodiments, the smallest cross-sectional length of a bead (e.g., diameter) can be about 50 microns or less, or about 10 microns or less, or about 3 microns or less, approximately 1 micron or less, approximately 0.5 microns or less, e.g., approximately 0.1, 0.2, 0.3, or 0.4 microns, or smaller (e.g., under 1 nanometer, about 1-10 nanometer, about 10-100 nanometers, or about 100-500 nanometers). In some embodiments, a bead can be attached with a plurality of one or more different blocked primer sequences. In some embodiments, a bead can be attached with a plurality of one blocked primer sequence, or can be attached a plurality of two or more different blocked primer sequences. In some embodiments, a bead can be attached with a plurality of at least 1,000 primers, or about 1,000-10,000 primers, or about, 10,000-50,000 primers, or about 50,000-75,000 primers, or about 75,000-100,000 primers, or more. In some embodiments, the disclosure relates generally to methods, as well as related compositions and kits, wherein the nucleic acid amplification includes the reaction mixtures discussed in the context of methods provided herein themselves form embodiments of the invention. In some embodiments, the compositions that include a recombinase, a polymerase suitable for RPA, and an RNase H enzyme that is active at temperatures at which the recombinase and polymerase are active, and is compatible with those enzymes. In some embodiments, the compositions can further include a single stranded binding protein and/or a recombinase loading protein. The recombinase and polymerase are typically present at effective concentrations for recombinase polymerase amplification, or at higher concentrations such that they can be combined with other reaction components into a final blocked primer-RPA reaction mixture. RNase is present at an effective concentration, such as a limiting and/especially an excess concentration, as disclosed herein, or 2×, 3×, 4×, 5×, or 10× such concentrations. The RNase can be any of the RNases discussed herein, including in illustrative examples, *E. coli* RNase HII.

In some embodiments, the compositions can further include other components of an RPA and/or RNase reaction. For example, the compositions can include dNTPs and a buffer. In addition, the composition can include a blocked forward primer and a blocked reverse primer. As a non-limiting example, the composition can include a recombinase, a polymerase, an RNase H enzyme that is other than a thermostable RNase H, a nucleic acid template, uvsX recombinase, uvsY recombinase loading protein, gp32 protein, Sau DNA polymerase, dNTPs, ATP, phosphocreatine and creatine kinase. In some embodiments, the composition can be in liquid form, or it can be in a solid form, such as a dried-down pellet form that can be rehydrated. Furthermore, components for compositions provided herein, can be split up such that any combination of the components can be in a pellet or liquid form, and one or more combinations of the rest of the components can be in one or more separate pellet or liquid forms. Such combinations can form kits that include at least two of such combinations. For example, a kit of the invention can include a pellet that includes all the reaction mixture components provided herein except for the RNase enzyme, which can be provided in a separate pellet or liquid in the kit.

In some embodiments, provided herein are compositions and kits including at least one blocked primer of the invention that includes a ribonucleotide as disclosed in detail herein. The compositions and kits can further include a second blocked primer or a standard primer. In some embodiments, the compositions and kits include a pair of primers (forward and reverse) wherein at least one is a blocked primer of the invention.

In some embodiments, the composition includes a reaction mixture having at least a blocked primer that includes a ribonucleotide as discussed in detail herein, and a recombinase. In some embodiments, the composition further includes amplification reagents including template nucleic acid, polymerase, RNase H, and/or accessory proteins. The reaction mixture for an amplification reaction typically includes a source of nucleotides, or analogs thereof, that is used by the polymerase as substrates for an extension reaction.

In some embodiments, a composition comprises nucleic acid template, a polymerase, a recombinase, a blocked forward primer, a blocked reverse primer, dNTPs, an RNase H enzyme, and a buffer. In some embodiments, the composition comprises a nucleic acid template, blocked forward primer, a blocked reverse primer, uvsX recombinase, uvsY recombinase loading protein, gp32 protein, Sau DNA polymerase, dNTPs, ATP, phosphocreatine and creatine kinase.

In some embodiments, the blocked forward primer and/or the blocked reverse primer in compositions, reaction mixtures, and kits of the invention can include any of the blocked primers disclosed herein. For example, the blocked forward primer and/or the blocked reverse primer can include a 5' domain and a 3' domain separated by a nucleotide comprising a ribobase, wherein the 5' domain is 10 to 40 nucleotides in length and the 3' domain is 11 to 25 nucleotides in length. In some embodiments, the composition comprises a forward and reverse blocked primer wherein the 5' domain is 15 to 30 nucleotides in length. In some embodiments, the 5' domain of the blocked primers is 15 to 50 nucleotides in length. In some embodiments, the composition comprises a blocked primer wherein the 3' domain is 14 to 25 nucleotides in length. In some embodiments, the 3' domain is 15 to 25 nucleotides in length. In some embodiments, a 3' nucleotide of the 3' domain of the forward primer is mismatched to the forward primer binding sequence.

In some embodiments, a composition of the invention comprises at least two different polynucleotide templates comprising both a first primer binding sequence and a second primer binding sequence, a recombinase, a recombinase accessory protein, a polymerase, a first blocked universal primer, a second blocked universal primer, dNTPs, an RNase H enzyme, and a buffer. In some embodiments, the composition further comprises a support. In some embodiments, the support is a bead. In further embodiments, the first blocked universal primer is attached to the bead support.

In some embodiments, the composition includes at least two different polynucleotide templates comprising both a first primer binding sequence and a second primer binding sequence, uvsX recombinase, uvsY recombinase loading protein, gp32 protein, Sau DNA polymerase, APT, phosphocreatine, creatine kinase, a first blocked universal primer attached to a bead support, a second blocked universal primer, an RNase H enzyme, and a buffer.

In some embodiments, the first blocked universal primer and the second blocked universal primer comprise a 5' domain and a 3' domain separated by a nucleotide comprising a ribobase, wherein the 5' domain is 10 to 40 nucleotides in length and the 3' domain is 10 to 25 nucleotides in length. In some embodiments, the composition comprises a first and second blocked primer wherein the 5' domain is 15 to 30 nucleotides in length. In some embodiments, the 5' domain of the blocked primers is 15 to 50 nucleotides in length. In some embodiments, the composition comprises a blocked primer wherein the 3' domain is 14 to 25 nucleotides in length. In some embodiments, the 3' domain is 15 to 25 nucleotides in length. In some embodiments, a 3' nucleotide of the 3' domain of the first primer is mismatched to the first primer binding sequence.

In some embodiments, compositions are also amendable to kit format wherein the primers, and amplification may be in the same contain, separate contains and in liquid or dehydrated form. The kit may comprise instructions for performing the RPA methods for amplification of nucleic acid template including clonal amplification for downstream sequencing methods. In one embodiment, the kit provides instructions for nucleic acid sequencing preparation.

In some embodiments, provided herein is a kit that includes at least two containers at least one of which includes a blocked, at least one of which includes a recombinase and at least one of which includes an RNase H. The recombinase, RNase H and the blocked can be in the same or different tubes.

In some embodiments, at least one blocked primer can be attached to a support. In some embodiments, the kit comprises at least one blocked primer attached to a bead support.

In some embodiments, the container comprising the recombinase further comprises one or more amplification reagents including a recombinase accessory protein, a polymerase, dNTPs, an RNase H enzyme, and a buffer. In some embodiments the kit comprises one or more containers comprising uvsX recombinase, uvsY recombinase loading protein, gp32 protein, Sau DNA polymerase, dNTPs, RNase H, ATP, phosphocreatine and creatine kinase.

In some embodiments, the kit comprises a blocked forward primer and a blocked reverse primer comprising a 5' domain and a 3' domain separated by a nucleotide comprising a ribobase, wherein the 5' domain is 10 to 40 nucleotides in length and the 3' domain is 10 to 25 nucleotides in length. In some embodiments, the kit comprises a forward and reverse blocked primer wherein the 5' domain is 15 to 30 nucleotides in length. In some embodiments, the 5' domain of the blocked primers is 15 to 50 nucleotides in length. In some embodiments, the kit comprises a blocked primer wherein the 3' domain is 14 to 25 nucleotides in length. In some embodiments, the 3' domain is 15 to 25 nucleotides in length. In some embodiments, a 3' nucleotide of the 3' domain of the forward primer is mismatched to the forward primer binding sequence.

In some embodiments, the kit the first blocked universal primer and the second blocked universal primer comprise a 5' domain and a 3' domain separated by a nucleotide comprising a ribobase, wherein the 5' domain is 10 to 40 nucleotides in length and the 3' domain is 10 to 25 nucleotides in length. In some embodiments, the composition comprises a first and second blocked primer wherein the 5' domain is 15 to 30 nucleotides in length. In some embodiments, the 5' domain of the blocked primers is 15 to 50 nucleotides in length. In some embodiments, the kit comprises a blocked primer wherein the 3' domain is 14 to 25 nucleotides in length. In some embodiments, the 3' domain is 15 to 25 nucleotides in length. In some embodiments, a 3' nucleotide of the 3' domain of the first primer is mismatched to the first primer binding sequence.

In some embodiments, the kit comprises a first blocked universal primer attached to a bead support. In some embodiments, the kit further comprises instructions for clonal amplification of two or nucleic acid templates to be used for nucleic acid sequencing.

In some embodiments, the disclosure relates generally to methods, as well as related compositions, kits, systems and apparatuses, for nucleic acid amplification, comprising amplifying a nucleic acid template to produce an amplicon using the RNase-cleavable blocked primers disclosed herein. In some embodiments, the amplicon is a substantially monoclonal population of polynucleotides. Monoclonality can be desirable in nucleic acid assays because the different characteristics of the diverse polynucleotides within a polyclonal population can complicate the interpretation of assay data. One example involves nucleic acid sequencing applications, in which the presence of polyclonal populations can complicate the interpretation of sequencing data; however, with many sequencing systems are not sensitive enough to detect nucleotide sequence data from a single polynucleotide template, thus requiring clonal amplification of templates prior to sequencing.

In some embodiments, the amplification methods can be employed to clonally amplify two or more different nucleic acid templates, optionally using and within the same reaction mixture, to produce at least two substantially monoclonal, and in some embodiments, monoclonal nucleic acid populations. Optionally, at least one of the substantially monoclonal populations is formed via amplification of a single polynucleotide template.

In some embodiments, the reaction mixture can be incubated under substantially isothermal amplification conditions thereby amplifying the nucleic acid template(s). In some embodiments, the isothermal conditions are typically between 20° C. to 50° C., in some embodiments 20° C. to 45° C., in some embodiments, 20° C. to 45° C., in other embodiments, 25° C. to 40° C., and still other embodiments 25° C. to 37° C. for 2 to 240 minutes. In some embodiments, the temperature is between 30° C. and 42° C. In some embodiments, the reaction mixture is not exposed to a temperature above 40° C., or above 41° C., or above 42° C., or above 43° C., or above 45° C. or not exposed to a temperature above 50° C. In some embodiments, the reaction mixture is not exposed to hot start conditions. A rate limiting enzyme may be RNase H, wherein a high concentration or excess (i.e. non-limiting) amount of the endonuclease ensures the amplification reaction proceeds based on the kinetics of the polymerase. See Example 3.

As illustrated in FIG. 1, once blocked primers hybridize to complementary template sequences, RNase H enzyme is activated, cleaving the ribonucleotide linkage in the blocked primer present in duplex DNA. The 3' domain comprising the blocking group dissociates, liberating the blocking group which blocks amplification, creating a free 3'-hydroxyl which is now capable of primer extension. Alternatively, RNase nicks the DNA, and the 3' domain comprising the blocking group is displaced by the 5' domain primer extension. RNase H enzyme used here is active at between about 20° C. to 45° C., the temperature range for the RPA amplification methods. One drawback to the use of recombinase amplification methods is that primer/primer hybrids are typically stable at these temperatures, leading to primer artifact amplification. However, the use of the blocked primers comprising a ribonuclease cleavage location reduces or eliminates primer dimer product amplification. See Example 2.

In some embodiments, the amplification is typically performed under substantially isothermal amplification conditions. The substantially isothermal temperature can be between 20, 21, 22, 23, 24, 25, 30, 35 or 40 on the low end of the range, and 21, 22, 23, 24, 25, 26, 30, 35, 40 or 45 on the high end of the range. In some embodiments, the temperature is between 20° C. and 45° C. In some embodiments, the temperature is between 35° C. and 45° C. In some embodiments, the temperature is 37° C.

In some embodiments, an isothermal RPA nucleic acid amplification reaction can be conducted at about 15-25° C., or about 25-35° C., or about 35-40° C., or about 35-42° C., or about 40-45° C., or about 45-50° C., or about 50-55° C., or about 55-60° C. However, it is understood the enzymes used at these temperatures will need to be optimized in combination and may require changes in the enzyme, for example the DNA polymerase used, Bst instead of Bsu, or the RNase H enzyme, such as RNase H2 instead of RNase HII.

In some embodiments, any of the nucleic acid amplification methods disclosed herein can be conducted, or can include steps that are conducted, under isothermal or substantially isothermal amplification conditions. In some embodiments isothermal amplification conditions comprise a nucleic acid amplification reaction subjected to a temperature variation which is constrained within a limited range during at least some portion of the amplification (or the entire amplification process), including for example a temperature variation is equal or less than about 20° C., or about 10° C., or about 5° C., or about 1-5° C., or about 0.1-1° C., or less than about 0.1° C., or, for example a temperature variation is equal or less than 20° C., or 10° C., or 5° C., or 1-5° C., or 0.1-1° C., or less than 0.1° C.

The amplification can be carried out for 2 minutes to 240 minutes, thereby amplifying the nucleic acid template. In some embodiments, the reaction time is between 2, 3, 4, 5, 6, 7, 8, 9, 10, 11, 12, 13, 14, 15, 16, 17, 18, 19, 20, 25, 30, 25, 40, 50, 60, 70, 80, 90, 100, 120, 140, 160, 180, 200 or 220 minutes on the low end of the range, and 3, 4, 5, 6, 7, 8, 9, 10, 11, 12, 13, 14, 15, 16, 17, 18, 19, 20, 25, 26, 27, 28, 29, 30, 25, 40, 50, 60, 70, 80, 90, 100, 120, 140, 160, 180, 200, 220 or 240 minutes on the high end of the range. In some embodiments, the reaction mixture is incubated to generate an amplified template for at least 5 minutes, wherein reaction time is between 5, 6, 7, 8, 9, 10, 11, 12, 13, 14, 15, 16, 17, 18, 19, 20, 25, 30, 25, 40, 50, 60, 70, 80, 90, 100, 120, 140, 160, 180, 200 or 220 minutes on the low end of the range, and 6, 7, 8, 9, 10, 11, 12, 13, 14, 15, 16, 17, 18, 19, 20, 25, 26, 27, 28, 29, 30, 25, 40, 50, 60, 70, 80, 90, 100, 120, 140, 160, 180, 200, 220 or 240 minutes on the high end of the range.

In some embodiments, the reaction mixture is incubated from 5 to 60 minutes. In some embodiments, the amplifying time is from 15 to 60 minutes. In some embodiments, the amplifying time is from 15 to 45 minutes. In some embodiments, the reaction mixture is incubated for 30 minutes to generate an amplified template sequence. In some embodiments, the reaction mixture is incubated for 50 minutes to generate an amplified template sequence.

In some embodiments, an isothermal nucleic acid amplification reaction can be conducted for about 2, 5, 10, 15, 20, 30, 40, 50, 60 or 120 minutes.

In some embodiments, the reaction mixture is formed by combining a nucleic acid template having a forward primer binding sequence and a reverse primer binding sequence, with the following optional reagents: a polymerase, a recombinase, a single-stranded binding protein, a recombinase loading protein, a blocked forward primer, a blocked reverse primer, dNTPs, ATP, phosphocreatine and creatine kinase, an RNase H enzyme, and a buffer, and wherein a divalent cation, such as $MgCl_2$ or $Mg(OAc)_2$ can be added to start the reaction. In some embodiments, the buffer may include a crowding agent, such as PEG, Tris buffer and a potassium acetate salt. The forward primer binding sequence is complementary or identical to at least a portion of the blocked forward primer and the reverse primer binding sequence is complementary or identical to at least a portion of the blocked reverse primer. The reaction mixture is incubated under substantially isothermal amplification conditions, for example between 35° C. and 45° C. for 15 to 60 minutes, thereby amplifying the nucleic acid template.

In some embodiments, the blocked forward primer and the blocked reverse primer comprise a 5' domain and a 3' domain separated by a nucleotide comprising a ribobase, wherein the 5' domain is 10 to 40 nucleotides in length and the 3' domain is 11 to 25 nucleotides in length. The forward and reverse primers, in some embodiments, bind in opposite directions to different strands of a double-stranded template, such that the region between the primer binding sites of the template is amplified, as is known for pairs of amplification primers.

In some embodiments, amplification methods and associated compositions provided herein that include improved ribobase-containing primers, can be used in a nucleic acid sequencing workflow, especially a high throughput nucleic acid sequencing workflow. In some embodiments, the reaction mixture is formed by combining at least two different polynucleotide templates comprising both a first primer binding sequence and a second primer binding sequence, a recombinase, a recombinase accessory protein, a polymerase, a first blocked universal primer, a second optionally blocked universal primer, dNTPs, an RNase H enzyme, and a buffer. In some embodiments, the reaction mixture is in contact with a support having the first blocked universal primer bound thereto, wherein the first primer binding sequence is complementary or identical to at least a portion of the first blocked universal primer and the second primer binding sequence is complementary or identical to at least a portion of the second optionally blocked universal primer.

The nucleic acid amplification methods result in the formation of at least two substantially monoclonal nucleic acid populations by using the polymerase to amplify each of the at least two different polynucleotide templates onto different sites on the solid support, within the same reaction mixture of step (a) under substantially isothermal conditions.

In some embodiments, the two or more different nucleic acid templates are amplified simultaneously and/or in parallel.

In some embodiments, the second optionally blocked universal primer is in solution (e.g., soluble primers). In some embodiments, the second optionally blocked universal primer is immobilized on the support.

In some embodiments, the reaction mixture and the at least two substantially monoclonal nucleic acid populations are formed in the same single continuous liquid phase. In some embodiments, the reaction mixture and the at least two substantially monoclonal nucleic acid populations are formed in a water-in-oil emulsion.

In some embodiments, the at least two different polynucleotide templates are members of a polynucleotide library, wherein each member of the polynucleotide library comprises the first primer binding sequence and the second primer binding sequence. In some embodiments, nucleic acids of the at least two substantially monoclonal nucleic acid populations are sequenced.

In some embodiments, the first blocked universal primer and the second optionally blocked universal primer when it is present in a blocked configuration comprise a 5' domain and a 3' domain separated by a nucleotide comprising a ribobase, wherein the 5' domain is 10 to 40 nucleotides in length and the 3' domain is 10 to 25 nucleotides in length. In some embodiments, embodiments, the reaction mixture comprises a first and second blocked primer wherein the 5' domain is 15 to 30 nucleotides in length. In some embodiments, the 5' domain of the blocked primers is 15 to 50 nucleotides in length. In some embodiments, the reaction mixture comprises a blocked primer wherein the 3' domain is 14 to 25 nucleotides in length. In some embodiments, the 3' domain is 15 to 25 nucleotides in length. In some embodiments, a 3' nucleotide of the 3' domain of the forward primer is mismatched to the forward primer binding sequence.

In some embodiments, the ribobase separating the 5' domain and the 3' domain of the blocked primer comprises rU, rG or rA. In some embodiments, the ribobase separating the 5' domain and the 3' domain of the blocked primer comprises rC. In some embodiments, the 3' domain of the blocked primers is 14 to 20 nucleotides in length and the ribobase is rU, rG, rC or rA.

In some embodiments, the reaction mixture used in the methods provided herein is a composition section provided herein. The reaction mixture can include components such as, for example, a recombinase accessory protein such as uvsY at concentrations provided herein. For example, the uvsY can be present, at 20 ng/ul to 100 ng/ul. In some embodiments, the reaction mixture comprises a recombinase selected from the group consisting of uvsX, RecA, RadA, RadB, Rad 51, a homologue thereof, a functional analog thereof and a combination thereof. The UvsX protein can be present, for example, at 50-250 ng/ul or 100-200 ng/ul. In some embodiments, the reaction mixture comprises uvsY recombinase accessory protein and uvsX recombinase.

In some embodiments, the reaction mixture comprises an RNase H enzyme according to any of the teachings provided in the RNase section herein. For example, the RNase H enzyme can be E. coli RNase HII. In some embodiments, the RNase H enzyme is present at a limiting or especially an excess concentration as provided herein. Useful concentrations for such RNase H enzyme is provided elsewhere herein.

In some embodiments, the disclosure relates generally to methods (as well as related compositions, systems and kits) for nucleic acid synthesis, comprising: providing at least two double stranded nucleic acid templates in a reaction mixture; and forming at least two substantially monoclonal nucleic acid populations by clonally amplifying the at least two double stranded nucleic acid templates according to any of the methods described herein.

In some embodiments, clonally amplifying optionally includes forming a reaction mixture. The reaction mixture can include a continuous liquid phase. In some embodiments, the continuous liquid phase includes a single continuous aqueous phase. The liquid phase can include two or more polynucleotide templates, which can optionally have the same nucleotide sequence, or can have nucleotide sequences that are different from each other. In some embodiments, at least one of the two or more polynucleotide templates can include at least one nucleic acid sequence that is substantially non-identical, or substantially non-complementary, to at least one other polynucleotide template within the reaction mixture.

In some embodiments, the two or more different nucleic acid templates are localized, deposited or positioned at different sites prior to the amplifying.

In some embodiments, the two or more different nucleic acid templates are clonally amplified in solution, optionally within a single reaction mixture, and the resulting two or more substantially monoclonal nucleic acid populations are then localized, deposited or positioned at different sites following such clonal amplification.

The different sites are optionally members of an array of sites. The array can include a two-dimensional array of sites on a surface (e.g., of a flowcell, electronic device, transistor chip, reaction chamber, channel, and the like), or a three-dimensional array of sites within a matrix or other medium (e.g., solid, semi-solid, liquid, fluid, and the like).

In some embodiments, the two or more different nucleic acid templates are amplified within a continuous liquid phase, typically a continuous aqueous phase, of the same reaction mixture, thereby producing two or more different and substantially monoclonal populations of polynucleotides, each population being generated via amplification of a single polynucleotide template present in the reaction mixture.

In some embodiments, the continuous liquid phase is contained within a single or same phase of the reaction mixture.

In some embodiments, the disclosure relates generally to methods (as well as related compositions, systems and kits) for nucleic acid synthesis, comprising: providing a double stranded nucleic acid template; and forming a substantially monoclonal nucleic acid population by amplifying the double stranded nucleic acid template. Optionally, the amplifying includes clonally amplifying the double stranded nucleic acid template.

In some embodiments, the amplifying includes performing at least one round of amplification under substantially isothermal conditions.

In some embodiments, the amplifying includes performing at least two consecutive cycles of nucleic acid synthesis under substantially isothermal conditions.

In some embodiments, the RPA methods can be used for template walking. For example, the amplifying can include performing at least one round of template-walking.

In some embodiments, the amplifying optionally includes performing two different rounds of amplification within the sites or reaction chambers. For example, the amplifying can include performing at least one round of the RPA methods within the sites or reaction chambers, and performing at least one round of template walking, which may or may not use the RPA methods with blocked primes, within the sites or reaction chambers, in any order or combination of rounds. In some embodiments, at least two consecutive cycles in any one or more of the rounds of amplification are performed under substantially isothermal conditions. In some embodiments, at least one of the rounds of amplification is performed under substantially isothermal conditions.

In some embodiments, the nucleic acid template to be amplified is double stranded, or is rendered at least partially double stranded using appropriate procedures prior to amplification. (The template to be amplified is referred to interchangeably herein as a nucleic acid template or a polynucleotide template). In some embodiments, the template is linear. Alternatively, the template can be circular, or include a combination of linear and circular regions.

In some embodiments, the double stranded nucleic acid template includes a forward strand. The double stranded nucleic acid template can further include a reverse strand. The forward strand optionally includes a first primer binding site. The reverse strand optionally includes a second primer binding site.

In some embodiments, the template already includes a first and/or second primer binding site. Alternatively, the template optionally does not originally include a primer binding site, and the disclosed methods optionally include attaching or introducing a primer binding site to the template prior to the amplifying. For example, the method can optionally include ligating or otherwise introducing an adapter containing a primer binding site to, or into, the templates. The adapter can be ligated or otherwise introduced to an end of a linear template, or within the body of a linear or circular template. Optionally, the template can be circularized after the adapter is ligated or introduced. In some embodiments, a first adapter can be ligated or introduced at a first end of a linear template, and a second adaptor can be ligated or introduced at a second end of the template.

In some embodiments, the amplifying includes contacting the partially denatured template with a first blocked primer, with a second blocked primer, or with both a first blocked primer and a second blocked primer, in any order or combination.

In some embodiments, the first blocked primer contains a first primer sequence. The first blocked primer optionally includes an extendible end (e.g., a 3'OH containing end), after cleavage by the ribo-endonuclease to liberate the blocking group and the 3' domain of the blocked primers. The first blocked primer can optionally be attached to a compound (e.g., a "drag tag"), or to a support (e.g., a bead or a surface of the site or reaction chamber).

In some embodiments, the second blocked primer contains a second primer sequence. The second primer optionally includes an extendible end (e.g., a 3'OH containing end) after cleavage by the ribo-endonuclease to liberate the blocking group and the 3' domain of the blocked primers. The second blocked primer can optionally be attached to a compound (e.g., a "drag tag"), or to a support (e.g., a bead or a surface of the site or reaction chamber).

Optionally, the first blocked primer binds to the first primer binding site to form a first primer-template duplex. The second blocked primer can bind to the second primer binding site to form a second primer-template duplex.

In some embodiments, amplifying includes extending the first blocked primer (after cleavage by the ribo-endonuclease to liberate the blocking group and the 3' domain of the blocked primers) to form an extended first primer. For example, amplifying can include extending the first blocked primer of the first primer-template duplex to form an extended first primer.

In some embodiments, amplifying includes extending the first blocked primer (after cleavage by the ribo-endonuclease to liberate the blocking group and the 3' domain of the blocked primers) to form an extended first primer. For example, amplifying can include extending the first blocked primer of the first primer-template duplex to form an extended first primer.

In some embodiments, the amplifying includes forming a partially denatured template. For example, the amplification can include partially denaturing the double stranded nucleic acid template.

In some embodiments, partially denaturing includes subjecting the double stranded nucleic acid template to partially denaturing conditions.

In some embodiments, partially denaturing conditions include treating or contacting the nucleic acid templates to be amplified with one or more enzymes that are capable of partially denaturing the nucleic acid template, optionally in a sequence-specific or sequence-directed manner.

In some embodiments, at least one enzyme catalyzes strand invasion and/or unwinding, optionally in a sequence-specific manner. Optionally, the one or more enzymes include one or more enzymes selected from the group consisting of: recombinases, topoisomerases and helicases. In some embodiments, partially denaturing the template can include contacting the template with a recombinase and forming a nucleoprotein complex including the recombinase. Optionally, the template is contacted with a recombinase in the presence of a first blocked primer, a second blocked primer, or both a first and second blocked primer. Partially denaturing can include catalyzing strand exchange using the recombinase and hybridizing the first blocked primer to the first primer binding site (or hybridizing the second blocked primer to the second primer binding site). In some embodiments, partially denaturing includes performing strand exchange and hybridizing both the first blocked primer to the first primer binding site and the second blocked primer to the second primer binding site using the recombinase.

In some embodiments, the partially denatured template includes a single stranded portion and a double stranded portion. In some embodiments, the single stranded portion includes the first primer binding site. In some embodiments, the single stranded portion includes the second primer binding site. In some embodiments, the single stranded portion includes both the first primer binding site and the second primer binding site.

In some embodiments, partially denaturing the template includes contacting the template with one or more nucleoprotein complexes. At least one of the nucleoprotein complexes can include a recombinase. At least one of the nucleoprotein complexes can include a blocked primer (e.g., a first primer or a second primer, or a primer including a sequence complementary to a corresponding primer binding sequence in the template). In some embodiments, partially denaturing the template can include contacting the template with a nucleoprotein complex including a primer. Partially denaturing can include hybridizing the blocked primer of the nucleoprotein complex to the corresponding primer binding site in the template, thereby forming a primer-template duplex.

In some embodiments, partially denaturing the template can include contacting the template with a first nucleoprotein complex including a first blocked primer. Partially denaturing can include hybridizing the first blocked primer of the first nucleoprotein complex to the first primer binding site of the forward strand, thereby forming a first blocked primer-template duplex.

In some embodiments, partially denaturing the template can include contacting the template with a second nucleoprotein complex including a second blocked primer. Partially denaturing can include hybridizing the second blocked primer of the second nucleoprotein complex to the second primer binding site of the reverse strand, thereby forming a second primer-template duplex.

In some embodiments, the disclosed methods (and related compositions, systems and kits) can further include one or more primer extension steps. For example, the methods can include extending a primer via nucleotide incorporation using a polymerase. As understood with the current RPA methods and blocked primers, before primer extension can proceed the RNase H enzyme (e.g. RNase HII) cleaves the primer at the ribobase location. The 5' domain remains hybridized to the template with a 3'OH group available for primer extension, while the 3' domain containing the blocking group is dispersed into the reaction mixture and does not participate in nucleic acid amplification.

In some embodiments, extending a primer includes contacting the hybridized primer with a polymerase and one or more types of nucleotides under nucleotide incorporation conditions. Typically, extending a primer occurs in a template-dependent fashion.

In some embodiments, the methods (and related compositions, systems and kits) include extending the first primer by incorporating one or more nucleotides into the first primer of the first primer-template duplex using the polymerase, thereby forming an extended first primer.

In some embodiments, the methods (and related compositions, systems and kits) include binding a second blocked primer to the second primer binding site of the first extended primer by any suitable method (e.g., ligation or hybridization).

In some embodiments, the methods (and related compositions, systems and kits) include extending the second primer by incorporating one or more nucleotides into the second primer of the second primer-template duplex using the polymerase, thereby forming an extended second primer. However, before primer extension can proceed the RNase H enzyme (e.g. RNase HII) cleaves the hybridized primer at the ribobase location. The 5' domain remains hybridized to the template with a 3'OH group available for primer extension, while the 3' domain containing the blocking group is dispersed into the reaction mixture and does not participate in nucleic acid amplification.

In some embodiments, extending the first primer results in formation of a first extended primer. The first extended primer can include some or all of the sequence of the reverse strand of the template. Optionally, the first extended primer includes a second primer binding site.

In some embodiments, extending the second primer results in formation of a second extended primer. The second extended primer can include some or all of the sequence of the forward strand of the template. Optionally, the second extended primer includes a first primer binding site.

In some embodiments, the methods are performed without subjecting the double stranded nucleic acid template to extreme denaturing conditions during the amplifying. For example, the methods can be performed without subjecting the nucleic acid template(s) to temperatures equal to or greater than the Tm of the template(s) during the amplifying. In some embodiments, the methods can be performed without contacting the template(s) with chemical denaturants such as NaOH, urea, guanidium, and the like, during the amplifying. In some embodiments, the amplifying includes isothermally amplifying.

In some embodiments, the methods are performed without subjecting the nucleic acid template(s) to extreme denaturing conditions during 2, 3, 4, 5, 10, 15, 20, 25, and 30 consecutive cycles on the low end of the range and 5, 10, 15, 20, 25, 30, or 50 consecutive cycles on the high end of the range of nucleic acid synthesis. For example, the methods can include 2, 3, 4, 5, 10, 15, 20, 25, and 30 consecutive cycles on the low end of the range and 5, 10, 15, 20, 25, 30, or 50 consecutive cycles on the high end of the range of nucleic acid synthesis without contacting the nucleic acid template(s) with a chemical denaturant or raising the temperature above 50 or 55° C. In some embodiments, the methods can include performing 2, 3, 4, 5, 10, 15, 20, 25, and 30 consecutive cycles on the low end of the range and 5, 10, 15, 20, 25, 30, or 50 consecutive cycles on the high end of the range of nucleic acid synthesis without subjecting the nucleic acid template(s) to temperatures that are greater than 25, 20, 15, 10, 5, 2 or 1° C. below the actual or calculated Tm of the template, or population of templates (or the actual or calculated average Tm of the template, or population of templates). The consecutive cycles of nucleic acid synthesis may or may not include intervening steps of partial denaturation and/or primer extension.

In some embodiments, the disclosed methods (and related compositions, systems and kits) can further include linking one or more extended primer strands to a support. The linking can optionally be performed during the amplifying, or alternatively after the amplification is complete. In some embodiments, the support includes multiple instances of a second blocked primer, and the methods can include hybridizing at least one of the extended first primer strands to a second blocked primer of the support.

In some embodiments, the disclosed methods (and related compositions, systems and kits) can further include linking one or more extended second primer strands to a support. In some embodiments, the support is attached to a first blocked primer. For example, the support can include multiple instances of a first blocked primer, and the methods can include hybridizing at least one of the extended second primers to a first blocked primer of the support, thereby linking the extended second primer to the support. For example, the first primer can hybridize to a first primer binding site in the extended second primer.

In some embodiments, the support is attached to a second blocked primer. For example, the support can include multiple instances of a second blocked primer, and the methods can include hybridizing at least one of the extended first primers to a second blocked primer of the support, thereby linking the extended first primer to the support. For example, the first blocked primer can hybridize to a second primer binding site in the extended first primer.

In some embodiments, the support includes both at least one first blocked primer and at least one second blocked primer, and the disclosed methods (and related compositions, systems and kits) including linking both an extended first primer and an extended second primer to the support.

In some embodiments, the support is attached to a target-specific blocked primer. The target-specific primer optionally hybridizes (or is capable of hybridizing) to a first subset of templates within the reaction mixture, but is unable to bind to a second subset of templates within the reaction mixture.

In some embodiments, the support is attached to a universal blocked primer. The universal primer optionally hybridizes (or is capable of hybridizing) to all, or substantially all, of the templates within the reaction mixture.

In some embodiments, the reaction mixture includes a first support covalently attached to a first target-specific blocked primer and a second support covalently attached to a second target-specific blocked primer, and wherein the first and second target-specific primers are different from each other.

In some embodiments, the first target-specific blocked primer is substantially complementary to a first target nucleic acid sequence and the second target-specific blocked primer is substantially complementary to a second target nucleic acid sequence, and wherein the first and second target nucleic acid sequences are different.

In some embodiments, the disclosed methods include forming a first amplicon by amplifying a first template onto a first support, and forming a second amplicon by amplifying a second template onto a second support, optionally within the same continuous phase of a reaction mixture. The first amplicon is optionally linked or attached to the first support, and the second amplicon is optionally linked or attached to the second support.

The disclosed methods optionally comprise producing two or more monoclonal, or substantially monoclonal, amplicons by clonally amplifying two or more polynucleotide templates. The two or more polynucleotide templates are optionally clonally amplified within a continuous liquid phase of an amplification reaction mixture. The continuous liquid phase of the amplification reaction mixture can include a continuous aqueous phase. In some embodiments, the amplifying includes generating at least two substantially monoclonal populations of amplified polynucleotides, each of said populations being formed via amplification of a single polynucleotide template. In some embodiments, the clonally amplifying includes at least one round of RPA. Optionally, the clonally amplifying includes at least one round of template walking.

In some embodiments, the amplifying optionally includes forming an amplification reaction mixture including a continuous liquid phase. In some embodiments, the continuous liquid phase is a single continuous aqueous phase. The liquid phase can include two or more polynucleotide templates, which can optionally be different from each other. For example, the two or more polynucleotide templates can include at least one nucleic acid sequence that is substantially non-identical, or substantially non-complementary, to at least one other polynucleotide template within the amplification reaction mixture.

In some embodiments, the amplifying optionally includes forming an amplification reaction mixture including a single continuous aqueous phase having two or more polynucleotide templates. Amplifying optionally includes forming two or more substantially monoclonal nucleic acid populations by clonally amplifying the two or more polynucleotide templates within the single aqueous phase. Optionally, the clonally amplifying includes at least one round of RPA. Optionally, the clonally amplifying includes at least one round of template walking.

In some embodiments, the disclosure relates generally to methods (and related compositions, systems and kits) for amplifying one or more nucleic acid templates, optionally in parallel, using partially denaturing conditions. In some embodiments, two or more templates are amplified using such methods, optionally in array format. Optionally, the templates are amplified in bulk in solution prior to distribution into the array. Alternatively, the templates are first distributed to sites in the array and then amplified in situ at (or within) the sites of the array.

In some embodiments, the methods can include subjecting a double-stranded nucleic acid template including a primer binding site on at least one strand to at least one cycle of template-based replication using a polymerase.

In some embodiments, the at least one cycle of template-based replication includes a partial denaturation step, an annealing step, and an extension step.

In some embodiments, the methods include amplifying the double stranded nucleic acid template by subjecting the template to at least two consecutive cycles of template-based replication.

In some embodiments, the methods include partially denaturing the template. Optionally, the methods include forming a partially denatured template including a single stranded region. The partially denatured template can also include a double stranded region. The single stranded region can contain the primer binding site.

In some embodiments, the partially denaturing includes contacting the double stranded template with a recombinase and a blocked primer. The recombinase and primer may form part of a nucleoprotein complex, and the partially denaturing includes contacting the template with the complex.

In some embodiments, the methods include forming a primer-template duplex by hybridizing a blocked primer to the primer binding site of the single stranded region. In some embodiments, the primed template includes a double stranded region. Optionally, the double stranded region does not contain a primer binding site.

In some embodiments, the methods include extending the primer of the primer-template duplex. Optionally, the methods include forming an extended primer.

In some embodiments, different templates can be clonally amplified onto different discrete supports (e.g., beads or particles) without the need for compartmentalization prior to amplification. In some embodiments, the templates are partitioned or distributed into emulsions prior to amplifying. Optionally, the templates are distributed into droplets forming part of a hydrophilic phase of an emulsion having a discontinuous hydrophilic phase and a continuous hydrophobic phase. In some embodiments, the emulsion droplets of the hydrophilic phase also include one or more components necessary to practice RPA and including the blocked primers and RNase H enzyme. For example, the emulsion droplets can include a recombinase. Optionally, the droplets include a strand-displacing polymerase. In some embodiments, the droplets include a support-immobilized blocked primer and/or a solution phase blocked primer. Optionally, the primer can bind to the template, or to an amplification product thereof. Some suitable emulsion compositions for use with the disclosed amplification methods can be found, for example, in U.S. Pat. Nos. 7,622,280, 7,601,499 and 7,323,305, incorporated by reference herein in their entireties.

In some embodiments, the disclosure relates generally to methods, as well as related compositions and kits, wherein the nucleic acid amplification further include sequencing an amplified template, or sequencing an extended primer, (e.g. an extended first primer, or extended second primer). The sequencing can include any suitable method of sequencing known in the art. In some embodiments, the sequencing includes sequencing by synthesis or sequencing by electronic detection (e.g., nanopore sequencing). In some embodiments, sequence includes extending a template or amplified template, or extending a sequencing primer hybridized to a template or amplified template, via nucleotide incorporation by a polymerase. In some embodiments, sequencing includes sequencing a template or amplified template that is attached to a support by contacting the template or extended primer with a sequencing primer, a polymerase, and at least one type of nucleotide. In some embodiments, the sequencing includes contacting the template, or amplified template, or extended primer, with a sequencing primer, a polymerase and with only one type of nucleotide that does not include an extrinsic label or a chain terminating group.

In some embodiments, the template (or amplified product) can be deposited, localized, or positioned, to a site. In some embodiments, multiple templates/amplified templates/extended first primers are deposited or positioned to different sites in an array of sites. In some embodiments, the depositing, positioning or localizing is performed prior to amplification of the template. In some embodiments, the depositing, positioning or localizing is performed after the amplifying. For example, amplified templates or extended first primers can be deposited, positioned or localized to different sites of an array.

In some embodiments, the disclosed methods result in the production of a plurality of amplicons, at least some of which amplicons include a clonally amplified nucleic acid population. The clonally amplified populations produced by the methods of the disclosure can be useful for a variety of purposes. In some embodiments, the disclosed methods (and related compositions, systems and kits) optionally include further analysis and/or manipulation of the clonally amplified populations (amplicons). For example, in some embodiments, the numbers of amplicons exhibiting certain desired characteristics can be detected and optionally quantified.

In some embodiments, the amplifying is followed by sequencing the amplified product. The amplified product that is sequenced can include an amplicon comprising a substantially monoclonal nucleic acid population. In some embodiments, the disclosed methods include forming or positioning single members of a plurality of amplicons to different sites. The different sites optionally form part of an array of sites. In some embodiments, the sites in the array of sites include wells (reaction chambers) on the surface of an isFET array, as described further herein.

In some embodiments, methods of downstream analysis include sequencing at least some of the plurality of amplicons in parallel. Optionally, the multiple templates/amplified templates/extended first primers situated at different sites of the array are sequenced in parallel.

In some embodiments, the sequencing can include binding a sequencing primer to the nucleic acids of at least two different amplicons, or at least two different substantially monoclonal populations.

In some embodiments, the sequencing can include incorporating a nucleotide into the sequencing primer using the polymerase. Optionally, the incorporating includes forming at least one nucleotide incorporation byproduct, including hydrogen ions, protons, pyrophosphate, charge transfer or heat.

Optionally, the nucleic acid to be sequenced is positioned at a site. The site can include a reaction chamber or well. The site can be part of an array of similar or identical sites. The array can include a two-dimensional array of sites on a surface (e.g., of a flowcell, electronic device, transistor chip, reaction chamber, channel, and the like), or a three-dimensional array of sites within a matrix or other medium (e.g., solid, semi-solid, liquid, fluid, and the like).

In some embodiments, the site is operatively coupled to a sensor. The method can include detecting the nucleotide incorporation using the sensor. Optionally, the site and the sensor are located in an array of sites coupled to sensors.

In some embodiments, the methods (and related compositions, systems and kits) can include detecting the presence of one or more nucleotide incorporation byproducts at a site of the array, optionally using the FET.

In some embodiments, the methods can include detecting a pH change occurring within the at least one reaction chamber, optionally using the FET.

In some embodiments, the amplified nucleic acids can be further analyzed (e.g., sequencing) at the site of distribution without recovering and moving the amplified products to a different site or surface for analysis (e.g., sequencing).

In some embodiments, methods of downstream analysis include sequencing at least some of the plurality of amplicons in parallel. Optionally, the multiple templates/amplified templates/extended first primers situated at different sites of the array are sequenced in parallel.

In some embodiments, the methods (and related compositions, systems and kits) can include depositing, positioning or localizing at least one substantially monoclonal population at a site. The site can form part of an array of sites.

In some embodiments, at least one of the sites includes a reaction chamber, support, particle, microparticle, sphere, bead, filter, flowcell, well, groove, channel reservoir, gel or inner wall of a tube.

In some embodiments the nucleic acid templates can be distributed into the wells of an isFET array and subsequent amplification of templates inside the wells of the array, an optional step of downstream analysis can be performed after the amplification that quantifies the number of sites or wells that include amplification product. In some embodiments, the products of the nucleic acid amplification reactions can be detected in order to count the number of sites or wells that include an amplified template.

For example, in some embodiments the disclosure relates generally to methods of nucleic acid analysis, comprising: providing a sample including a first number of polynucleotides; and distributing single polynucleotides of the sample into different sites in an array of sites.

In some embodiments, the methods can further include forming substantially monoclonal nucleic acid populations by amplifying the single polynucleotides within their respective sites.

In some embodiments, the sites remain in fluid communication during the amplifying.

In some embodiments, the amplifying includes partially denaturing the template.

In some embodiments, the amplifying includes subjecting the template to partially denaturing temperatures. In some embodiments, the template includes a low-melt sequence including a primer binding site, which is rendered single stranded when the template is subjected to partially denaturing temperatures.

In some embodiments, the amplifying includes partially denaturing the template.

In some embodiments, the amplifying includes contacting at least two different templates at two different sites of the array with a single reaction mixture for nucleic acid amplification.

In some embodiments, the reaction mixture includes a recombinase.

In some embodiments, the reaction mixture includes at least one primer including a "drag-tag".

In some embodiments, the amplifying includes performing at least one amplification cycle that includes partially denaturing the template, hybridizing a primer to the template, and extending the primer in a template-dependent fashion. Optionally, the amplifying includes isothermally amplifying. In some embodiments, the amplifying is performed under substantially isothermal conditions.

In some embodiments, the percentage of sites containing one or more template molecules is greater than 50% and less than 100%.

In some embodiments, the disclosed methods can further include detecting a change in ion concentration in at least one of the sites as a result of the at least one amplification cycle.

In some embodiments, the disclosure relates generally to methods for detection of a target nucleic acid comprising: fractionating a sample into a plurality of sample volumes wherein more than 50% of the fractions contain no more than 1 target nucleic acid molecule per sample volumes; subjecting the plurality of sample volumes to conditions for amplification, wherein the conditions include partially denaturing conditions; detecting a change in ion concentration in a sample volume wherein a target nucleic acid is present; counting the number of fractions with an amplified target nucleic acid; and determining the quantity of target nucleic acid in the sample. The change in ion concentration may be an increase in ion concentration or may be a decrease in ion concentration. In some embodiments, the method may further include combining a sample with bead. In some embodiments, the method may include loading the sample on a substrate wherein the substrate includes at least one well.

In some embodiments, subjecting the target nucleic acids to partially denaturing conditions includes contacting the target nucleic acid molecules in their respective sample volumes with a recombinase and a polymerase under RPA conditions.

In some embodiments, subjecting the target nucleic acids to partially denaturing conditions includes subjecting the target nucleic acid molecules to partially denaturing temperatures.

In some embodiments, the disclosure relates generally to compositions (and relate methods for making and using said compositions) comprising reagents for amplifying one or more nucleic acid templates in parallel using partially denaturing conditions.

In some embodiments, the disclosure relates generally to methods for clonally amplifying a population of nucleic acid templates onto a population of supports in an amplification reaction solution, comprising: clonally amplifying a first template onto a first nucleic acid template onto a first support according to any of the methods disclosed herein, and clonally amplifying a second nucleic acid template onto a second support according to the same method, wherein both supports are included within a single continuous liquid phase during the amplifying.

In some embodiments, a method is provided of generating a localized clonal population of immobilized clonal amplicons of a single-stranded template sequence using a template-walking method, comprising: (a) attaching the single-stranded template sequence ("template 1") to an immobilization site ("IS1"), wherein IS1 comprises multiple copies of an immobilized blocked primer ("IS1 primer") which can hybridize substantially to template 1, and template 1 is attached to IS1 by hybridization to an IS1 primer, and (b) amplifying template 1 using IS1 primer and a non-immobilized optionally blocked RNase cleavable primer ("SP1 primer") in solution, wherein amplified strands that are complementary to the single-stranded template 1 cannot hybridize substantially when single-stranded to primers on IS1, wherein amplification generates a localized clonal population of immobilized clonal amplicons around the point of initial hybridization of template 1 to IS In methods provided in this section that include an IS1 and IS1 primer, a polymerase, recombinase, and associated proteins are used to practice to methods, along with at least one blocked RNase cleavable primer.

Also provided is a method of generating separated and immobilized clonal populations of a first template sequence ("template 1") and a second template sequence ("template 2"), comprising amplifying the first and second template sequence to generate a population of clonal amplicons of template 1 substantially attached to first immobilization site ("IS1") and not to a second immobilization site ("IS2"), or a population of clonal amplicons of template 2 substantially attached to IS2 and not to IS1, wherein: (a) both templates and all amplicons are contained within the same continuous liquid phase, where the continuous liquid phase is in contact with a first and second immobilization site (respectively, "IS1" and "IS2"), and where IS1 and IS2 are spatially separated, (b) template 1 when in single-stranded form comprises a first subsequence ("T1-FOR") at one end, and a second subsequence ("T1-REV") at its opposite end, (c) template 2 when in single-stranded form comprises a first subsequence ("T2-FOR") at one end, and a second subsequence ("T2-REV") at its opposite end, (d) IS1 comprises multiple copies of an immobilized nucleic acid optionally blocked RNase cleavable primer ("IS1 primer") that can hybridize substantially to T1-FOR and T2-FOR when T1 and T2 are single-stranded, (e) IS2 comprises multiple copies of an immobilized optionally blocked RNase cleavable primer ("IS2 primer") that can hybridize substantially to both T1-FOR and T2-FOR when T1 and T2 are single-stranded, (f) the reverse complement of T1-REV when single-stranded cannot hybridize substantially to optionally blocked primers on IS1, but can hybridize substantially to a non-immobilized optionally blocked RNase cleavable primer ("SP1") in the continuous liquid phase; and (g) the reverse complement of T2-REV when single-stranded cannot hybridize substantially to primers on IS2, but can hybridize substantially to a non-immobilized optionally blocked RNase cleavable primer ("SP2") in the continuous liquid phase. At least one of the primers in the methods disclosed in this paragraph is a blocked RNase cleavable primer. In some embodiments, at least one of the immobilized primers in this paragraph is a blocked RNase cleavable primer.

In some embodiments, in any method described herein, any nucleic acid that has dissociated from one immobilization site is capable of substantially hybridizing to both immobilization sites and any movement (e.g., movement by diffusion, convection) of said dissociated nucleic acid to another immobilization site is not substantially retarded in the continuous liquid phase.

In some embodiments, in any method described herein, the continuous liquid phase is in simultaneous contact with IS1 and IS2.

In some embodiments, in any method described herein, a first portion of a template that is bound by an immobilized primer does not overlap with a second portion of the template whose complement is bound by a non-immobilized primer.

In some embodiments, in any method described herein, at least one template to be amplified is generated from an input nucleic acid after the nucleic acid is placed in contact with at least one immobilization site.

In some embodiments, any method described herein comprising the steps of: (a) contacting a support comprising immobilized primers with a single-stranded nucleic acid template, wherein: hybridizing a first immobilized primer to a primer-binding sequence (PBS) on the template (b)

extending the hybridized first primer in template-dependent extension to form an extended strand that is complementary to the template and at least partially hybridized to the template; (c) partially denaturing the template from the extended complementary strand such that at least a portion of the PBS is in single-stranded form ("free portion"); (d) hybridizing the free portion to a non-extended, immobilized second primer (e) extending the second primer in template-dependent extension to form an extended strand that is complementary to the template (f) optionally, separating the annealed extended immobilized nucleic acid strands from one another. In methods provided herein, a polymerase, recombinase, and associated proteins are used to practice to methods, along with at least one blocked RNase cleavable primer.

In some embodiments, during amplification, nucleic acid duplexes are formed comprising a starting template and/or amplified strands; which duplexes are not subjected during amplification to conditions that would cause complete denaturation of a substantial number of duplexes.

In some embodiments, the single-stranded templates are produced by taking a plurality of input double-stranded or single-stranded nucleic acid sequences to be amplified (which sequence may be known or unknown) and appending or creating a first universal adaptor sequence and a second universal adaptor sequence onto the ends of at least one input nucleic acid; wherein said first universal adaptor sequence hybridizes to IS1 primer and/or IS2 primer, and the reverse complement of said second universal adaptor sequence hybridizes to at least one non-immobilized primer. The adaptors can be double-stranded or single-stranded.

In some embodiments, the disclosure relates generally to methods, as well as related compositions, systems, kits and apparatuses, for nucleic acid amplification, comprising multiplex nucleic acid amplification, which includes amplifying within a single reaction mixture different nucleic acid target sequences from a sample containing a plurality of different nucleic acid target sequences, the amplifying including generating a plurality of 2-50, or at least fifty different amplified target sequences (or more) by contacting at least a portion of the sample with a polymerase and a plurality of primers under isothermal amplification conditions.

In some embodiments, the disclosure relates generally to methods, as well as related compositions, systems, kits and apparatuses, for nucleic acid amplification, comprising generating substantially monoclonal nucleic acid populations by re-amplifying the amplicons from the multiplex nucleic acid amplification using a nucleic acid amplification reaction (e.g., a recombinase).

Optionally, methods for multiplex nucleic acid amplification can further include a recombinase-mediated nucleic acid amplification method which includes re-amplifying at least some of the 2-50 or the at least fifty different amplified target sequences by: (a) forming a reaction mixture including a single continuous liquid phase containing (i) a plurality of supports, (ii) at least one of the fifty different amplified target sequences, (iii) a recombinase and (iv) an RNase H; and (b) subjecting the reaction mixture to amplification conditions using blocked primers according to the invention, thereby generating a plurality of supports attached to substantially monoclonal nucleic acid populations attached thereto.

In some embodiments, methods for nucleic acid amplification can be conducted in water-in-oil emulsions that provide compartmentalization.

When conducting a nucleic acid amplification using a plurality of polynucleotide templates, clonal amplification using traditional amplification methods typically relies on techniques such as compartmentalization of the reaction mixture into segregated portions or components that are not in fluid communication with each other in order to maintain clonality and prevent cross-contamination of different amplified populations and to maintain adequate yields of monoclonal amplified product. Using such conventional amplification methods, it is typically not feasible to clonally amplify polynucleotide templates within the same reaction mixture without resorting to compartmentalization or distribution of the reaction mixture into separate compartments or vessels, because any polynucleotides within the reaction mixture (including templates and/or amplified products) will tend to migrate randomly through the mixture due to diffusion and/or Brownian motion during such amplification. Such diffusion or migration typically increases the incidence of polyclonal amplification and thus very few, if any, monoclonal populations will be produced.

One suitable technique to reduce the production of polyclonal populations in conventional amplification methods uses physical barriers to separate individual amplification reactions into discrete compartments. For example, emulsion amplification uses water-in-oil microreactors, where an oil phase includes many separate, i.e., discontinuous, aqueous reaction compartments. Each compartment serves as an independent amplification reactor, thus the entire emulsion is capable of supporting many separate amplification reactions in separate (discontinuous) liquid phases in a single reaction vessel (e.g., an Eppendorf tube or a well). Similarly, an amplification "master mix" can be prepared and distributed into separate reaction chambers (e.g., an array of wells), creating a set of discrete and separate phases, each of which defines a separate amplification reaction. Such separate phases can be further sealed off from each other prior to amplification. Such sealing can be useful in preventing cross-contamination between parallel and separate reactions. Exemplary forms of sealing can include use of lids or phase barriers (e.g., mineral oil layer on top of an aqueous reaction) to compartmentalize the PCR reactions into individual and discrete compartments, between which transfer of reaction components does not occur.

Other techniques to prevent cross-contamination and reduce polyclonality rely on immobilization of one or more reaction components (for example, one or more templates and/or primers) during amplification to prevent cross contamination of amplification reaction products and consequent reduction in monoclonality. One such example includes bridge amplification, where all of the primers required for amplification (e.g., forward and reverse primer) are attached to the surface of a matrix support. In addition to such immobilization, additional immobilization components can be included in the reaction mixture. For example, the polynucleotide template and/or amplification primers cam be suspended in gels or other matrices during the amplification so as to prevent migration of amplification reaction products from the site of synthesis. Such gels and matrices typically require to be removed subsequently, requiring the use of appropriate "melting" or other recovery steps and consequent loss of yield.

In some embodiments, the disclosure provides methods for performing substantially clonal amplification of multiple polynucleotide templates in parallel in a single continuous liquid phase of a reaction mixture, without need for compartmentalization or immobilization of multiple reaction components (e.g., both primers) during amplification. Instead, mixtures of polynucleotide templates in solution can be directly contacted with amplification reaction components and a suitable surface or support having a first primer attached thereto. Other components required for amplification can be provided in the same continuous liquid phase, including a polymerase, one or more types of nucleotide and optionally a second primer. In some embodiments, the reaction mixture also includes a recombinase. Optionally, the reaction mixture further includes at least one agent selected from the group consisting of: a diffusion limiting agent, a sieving agent, and a crowding agent. Examples of amplification mixtures suitable for achieving monoclonal amplification of templates contained in a single continuous liquid phase are described further herein. Optionally, different templates can be amplified onto different locations on a single surface or support, or different templates can be amplified onto different surfaces or different supports within the same reaction mixture.

In some embodiments, methods for nucleic acid amplification comprise hybridization to the template of additional primers wherein the reaction mixture comprises at least one blocked primer of the invention. For example, a second primer can be a reverse amplification primer which hybridizes to at least a portion of one strand of a polynucleotide. In some embodiments, a second primer comprises an extendible 3' end. In some embodiment, a second primer is not attached to a surface.

In some embodiments, a third primer can be a forward amplification primer which hybridizes to at least a portion of one strand of a polynucleotide. In some embodiments, a third primer comprises an extendible 3' end. In some embodiment, a third primer is not attached to a surface. In some embodiments, a third primer comprises a binding partner or affinity moiety (e.g., biotin) for enriching the amplified nucleic acids.

In some embodiments, primers (e.g., first, second and third primers) comprise single-stranded oligonucleotides.

In some embodiments, at least a portion of a primer can hybridize with a portion of at least one strand of a polynucleotide in the reaction mixture. For example, at least a portion of a primer can hybridize with a nucleic acid adaptor that is joined to one or both ends of the polynucleotide. In some embodiments, at least a portion of a primer can be partially or fully complementary to a portion of the polynucleotide or to the nucleic acid adaptor. In some embodiments, the nucleic acid adaptor includes one or more universal sequences, for example universal primer binding sequences. In some embodiments, a primer can be compatible for use in any type of sequencing platform including chemical degradation, chain-termination, sequence-by-synthesis, pyrophosphate, massively parallel, ion-sensitive, and single molecule platforms.

In some embodiments, a primer (e.g., first, second or third primer) can have a 5' or 3' overhang tail (tailed primer) that does not hybridize with a portion of at least one strand of a polynucleotide in the reaction mixture. Typically, the blocked primers do not have an overhang tail, however when the reaction mixture comprises an additional primer that is a standard (non-blocked primer) it may comprise an overhang tail. In some embodiments, a tailed primer can be any length, including 1-50 or more nucleotides in length.

In some embodiments, nucleic acids that have been amplified according to the present teachings can be used in any nucleic acid sequencing workflow, including sequencing by oligonucleotide probe ligation and detection (e.g., SOLiD™ from Life Technologies, WO 2006/084131), probe-anchor ligation sequencing (e.g., Complete Genomic™ or Polonator™), sequencing-by-synthesis (e.g., Genetic Analyzer and HiSeq™, from Illumina), pyrophosphate sequencing (e.g., Genome Sequencer FLX from 454 Life Sciences), ion-sensitive sequencing (e.g., Personal Genome Machine (PGM™) and Ion Proton™ Sequencer, both from Ion Torrent Systems, Inc.), single molecule sequencing platforms (e.g., HeliScope™ from Helicos™) and nanopore sequencing via read of individual bases as they pass through the nanopores (e.g. MinION from Oxford Nanopore Technologies).

In some embodiments, nucleic acid that have been amplified according to the present teachings can be sequenced by any sequencing method, including sequencing-by-synthesis, ion-based sequencing involving the detection of sequencing byproducts using field effect transistors (e.g., FETs and ISFETs), chemical degradation sequencing, ligation-based sequencing, hybridization sequencing, pyrophosphate detection sequencing, capillary electrophoresis, gel electrophoresis, next-generation, massively parallel sequencing platforms, sequencing platforms that detect hydrogen ions or other sequencing by-products, and single molecule sequencing platforms. In some embodiments, a sequencing reaction can be conducted using at least one sequencing primer that can hybridize to any portion of the polynucleotide constructs, including a nucleic acid adaptor or a target polynucleotide.

In some embodiments, the sequencing can be conducted on a support having a plurality of sequencing reaction sites arranged in an array on the support, where the sequencing reaction sites are capacitively coupled to at least one sensor that detects the presence or a change in concentration of a nucleotide incorporation byproduct (e.g., pyrophosphate, hydrogen ion, charge transfer, heat). In some embodiments, the support includes at least $10^2$, $10^3$, $10^4$, $10^5$, $10^6$, $10^7$, $10^8$, $10^9$ reaction sites, where each site is capacitively coupled to at least one sensor. In some embodiments, the sensor comprises a field effect transistor, including those described in in U.S. Pat. No. 7,948,015 to Rothberg et al.; and Rothberg et al, U.S. Patent Publication No. 2009/0026082, hereby incorporated by reference in their entireties. Other examples of methods of detecting polymerase-based extension can be found, for example, in Pourmand et al, Proc. Natl. Acad. Sci., 103: 6466-6470 (2006); Purushothaman et al., IEEE ISCAS, IV-169-172; Anderson et al, Sensors and Actuators B Chem., 129: 79-86 (2008); Sakata et al., Angew. Chem. 118:2283-2286 (2006); Esfandyapour et al., U.S. Patent Publication No. 2008/01666727; and Sakurai et al., Anal. Chem. 64: 1996-1997 (1992). In addition detection may be based on a change in capacitance, impedance or conductivity or voltammetry.

In various exemplary embodiments, the methods, systems, and computer readable media described herein may advantageously be used to process and/or analyze data and signals obtained from electronic or charged-based nucleic acid sequencing. In electronic or charged-based sequencing (such as, pH-based sequencing), a nucleotide incorporation event may be determined by detecting ions (e.g., hydrogen ions) that are generated as natural by-products of polymerase-catalyzed nucleotide extension reactions. This may be used to sequence a sample or template nucleic acid, which may be a fragment of a nucleic acid sequence of interest, for example, and which may be directly or indirectly attached as a clonal population to a solid support, such as a particle, microparticle, bead, etc. The sample or template nucleic acid may be operably associated to a primer and polymerase and may be subjected to repeated cycles or "flows" of nucleotide addition (which may be referred to herein as "nucleotide flows" from which nucleotide incorporations may result) and washing. The primer may be annealed to the sample or template so that the primer's 3' end can be extended by a polymerase whenever nucleotides complementary to the next base in the template are added. Then, based on the known sequence of nucleotide flows and on measured output signals of the chemical sensors indicative of ion concentration during each nucleotide flow, the identity of the type, sequence and number of nucleotide(s) associated with a sample nucleic acid present in a reaction region coupled to a chemical sensor can be determined.

In a typical embodiment of ion-based nucleic acid sequencing, nucleotide incorporations can be detected by detecting the presence and/or concentration of hydrogen ions generated by polymerase-catalyzed extension reactions. In one embodiment, templates, optionally pre-bound to a sequencing primer and/or a polymerase, can be loaded into reaction chambers (such as the microwells disclosed in Rothberg et al, cited herein), after which repeated cycles of nucleotide addition and washing can be carried out. In some embodiments, such templates can be attached as clonal populations to a solid support, such as particles, bead, or the like, and said clonal populations are loaded into reaction chambers.

In another embodiment, the templates, optionally bound to a polymerase, are distributed, deposited or positioned to different sites of the array. The site of the array includes primers and the methods can include hybridizing different templates to the primers within different sites.

In each addition step of the cycle, the polymerase can extend the primer by incorporating added nucleotide only if the next base in the template is the complement of the added nucleotide. If there is one complementary base, there is one incorporation, if two, there are two incorporations, if three, there are three incorporations, and so on. With each such incorporation there is a hydrogen ion released, and collectively a population of templates releasing hydrogen ions changes the local pH of the reaction chamber. The production of hydrogen ions is monotonically related to the number of contiguous complementary bases in the template (as well as the total number of template molecules with primer and polymerase that participate in an extension reaction). Thus, when there are a number of contiguous identical complementary bases in the template (i.e. a homopolymer region), the number of hydrogen ions generated, and therefore the magnitude of the local pH change, can be proportional to the number of contiguous identical complementary bases. If the next base in the template is not complementary to the added nucleotide, then no incorporation occurs and no hydrogen ion is released. In some embodiments, after each step of adding a nucleotide, an additional step can be performed, in which an unbuffered wash solution at a predetermined pH is used to remove the nucleotide of the previous step in order to prevent misincorporations in later cycles. In some embodiments, the after each step of adding a nucleotide, an additional step can be performed wherein the reaction chambers are treated with a nucleotide-destroying agent, such as apyrase, to eliminate any residual nucleotides remaining in the chamber, which may result in spurious extensions in subsequent cycles.

In one exemplary embodiment, different kinds of nucleotides are added sequentially to the reaction chambers, so that each reaction can be exposed to the different nucleotides one at a time. For example, nucleotides can be added in the following sequence: dATP, dCTP, dGTP, dTTP, dATP, dCTP, dGTP, dTTP, and so on; with each exposure followed by a wash step. The cycles may be repeated for 50 times, 100 times, 200 times, 300 times, 400 times, 500 times, 750 times, or more, depending on the length of sequence information desired.

In some embodiments, sequencing can be performed according to the user protocols supplied with the PGM™ or Proton™ sequencer. Example 3 provides one exemplary protocol for ion-based sequencing using the Ion Torrent PGM™ sequencer (Ion Torrent™ Systems, Thermo Fisher Scientific, CA). In some embodiments, sequencing can be performed according to the user protocols supplied with the Ion S5 or Ion S5 XL sequencer (Ion Torrent™ Systems).

In some embodiments, the disclosure relates generally to methods for sequencing a population of nucleic acid templates, comprising: (a) generating a plurality of amplicons by clonally amplifying a plurality of nucleic acid templates onto a plurality of surfaces, wherein the amplifying is performed within a single continuous phase of a reaction mixture and wherein at least 10%, 20%, 30%, 40%, 50%, 60%, 70%, 80%, 90%, or 95% of the resulting amplicons are substantially monoclonal or monoclonal in nature. A sufficient number of substantially monoclonal or monoclonal amplicons can be produced in a single amplification reaction to generate at least 100 MB, 200 MB, 300 MB, 400 MB, 500 MB, 750 MB, 1 GB or 2 GB of AQ20 sequencing reads on an Ion Torrent PGM™ 314, 316 or 318 sequencer. With respect to related high throughput systems, a sufficient number of substantially monoclonal or monoclonal amplicons can be produced in a single amplification reaction to generate at least 100 MB, 200 MB, 300 MB, 400 MB, 500 MB, 750 MB, 1 GB, 2 GB, 5 GB, 10 GB or 15 GB of AQ20 sequencing reads on an Ion Torrent Proton, S5 or SSXL sequencer. The term "AQ20 and its variants, as used herein, refers to a particular method of measuring sequencing accuracy in the Ion Torrent PGM™ sequencer. Accuracy can be measured in terms of the Phred-like Q score, which measures accuracy on logarithmic scale that: Q10=90%, Q20=99%, Q30=99.9%, Q40=99.99%, and Q50=99.999%. For example, in a particular sequencing reaction, accuracy metrics can be calculated either through prediction algorithms or through actual alignment to a known reference genome. Predicted quality scores ("Q scores") can be derived from algorithms that look at the inherent properties of the input signal and make fairly accurate estimates regarding if a given single base included in the sequencing "read" will align. In some embodiments, such predicted quality scores can be useful to filter and remove lower quality reads prior to downstream alignment. In some embodiments, the accuracy can be reported in terms of a Phred-like Q score that measures accuracy on logarithmic scale such that: Q10=90%, Q17=98%, Q20=99%, Q30=99.9%, Q40=99.99%, and Q50=99.999%. In some embodiments, the data obtained from a given polymerase reaction can be filtered to measure only polymerase reads measuring "N" nucleotides or longer and having a Q score that passes a certain threshold, e.g., Q10, Q17, Q100 (referred to herein as the "NQ17" score). For example, the 100Q20 score can indicate the number of reads obtained from a given reaction that are at least 100 nucleotides in length and have Q scores of Q20 (99%) or greater. Similarly, the 200Q20 score can indicate the number of reads that are at least 200 nucleotides in length and have Q scores of Q20 (99%) or greater.

In some embodiments, the accuracy can also be calculated based on proper alignment using a reference genomic sequence, referred to herein as the "raw" accuracy. This is single pass accuracy, involving measurement of the "true" per base error associated with a single read, as opposed to consensus accuracy, which measures the error rate from the consensus sequence which is the result of multiple reads. Raw accuracy measurements can be reported in terms of "AQ" scores (for aligned quality). In some embodiments, the data obtained from a given polymerase reaction can be filtered to measure only polymerase reads measuring "N" nucleotides or longer having a AQ score that passes a certain threshold, e.g., AQ10, AQ17, AQ100 (referred to herein as the "NAQ17" score). For example, the 100AQ20 score can indicate the number of reads obtained from a given polymerase reaction that are at least 100 nucleotides in length and have AQ scores of AQ20 (99%) or greater. Similarly, the 200AQ20 score can indicate the number of reads that are at least 200 nucleotides in length and have AQ scores of AQ20 (99%) or greater.

In some embodiments, the present teachings provide systems for nucleic acid amplification, comprising any combination of: beads attached with a plurality of at least one blocked primer of the invention (first primer, second primer, third primer,) polynucleotides, recombinase, recombinase loading protein, single-stranded binding protein (SSB), polymerase, nucleotides, ATP, RNase H enzyme, phosphocreatine, creatine kinase, hybridization solutions, and/or washing solutions. A system can include all or some of these components. In some embodiments, systems for nucleic acid amplification can further comprise any combination of: buffers and/or cations (e.g., divalent cations).

In some embodiments, the present teachings provide kits for nucleic acid amplification. In some embodiments, kits include any reagent that can be used for nucleic acid amplification. In some embodiments, kits include any combination of: beads attached with a plurality of at least one blocked primer of the invention (first primer, second primer, third primer), polynucleotides, recombinase, recombinase loading protein, single-stranded binding protein (SSB), polymerase, nucleotides, ATP, RNase H enzyme, phosphocreatine, creatine kinase, hybridization solutions, washing solutions, buffers and/or cations (e.g., divalent cations). A kit can include all or some of these components.

In some embodiments, the disclosure relates generally to methods, compositions, systems useful for amplifying different nucleic acid templates in parallel in a plurality of compartmentalized reaction volumes, as opposed to amplification within a single continuous liquid phase. For example, the nucleic acid templates can be distributed or deposited into an array of reaction chambers, or an array of reaction volumes, such that at least two such chambers or volumes in the array each receive a single nucleic acid template. In some embodiments, a plurality of separate reaction volumes is formed. The reaction chambers (or reaction volumes) can optionally be sealed prior to amplification. In another embodiment, the reaction mixture can be compartmentalized or separated into a plurality of microreactors dispersed within a continuous phase of an emulsion, the compartmentalized or separate reaction volumes optionally do not mix or communicate, or are not capable of mixing or communicating, with each other. In some embodiments, at least some of the reaction chambers (or reaction volumes) include a recombinase, and optionally a polymerase. The polymerase can be a strand-displacing polymerase.

In some embodiments, the disclosure relates generally to compositions, systems, methods, apparatuses and kits for nucleic acid synthesis and/or amplification including emulsions. As used herein, the term "emulsion" includes any composition including a mixture of a first liquid and a second liquid, wherein the first and second liquids are substantially immiscible with each other. Typically, one of the liquids is hydrophilic while the other liquid is hydrophobic. Typically, the emulsion includes a dispersed phase and a continuous phase. For example, the first liquid can form a dispersed phase that is dispersed in the second liquid, which forms the continuous phase. The dispersed phase is optionally comprised predominantly of the first liquid. The continuous phase is optionally comprised predominantly of the second liquid. In various embodiments, the same two liquids can form different types of emulsions. For example, in a mixture including both oil and water can form, firstly, an oil-in-water emulsion, where the oil is the dispersed phase, and water is the dispersion medium. Secondly, they can form a water-in-oil emulsion, where water is the dispersed phase and oil is the external phase. Multiple emulsions are also possible, including a "water-in-oil-in-water" emulsion and an "oil-in-water-in-oil" emulsion. In some embodiments, the dispersed phase includes one or more microreactors in which nucleic acid templates can be individually amplified. One or more microreactors can form compartmentalized reaction volumes in which separate amplification reactions can occur. One example of a suitable vehicle for nucleic acid amplification includes a water-in-oil emulsion wherein the water-based phase includes several aqueous microreactors that are dispersed within an oil phase of an emulsion. In some embodiments, the emulsion can further include an emulsifier or surfactant. The emulsifier or surfactant can be useful in stabilizing the emulsion under nucleic acid synthesis conditions.

In some embodiments, the disclosure relates generally to a composition comprises an emulsion including a reaction mixture. The emulsion can include an aqueous phase. The aqueous phase can be dispersed in a continuous phase of the emulsion. The aqueous phase can include one or more microreactors. In some embodiments, the reaction mixture is contained in a plurality of liquid phase microreactors within a phase of an emulsion. Optionally, the reaction mixture includes a recombinase. Optionally, the reaction mixture includes a plurality of different polynucleotides. Optionally, the reaction mixture includes a plurality of supports. Optionally, the reaction mixture includes any combination of a recombinase, a plurality of different polynucleotides and/or a plurality of supports. Optionally, at least one of the supports can be attached to a substantially monoclonal nucleic acid population.

In some embodiments, the disclosure relates generally to a composition comprising a reaction mixture, the reaction mixture including (i) a plurality of supports, (ii) a plurality of different polynucleotides and (iii) a recombinase, the reaction mixture contained in a plurality of liquid phase microreactors in an emulsion.

In some embodiments, the disclosure relates generally to a composition comprising a reaction mixture, the reaction mixture including (i) a recombinase and (ii) a plurality of supports, at least one of the supports being attached to a substantially monoclonal nucleic acid population, wherein the reaction mixture is contained in a plurality of liquid phase microreactors in an emulsion.

In some embodiments, the disclosure relates generally to a composition comprising an emulsion. Optionally, the emulsion comprises a hydrophilic phase and a hydrophobic phase. Optionally, the emulsion comprises a hydrophilic phase dispersed in a hydrophobic phase. Optionally, the hydrophilic phase can include any combination of a plurality of polynucleotide templates, a plurality of supports and/or a recombinase. Optionally, the hydrophilic phase can include a plurality of polynucleotide templates. Optionally, the hydrophilic phase can include a plurality of supports. Optionally, the hydrophilic phase can include a recombinase.

In some embodiments, a composition comprises an emulsion comprising a hydrophilic phase and a hydrophobic phase, wherein the hydrophilic phase includes a plurality of polynucleotide templates, a plurality of supports and a recombinase.

In some embodiments, the disclosure relates generally to a composition comprises an emulsion including a hydrophilic phase dispersed in a hydrophobic phase. Optionally, the hydrophilic phase includes a plurality of microreactors. Optionally, at least two microreactors of the plurality includes a different polynucleotide template. Optionally, the sequences of the different polynucleotide templates is the same or different. Optionally, a first microreactor includes a first polynucleotide template and a second microreactor includes a second polynucleotide template. Optionally, the first and the second polynucleotide templates comprise the same or different sequences. Optionally, at least two microreactors of the plurality includes a recombinase.

In some embodiments, a composition comprises an emulsion including a hydrophilic phase dispersed in a hydrophobic phase, wherein the hydrophilic phase including a plurality of microreactors, at least two microreactors of the plurality including a different polynucleotide template and a recombinase.

In some embodiments, the hydrophilic phase includes a plurality of aqueous microreactors, at least two of the microreactors each including a different polynucleotide template, a support, and a recombinase.

Optionally, a first microreactor includes a first polynucleotide template and a second microreactor includes a second polynucleotide template. Optionally, the first and the second polynucleotide templates comprise the same or different sequences.

Optionally, at least one of the plurality of supports is linked to a plurality of first primers (e.g., forward amplification primers).

Optionally, the reaction mixture further includes a plurality of a second primer (e.g., reverse amplification primers).

In some embodiments, at least one of the plurality of supports further includes a plurality of second primers.

In some embodiments, at least one of the plurality of supports includes a plurality of first and second primers.

In some embodiments, the first and second primers comprise the same sequences.

In some embodiments, the first and second primers comprise different sequences. In some embodiments, the hydrophilic phase further includes a polymerase.

In some embodiments, the polymerase comprises a strand displacing polymerase. In some embodiments, the hydrophilic phase includes nucleotides.

In some embodiments, the disclosure relates generally to methods (as well as associated compositions and systems) for nucleic acid synthesis, comprising: (a) forming a reaction mixture; and (b) subjecting the reaction mixture to amplification conditions. Optionally, the reaction mixture is contained within a hydrophilic phase of an emulsion. Optionally, the emulsion includes a hydrophilic phase and a hydrophobic phase. Optionally, the emulsion comprises a hydrophilic phase dispersed in a hydrophobic phase. Optionally, the reaction mixture contains any combination of a plurality of supports, a plurality of different polynucleotides and/or a recombinase. Optionally, the reaction mixture contains a plurality of supports. Optionally, the reaction mixture contains a plurality of different polynucleotides. Optionally, the sequences of the different polynucleotide templates is the same or different. Optionally, a first microreactor includes a first polynucleotide template and a second microreactor includes a second polynucleotide template. Optionally, the first and the second polynucleotide templates comprise the same or different sequences. Optionally, the reaction mixture contains a recombinase. Optionally, the amplification conditions include isothermal or thermo-cycling temperature conditions. Optionally, the method further includes forming at least two supports subjecting the emulsion to amplification conditions results in forming a plurality of supports, wherein at least two of the supports are each independently attached to a substantially monoclonal nucleic acid population.

In some embodiments, the disclosure relates generally to methods (as well as associated compositions and systems) for nucleic acid synthesis, comprising: (a) forming a reaction mixture containing a plurality of supports, a plurality of different polynucleotides and a recombinase, the reaction mixture contained within a hydrophilic phase of an emulsion; and (b) subjecting the emulsion including the reaction mixture to isothermal amplification conditions, thereby generating a plurality of supports and a substantially monoclonal nucleic acid population attached thereto.

In some embodiments, the emulsion includes a water-in-oil emulsion. In some embodiments, the liquid phase microreactors comprise a hydrophilic phase. In some embodiments, the emulsion comprises a hydrophilic phase dispersed in a hydrophobic phase. In some embodiments, the reaction mixture is formed in a single reaction vessel. Optionally, the sequences of the plurality of different polynucleotide templates is the same or different. Optionally, a first polynucleotide template includes a first sequence and a second polynucleotide template includes a second sequence. Optionally, the first and the second polynucleotide template sequences are the same or different. Optionally, at least one of the plurality of supports is linked to a plurality of first primers (e.g., forward amplification primers). Optionally, the reaction mixture further includes a plurality of a second primer (e.g., reverse amplification primers). In some embodiments, at least one of the plurality of supports further includes a plurality of second primers. In some embodiments, at least one of the plurality of supports includes a plurality of first and second primers. In some embodiments, the first and second primers comprise the same sequences. In some embodiments, the first and second primers comprise different sequences. In some embodiments, the nucleic acid synthesis method further includes recovering from the reaction mixture at least some of the supports attached to substantially nucleic acid monoclonal populations. In some embodiments, the nucleic acid synthesis method further includes depositing onto a surface at least some of the supports attached to the substantially monoclonal nucleic acid populations. In some embodiments, the nucleic acid synthesis method further includes forming an array by depositing onto a surface at least some of the supports attached to the substantially monoclonal nucleic acid populations. In some embodiments, the nucleic acid synthesis method further includes sequencing at least one substantially monoclonal nucleic acid population attached to the support. In some embodiments, the support comprises a bead, particle, a planar surface, or an interior wall of a channel or tube. In some embodiments, the reaction mixture further includes a polymerase and a plurality of nucleotides. In some embodiments, the polymerase comprises a strand displacing polymerase.

In some embodiments, methods for nucleic acid synthesis comprise forming an emulsion. Optionally, the emulsion comprises a hydrophilic phase and a hydrophobic phase. Optionally, the emulsion comprises a hydrophilic phase dispersed in a hydrophobic phase. Optionally, the hydrophilic phase includes a plurality of microreactors. Optionally, at least two microreactors of the plurality include individual polynucleotide templates. Optionally, at least two microreactors of the plurality include a different polynucleotide template. Optionally, a first microreactor includes a first polynucleotide template, and a second microreactor includes a second polynucleotide template. Optionally, the first and the second polynucleotide templates have the same or different sequences. Optionally, at least two microreactors of the plurality including a recombinase.

In some embodiments, the disclosure relates generally to methods (as well as associated compositions and systems) for nucleic acid synthesis, comprising: forming an emulsion including a hydrophilic phase dispersed in a hydrophobic phase, the hydrophilic phase including a plurality of microreactors, at least two microreactors of the plurality including a different polynucleotide template and a recombinase.

In some embodiments, the emulsion includes a water-in-oil emulsion. In some embodiments, the hydrophilic phase further includes a polymerase. In some embodiments, the polymerase is a strand displacing polymerase. In some embodiments, the hydrophilic phase includes nucleotides. In some embodiments, the emulsion is formed in a single reaction vessel. Optionally, the sequences of the different polynucleotide templates are the same or different. Optionally, a first microreactor includes a first polynucleotide template and a second microreactor includes a second polynucleotide template. Optionally, the first and the second polynucleotide templates comprise the same or different sequences. In some embodiments, the at least two microreactors of the plurality include a plurality of supports. Optionally, at least one of the plurality of supports is linked to a plurality of first primers (e.g., forward amplification primers). Optionally, the reaction mixture further includes a plurality of a second primer (e.g., reverse amplification primers). In some embodiments, at least one of the plurality of supports further includes a plurality of second primers. In some embodiments, at least one of the plurality of supports includes a plurality of first and second primers. In some embodiments, the first and second primers comprise the same sequences. In some embodiments, the first and second primers comprise different sequences. In some embodiments, the hydrophilic phase includes a reaction mixture. In some embodiments, the reaction mixture comprises a plurality of polynucleotide templates, a plurality of supports and a recombinase. In some embodiments, methods for nucleic acid synthesis further comprise subjecting the emulsion (e.g., including the reaction mixture) to isothermal amplification conditions, thereby generating a plurality of substantially monoclonal nucleic acid populations. In some embodiments, the plurality of substantially monoclonal nucleic acid populations is attached to the plurality of supports. In some embodiments, the nucleic acid synthesis method further includes recovering from the reaction mixture at least some of the supports attached to substantially nucleic acid monoclonal populations. In some embodiments, the nucleic acid synthesis method further includes depositing onto a surface at least some of the supports attached to the substantially monoclonal nucleic acid populations. In some embodiments, the nucleic acid synthesis method further includes forming an array by depositing onto a surface at least some of the supports attached to the substantially monoclonal nucleic acid populations. In some embodiments, the nucleic acid synthesis method further includes sequencing at least one substantially monoclonal nucleic acid population attached to the support. In some embodiments, the support comprises a bead, particle, a planar surface, or an interior wall of a channel or tube. In some embodiments, the reaction mixture further includes a polymerase and a plurality of nucleotides. In some embodiments, the polymerase comprises a strand displacing polymerase.

The section headings used herein are for organizational purposes only and are not to be construed as limiting the described subject matter in any way.

All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control.

It will be appreciated that there is an implied "about" prior to the temperatures, concentrations, times, etc., discussed in the present teachings, such that slight and insubstantial deviations are within the scope of the present teachings herein.

Unless otherwise required by context, singular terms shall include pluralities and plural terms shall include the singular.

The use of "comprise", "comprises", "comprising", "contain", "contains", "containing", "include", "includes", and "including" are not intended to be limiting.

It is to be understood that both the foregoing general description and the following detailed description are exemplary and explanatory only and are not restrictive of the invention.

Unless otherwise defined, scientific and technical terms used in connection with the present teachings described herein shall have the meanings that are commonly understood by those of ordinary skill in the art. Generally, nomenclatures utilized in connection with, and techniques of, cell and tissue culture, molecular biology, and protein and oligo- or polynucleotide chemistry and hybridization described herein are those well-known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques described herein are those well-known and commonly used in the art.

As utilized in accordance with exemplary embodiments provided herein, the following terms, unless otherwise indicated, shall be understood to have the following meanings:

The term "monoclonal" and its variants, when used in reference to one or more polynucleotide populations, refers to a population of polynucleotides where at least 90% of the members of the population share at least 90% identity at the nucleotide sequence level. As used herein, the phrase "substantially monoclonal" and its variants, when used in reference to one or more polynucleotide populations, refer to one or more polynucleotide populations wherein an amplified template polynucleotide molecule is the single largest polynucleotide in the population. Accordingly, all members of a monoclonal or substantially monoclonal population need not be completely identical or complementary to each other. For example, different portions of a polynucleotide template can become amplified or replicated to produce the members of the resulting monoclonal population; similarly, a certain number of "errors" and/or incomplete extensions may occur during amplification of the original template, thereby generating a monoclonal or substantially monoclonal population whose individual members can exhibit sequence variability amongst themselves. In some embodiments, a low or insubstantial level of mixing of non-homologous polynucleotides may occur during nucleic acid amplification reactions disclosed herein, and thus a substantially monoclonal population may contain a minority of diverse polynucleotides (e.g., less than 30%, less than 20%, less than 10%, less than 5%, less than 1%, less than 0.5%, less than 0.1%, or less than 0.001%, of diverse polynucleotides). In certain examples, at least 90% of the polynucleotides in the population are at least 90% identical to the original single template used as a basis for clonal amplification to produce the substantially monoclonal population. In some embodiments, methods for clonally amplifying provided herein, yield a population of polynucleotides wherein at least 50%, 60%, 70%, 75%, 80%, 85%, 90%, 91%, 92%, 93%, 94%, 95%, 96%, 97%, 98%, 99%, or 100% of the members of a population of polynucleotides share at least 80%, 85%, 90%, 95%, 96%, 97%, 98%, 99%, or 100% sequence identity to the template nucleic acid from which the population was generated. In some embodiments, methods for clonally amplifying provided herein, yield a population of polynucleotides in which a large enough fraction of the polynucleotides share enough sequence identity to allow sequencing of at least a portion of the amplified template using a high throughput sequencing system.

In some embodiments, at least 50%, 60%, 70%, 75%, 80%, 90%, 95%, or 99%, of the members of the amplicon will share greater than 90%, 95%, 97%, 99%, or 100% identity with the polynucleotide template. In some embodiments, members of a nucleic acid population produced using methods provided herein, can hybridize to each other under high stringency hybridization conditions.

In some embodiments, methods provided herein generate a population of polynucleotides that includes sufficiently few polyclonal contaminants to be successfully sequenced in a high throughput sequencing method. For example, methods provided herein can generate a population of polynucleotides that produces a signal (e.g., a sequencing signal, a nucleotide incorporation signal and the like) that can be detected using a particular sequencing system. Optionally, the signal can subsequently be analyzed to correctly determine the sequence and/or base identity of any one or more nucleotides present within any polynucleotide of the population. Examples of suitable sequencing systems for detection and/or analysis of such signals include the Ion Torrent sequencing systems, such as the Ion Torrent PGM™ sequence systems, including the 314, 316 and 318 systems, the Ion Torrent Proton™ sequencing systems, including Proton I, (Life Technologies, Carlsbad, CA) and the Ion Torrent Proton™ sequencing systems, including Ion S5 and S5XL (Thermo Fisher Scientific, CA). In some embodiments, the monoclonal amplicon permits the accurate sequencing of at least 5 contiguous nucleotide residues on an Ion Torrent sequencing system.

As used herein, the term "clonal amplification" and its variants refer to any process whereby a substantially monoclonal polynucleotide population is produced via amplification of a polynucleotide template. In some embodiments of clonal amplification, two or more polynucleotide templates are amplified to produce at least two substantially monoclonal polynucleotide populations.

As used herein, a "blocked primer" or a "3'-blocked primer" cannot be extended by a polymerase. Typically, a 3'-OH is missing or a chemical moiety is used to block polymerase extension. For example, the primer may have 3'-phosphate, 3' biotin, 3' amine, C3 spacer (3' Propyl), Spacer 9/18 either at the 3' end or close to it, 1',2'-Dideoxyribose (dSpacer), 3' Hexanediol, 2'-3'-Dideoxy, 3'-deoxy bases, inverted dT (see modified bases and spacers by IDT), 3'-amine or any other moiety that disables polymerase extension, see for example Table 2 in Lin-Ling et al. "Single-base discrimination mediated by proofreading inert allele specific primers", *J. Biochem Mol. Biol.* 2005 Jan. 31; 38(1):24-7.

As used herein, a "ribobase" means one or more nucleotides that are cleavable by an RNase H enzyme. The ribobase can be an rU, rA, rC, or rG, as non-limiting examples.

In some embodiments, the disclosure relates generally to methods, as well as related compositions and kits, for nucleic acid amplification, which includes cleaving with an endonuclease an oligonucleotide that is hybridized to a template nucleic acid. Cleaving the oligonucleotide can, optionally, be followed by an isothermal amplification reaction, especially recombinase-mediated amplification reactions such as RPA (recombinase-polymerase amplification). The methods and compositions use an oligonucleotide including a cleavable moiety, wherein the oligonucleotide is not extendable by a polymerase. That oligonucleotide is also referred to herein as a "blocked primer", wherein the cleavable moiety separates a 5' domain and 3' domain of the primer, and wherein an endonuclease, such as RNase H as disclosed herein, cleaves the primer at the cleavable moiety location removing the block. The 5' domain of the oligonucleotide remains hybridized to the template nucleic acid after the block is removed. Accordingly, the endonuclease cleaves or hydrolyzes a location or residue on the oligonucleotide when it is hybridized to a nucleic acid template. In some embodiments, the oligonucleotide and template nucleic acid form a DNA:DNA duplex. In further embodiments, the endonuclease does not cleave the oligonucleotide or blocked primer at other nucleotide positions besides the cleavable moiety.

In some embodiments, the cleavable moiety is one or more nucleotides that are cleavable by an RNase H enzyme, wherein the endonuclease is RNase H. Nucleotides cleavable by RNase H include ribobases rU, rA, rC, and rG, any of which may be present as a single ribobase or as two or more at the desired cleavage location in the oligonucleotide or blocked primer. In some embodiments, the RNase H enzyme is any RNase H enzyme disclosed herein, and is typically active at 37° C. and is other than a thermostable enzyme. In some embodiments, the RNase H enzyme is RNase II.

In some embodiments, the cleavable moiety is a site cleavable by an apurinic/apyrimidinic (AP) endonuclease when the oligonucleotide or blocked primer is hybridized to the nucleic acid template forming a double stranded duplex. An abasic, or baseless, site is cleavable by AP endonucleases and includes an apurinic site, an apyrimidinic site or a spacer. In some embodiments, AP endonucleases include Endonuclease IV (Endo IV), APE 1 or APE 2. See Example 6. In some embodiments, the endonuclease, including AP endonucleases, is an enzyme that is active at 37° C. and/or is other than a thermostable endonuclease.

The oligonucleotide or primer configuration can be any of those disclosed herein as to length of the 5' domain, length of the 3' domain and/or location of the cleavable moiety. In some embodiments, the first oligonucleotide or blocked primer is between 15 and 200, 15 and 150, 15 and 100, or 15 and 50 nucleotides long, and wherein the cleavable moiety is more than 5, 6, 7, 8, 9, 10, 11, 12, 13, 14, or 15 nucleotides away from the 3' terminus of the oligonucleotide. In some embodiments, the blocked oligonucleotide primer (e.g. first or second oligonucleotide; forward or reverse primer) includes a 5' domain and a 3' domain separated by the one or more nucleotides that are cleavable by RNase H, wherein the 5' domain is 10 to 50 nucleotides in length and the 3' domain is 10 to 50 nucleotides in length. In some embodiments, the RNase H enzyme is RNase 1-111.

In some embodiments, the first oligonucleotide is between 15 and 200 nucleotides long, and wherein the abasic site or spacer is more than 5 nucleotides away from the 3' terminus of the oligonucleotide. In some embodiments, the blocked oligonucleotide primer includes a 5' domain and a 3' domain separated by an abasic site or spacer that is cleavable by an AP endonuclease, wherein the 5' domain is 10 to 50 nucleotides in length and the 3' domain is 10 to 50 nucleotides in length. In some embodiments, the AP endonuclease is Endo IV or APE 1.

In some embodiments, the first oligonucleotide is a universal primer, wherein the universal primer can include any of the primer configurations disclosed herein. In some embodiments, the method of cleaving a hybridized oligonucleotide includes the use of both a first and second oligonucleotide, e.g. a forward and reverse primer that bind to complementary strands of the template nucleic acid in reverse orientation. In some embodiments, the reaction mixture further includes a second oligonucleotide that binds to the target nucleic acid on a complementary strand to the first binding site and in a reverse orientation, and wherein the second oligonucleotide is not extendable by the polymerase.

In some embodiments, the method of cleaving a double stranded template nucleic acid is carried out according to the following steps: forming a reaction mixture comprising the template nucleic acid and a first oligonucleotide comprising a cleavable moiety, wherein the first oligonucleotide is not extendable by a polymerase; exposing the reaction mixture to an endonuclease enzyme in the presence of reaction conditions permissive for hybridization between the first oligonucleotide and a first binding site on the template nucleic acid, wherein at least a portion of the first oligonucleotide hybridizes to the template; and cleaving the first oligonucleotide at the cleavable moiety with the endonuclease, wherein the endonuclease cleaves the oligonucleotide more efficiently at 37° C. than at 60° C., wherein the cleavage step occurs at a temperature below 42° C., or a combination thereof.

In some embodiments, the endonuclease cleaves a significant fraction of the first oligonucleotide present in the reaction mixture within 30 or 60 minutes of exposing the hybridized primer and template nucleic acid to the endonuclease. To determine whether the endonuclease cleaves a significant fraction of oligonucleotides present, as a non-limiting example, the oligonucleotides before cleavage can be non-extendable by a polymerase wherein when the oligonucleotide is cleaved extension can occur and a product of the extension can be detected. In some embodiments, the nucleic acid template is a member of a polynucleotide library and the method is carried out on a plurality of nucleic acid templates of the polynucleotide library, wherein each member of the polynucleotide library comprises the first primer binding sequence. Accordingly, the method can be combined with amplification methods, such as RPA, wherein the reaction mixture further comprises recombinase and polymerase enzymes to amplify the target nucleic acid. The recombinase and polymerase enzyme can be any of those disclosed herein, and are typically other than thermo-stable enzymes. In some embodiments, the reaction mixture remains below 42° C. for both the cleavage and amplifica-tion. Accordingly, the cleavage and amplification are carried at a temperature below 42° C.

In some embodiments, the first primer is a universal primer, the reaction mixture is subject to amplification conditions, and at least two of the nucleic acid templates are amplified to form substantially monoclonal populations. The first primer can be immobilized on a solid support or the amplification method comprises bridge amplification or emulsion amplification. In some embodiments, the amplifi-cation is carried out for at least 10 cycles using the first oligonucleotide and the second oligonucleotide. In some embodiments, the cleavage and 10 cycles are carried out in less than 15, 30, or 60 minutes.

In some embodiments, provided herein are reaction mix-ture compositions, wherein the reaction mixture comprises a population of cleavable primers, wherein the population of cleavable primers comprises at least 10 primers that bind to at least 10 target binding sites on a mammalian genome, wherein the cleavable primers comprise a 5' domain and a 3' domain separated by one or more nucleotides that are cleavable by an RNase H, wherein the 5' domain is 10 to 50 nucleotides in length and the 3' domain is 10 to 50 nucleo-tides in length. In alternative embodiments, the reaction mixture comprises a population of cleavable primers, wherein the population of cleavable primers comprises at least 10 primers that bind to at least 10 target binding sites on a mammalian genome, wherein the cleavable primers comprise a 5' domain and a 3' domain separated by an abasic site or spacer that is cleavable by an AP endonuclease, wherein the 5' domain is 10 to 50 nucleotides in length and the 3' domain is 10 to 50 nucleotides in length. In some embodiments, the 3' domain of the cleavable primer is 14 to 25 nucleotides in length.

The reaction mixture compositions can further include a polymerase, a recombinase or both. Those enzymes can be any of those disclosed herein and are typically active at 37° C. and/or other than thermostable enzymes. In some embodiments, the population comprises at least 100 cleav-able primers that are not extendable by a polymerase or wherein the population comprises at least 1000 cleavable primers that are not extendable by a polymerase.

Those skilled in the art can devise many modifications and other embodiments within the scope and spirit of the disclosed inventions. Indeed, variations in the materials, methods, drawings, experiments examples and embodi-ments described may be made by skilled artisans without changing the fundamental aspects of the disclosed inven-tions. Any of the disclosed embodiments can be used in combination with any other disclosed embodiment.

EXAMPLES

The following examples are put forth so as to provide those of ordinary skill in the art with a complete disclosure and description of how to use the embodiments provided herein, and are not intended to limit the scope of the disclosure nor are they intended to represent that the Examples below are all of the experiments or the only experiments performed. Efforts have been made to ensure accuracy with respect to numbers used (e.g. amounts, tem-perature, etc.) but some experimental errors and deviations should be accounted for. Unless indicated otherwise, parts are parts by volume, and temperature is in degrees Centi-grade. It should be understood that variations in the methods as described can be made without changing the fundamental aspects that the Examples are meant to illustrate.

Example 1: Screening of RNase H Cleavable 3' Blocked Primer Configurations for Use in a Recombinase Polymerase Amplification Reaction Experiments were performed that analyzed configurations for blocked forward primers and blocked reverse primers for use in methods for performing recombinase polymerase amplification of a nucleic acid template under isothermal amplification conditions. Configurations analyzed in these experiments included the length of the 3' domain of the blocked forward and reverse primers and the identity of the ribobase, which is the site of RNase H cleavage located between the 5' domain and 3' domain of the 3' blocked primers. See FIG. 2 for a diagram of the 3' blocked primers and the different configurations analyzed in these Examples.

Recombinase polymerase amplification (RPA) reactions were performed using the following protocol in a single reaction vessel with a single continuous liquid phase in a total reaction volume of ~50 μL:

The recombinase source was from a TwistAmp® Basic kit (TwistDx®). Cambridge, Great Britain). Dehydrated pellets in the kit contain uvsX recombinase, uvsY recombinase loading protein, gp32 protein, Sau DNA polymerase, dNTPs, ATP, phosphocreatine and creatine kinase. One pellet from a TwistAmp® Basic kit was rehydrated in 29.5 μL of Rehydration buffer supplied from the kit in a 0.2 μL PCR tube. The recombinase solution was vortexed and spun, then iced.

The template DNA (at various concentrations) in a vol-ume of 0.5 μL was added to the reaction tube, vortexed and then spun. The template DNA was either a genomic DNA, or a DNA library made with adapters for amplification.

The 3' blocked primers with a single ribobase were synthesized by IDT (Coralville, IA) in various configura-tions of long and short 5' and 3' domains designated as V1-V6. See FIG. 2 and FIG. 10. A long 5' domain is greater than 25 nucleotides in length and a long 3' domain is equal to, or greater than 14 nucleotides in length, whereas a short 5' domain is 15-25 nucleotides in length, and a short 3' domain is 4-6 nucleotides in length. The medium length 3' domain tested was 10 nucleotides in length. In these experi-ments the 3' blocking group was a 3'-C3 spacer, but it is understood that other 3'-blocking groups such as a phos-phate, biotin, amine, etc. can be used with the 3' blocked primer.

Forward and reverse primers (various amount of 10 uM stocks) and RNase HII (NEB, Ipswich, MA; various unit amount) were added to the reaction tube. Additional low-TE buffer (10 mM Tris-HCl, 0.1 mM EDTA, pH 8.0) was added to top off the total volume to 42.5 μL. The recombinase reaction mix was vortexed, spun, and placed on ice. Next, 7.5 μL of 54 mM Mg-acetate was added to the inside lid surface of the PCR tube containing the recombinase reac-tion. The PCR tube was closed, then vortexed and spun, and incubated in a total 50 µL volume at 37° C., for 30 min to 50 minutes in the thermocycler. The reaction was stopped by adding EDTA at 20 mM final concentration, then purified with PureLink® PCR Purification kit (Thermo Fisher Scientific, Waltham, MA). Amplified product was eluted in 50 µL elution buffer supplied in the kit. A portion of the product was assessed on E-Gel® EX Agarose Gels, 2% (Thermo Fisher Scientific, Waltham, MA) containing a nucleic acid stain, such as SYBRGOLD.

Two separate experiments were conducted to determine the optimal 5' and 3' domain length as well as the choice of ribobase for the RPA reaction. The product from the above RPA reaction was obtained using 1 pM of template (100 bp insert library with a tailed-A (57 bp) and P1B (53 bp) adapters with an expected amplicon size of about 210 bp), 400 nm each of 3' blocked primers and 8 mM of Mg-acetate, wherein 15 µL of the 504, purified RPA reaction product was loaded into wells of the agarose gels and the DNA fragments separated by electrophoresis. See FIGS. 3-5 and Tables 1-2.

Figure 2:
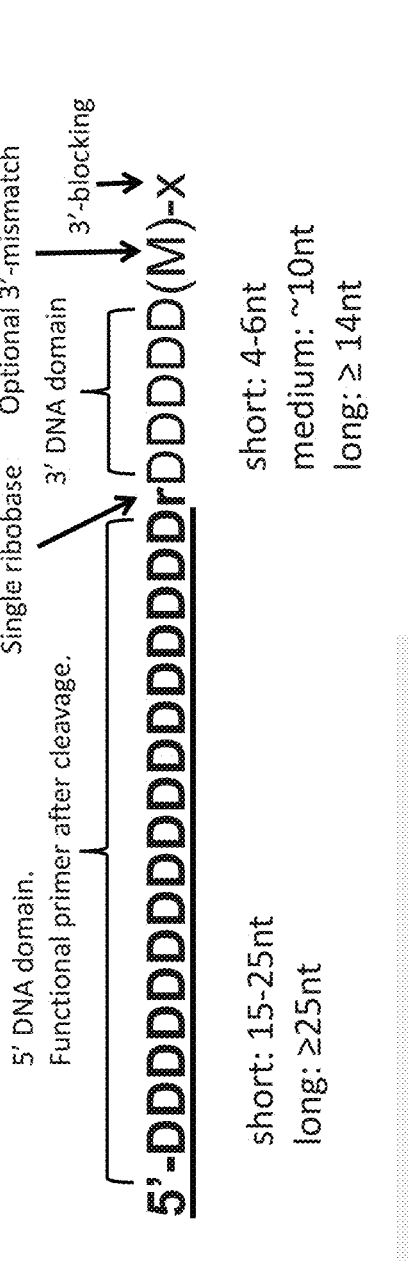
FIG. 2 is a non-limiting schematic of blocked primers and exemplary primer configurations, including exemplary 5' domain and 3' domain lengths.
Figure 3:
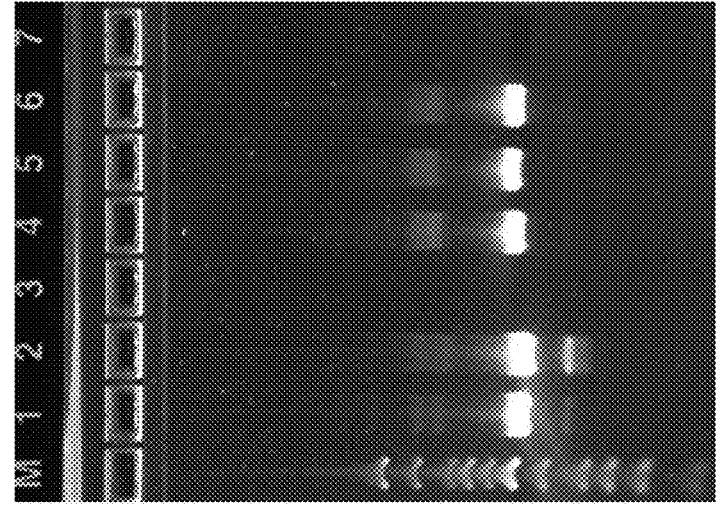
FIG. 3 is a photo of a gel showing the results of blocked primer configuration screening with V1, V2 and V3 primers by comparing DNA template amplification using the blocked primers.

Table 1 provides the tested primer designs wherein V1 (short 5' domain and short 3' domain), V2 (long 5' domain and long 3' domain) and V3 (long 5' domain and short 3' domain) correspond to the 3' blocked primers of FIG. 2 and the ribobase is cysteine (rC) or uracil (rU). MM is a mismatched base following the 3' domain. See FIG. 3 for the gel that corresponds to Table 1.

TABLE 1

Configurations for screening V1, V2 and V3 primer designs

| Lane | Primer configuration | Results |
|---|---|---|
| M | NEB Low MW ladder | N/A |
| 1 | Regular short (20mer) primers | Significant primer dimers (nonspecific bands) |
| 2 | Regular long (46-53mer) primers | Significant primer dimers (nonspecific bands) |
| 3 | 3' blocked primers. V1-rC | No detectable results |
| 4 | 3' blocked primers. V2-rC | Amplification band present with no primer dimers |
| 5 | 3' blocked primers. V2-MM-rC | Amplification band present with no primer dimers |
| 6 | 3' blocked primers. V2-rU | Amplification band present with no primer dimers |
| 7 | 3' blocked primers. V3 | No detectable product band |

The results from the use of the V2 primer configuration indicated the choice of ribobase is not critical and that the presence of a 3' mismatch base is optional. In comparing the primer configurations of V1, V2 and V3 the results indicated a short (4-6 nucleotides) 3' domain was inefficient in amplifying nucleic acid under the RPA reaction conditions analyzed in this experiment, with either a long or short 5' domain. However, surprisingly, a relatively long (≥14 nucleotides) 3' domain with a long 5' domain resulted in efficient amplification of template DNA. Accordingly, in some embodiments, the methods for amplifying a nucleic acid template provided herein, include a 3' blocked primer that includes a 5' domain and a 3' domain separated by a ribobase, wherein the 3' domain is ≥14 nucleotides in length, such as 14 to 30 nucleotides in length.

To further elucidate the configuration of 5' and 3' domain length, a comparison between V4 (long 5' domain and medium 3' domain) and V5 (short 5' domain and long 3' domain) was performed. Table 2 provides the tested primers wherein V4 and V5 correspond to the 3' blocked primers of FIG. 2 and the ribobase is guanine (rG) or uracil (rU). See FIGS. 4 and 5 for the gels that corresponds to Table 2; the gel of FIG. 5 was exposed for a longer period of time to the detection reagent resulting in the detection of a weak product band in lane 3 (V4-rU).

TABLE 2

Primer configuration screening for V4 and V5 as compared to V2-rU

| Lane | Primer configuration | Results |
|---|---|---|
| M | NEB Low MW ladder | N/A |
| 1 | 3' blocked primers. V2-rU | Amplification band present with no primer dimers |
| 2 | 3' blocked primers. V5-rG/rU | Amplification band present with no primer dimers |
| 3 | 3' blocked primers. V4-rU | Weak (FIG. 5) or no detectable (FIG. 4) amplification product band with no primer dimers |

Figure 5:
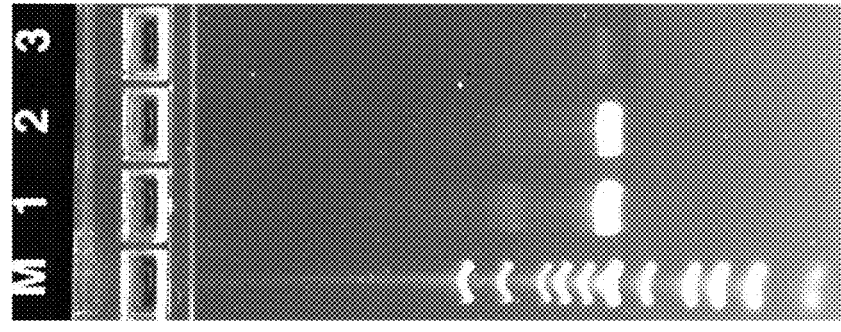
FIG. 5 is a photo of a gel showing the results of blocked primer configuration screening with V4 and V5 primers by comparing DNA template amplification using the blocked prime with longer exposure to detection reagent.

The results of the comparison between V4 and V5 indicated: 1) due to the presence of a weak band in FIG. 5 for V4, that there was some amplification where the 3' domain of the 3' blocked primer had a length of 10 nucleotides, in embodiments less than 14 nucleotides but more than 6 nucleotides; and, 2) a long 3' domain (≥14 nucleotides) efficiently amplified DNA in the RPA reaction with a 5' domain of 15 nucleotides or greater. Accordingly, in some embodiments, the methods for amplifying a nucleic acid template provided herein, include a 3' blocked primer that includes a 5' domain and a 3' domain separated by a ribobase, wherein the length of the 3' domain is equal to or greater than 7, 8, 9, 10, 11, 12, 13 or 14 nucleotides on the low end of the range and equal to or less than 10, 11, 12, 13, 14, 15, 20, 25, 30, 35, 40, 45, or 50 nucleotides on the high end of the range. In embodiments the length of the 3' domain is from about 7 to 25, about 10 to 25 or about 14 to 25 nucleotides and the length of 5' domain is from about 15 to 60, about 15 to 40 or about 15 to 25 nucleotides.

The results of these experiments indicated efficient amplification using 3' blocked primers with a 5' DNA domain equal to or greater than (≥) 15nt and 3' DNA domain equal to or greater than (≥) 14nt (excluding any possible 3' mismatched nucleotides). The cleaved 3' domain by RNase H enzyme is greater than or equal to (≥) 15 nucleotides when including the ribobase in the length. The ribobases uracil, guanine and adenine are approximately equivalent but the interaction between RNase H enzyme and cysteine ribobase may result in slower kinetics under certain reaction conditions. In the experiments described herein, the primers V2 and V5 produced amplification product with no detectable nonspecific amplification. Accordingly, in some embodiments, the methods for amplifying a nucleic acid template provided herein, include a 3' blocked primer that includes a 5' domain and a 3' domain separated by a ribobase, wherein the 5' domain is at least 25 nucleotides in length and the 3' domain is at least 14 nucleotides in length. In some embodiments, the 5' domain of the 3' blocked primer is 15-25 nucleotides in length and the 3' domain is at least 14 nucleotides in length. In some embodiments, the length of 5' domain is at least 15 nucleotides and the length of the 3' domain is at least 14 nucleotides. In yet other embodiments, the methods for amplifying a nucleic acid template provided herein, include a 3' blocked primer that includes a 5' domain and a 3' domain separated by a ribobase, wherein the 5' domain is 15 to 50 nucleotides in length and the 3' domain is 14 to 50 nucleotides in length.

Example 2: Use of RNase H Cleavable 3' Blocked Primer in a Recombinase Polymerase Amplification Reaction Reduces Nonspecific Product Formation Experiments were performed that analyzed the efficiency of the blocked forward primers and blocked reverse primers for use in methods for performing recombinase polymerase amplification of a nucleic acid template under isothermal amplification conditions as compared to standard (non-blocked) primers and the amplification of nonspecific DNA such as primer dimers. The results illustrate that the cleavable 3' blocked primers provided herein reduce or eliminate primer dimer formation in RPA methods.

First, 3' blocked primers (forward and reverse) demonstrated an ability to reduce nonspecific product amplification in a control reaction performed in the absence of template DNA, as compared to standard (non-blocked) short and long primers. The RPA reaction was carried out as described in Example 1 except that no template was included in the reaction mixture, which included 400 nm each of 3' blocked primers, with or without RNase HII enzyme, and 8 mM of Mg-acetate, wherein 15 µL of the 504, purified RPA reaction product was loaded into wells of the agarose gel and the DNA fragments separated by electrophoresis. See FIG. 6 and Table 3.

Non-specific amplification was tested in a no template control reaction. 3' blocked primers (V2-rU design) were compared to standard (non-blocked) long and short primers and V2-rU (long 5' domain and long 3' domain) (Table 3). The results are shown on FIG. 6. Regular (unblocked) primers produced significant amounts of spurious amplification products in the no template control reactions. On the other hand, using the V2-rU 3' blocked primers, only minimal nonspecific products were detected.

TABLE 3

| | Reduced non-speific amplification product with V2-rU as compared to non-blocked primers | |
|---|---|---|
| Lane | Primer configuration | Results |
| M | NEB Low MW ladder | N/A |
| 8 | NTC: Standard short primers | Nonspecific amplification product present |
| 9 | NTC: Standard long primers | Nonspecific amplification product present |
| 10 | NTC: 3' blocked primers V2-rU | Minimal nonspecific amplification product |

Next, the formation of nonspecific products such as primer dimers was analyzed with the use of 3' blocked primers compared to standard (non-blocked) primers wherein the 3' blocked primers were designed to have functional primers after cleavage (by RNase H enzyme) that match and have the same sequence as the standard primers used in the RPA reaction. Recombinase polymerase amplification (RPA) was performed using 100 ng of template (*E. coli* genomic DNA), 480 nm each of blocked and standard primers (SEQ ID Nos:2-5), RNase H enzyme and 8 mM of Mg-acetate, wherein 5 or 15 µL of the 500_, purified RPA reaction product was loaded into wells of the agarose gel, and the DNA fragments were separated by electrophoresis. See FIG. 7 and Table 4.

The following standard (non-blocked) primers were used:

```
268-Forward primer:
                                (SEQ ID NO: 2)
ACA CGG TCC ADA CTC CTA CGG GAG GCA GCA
(e.g., where according to IUPAC "D" is
selected at random from A, T or G).

268-Reverse primer:
                                (SEQ ID NO: 3)
GCG GCT GCT GGC ACG GAG TTA GCC GGT GCT
```

The following 3' blocked primers, wherein the underlined sequence is identical to the corresponding forward or reverse standard (non-blocked) primer after cleavage, were used:

```
268-Forward primer-rG:
                                (SEQ ID NO: 4)
ACA CGG TCC ADA CTC CTA CGG GAG GCA GCA rGTG GGG AAT ATT GCA C-block 268-Reverse primer-rU:
                                (SEQ ID NO: 5)
GCG GCT GCT GGC ACG GAG TTA GCC GGT GCT rUCT TCT GCG GGT AAC G-block
```

The following *E. coli* amplicon 268 was generated from template gDNA (202 bp) as a result of the RPA reaction:

```
                                (SEQ ID NO: 1)
ACA CGG TCC AGA CTC CTA CGG GAG GCA GCA GTG GGG

AAT ATT GCA CAA TGG GCG CAA GCC TGA TGC AGC CAT

GCC GCG TGT ATG AAG AAG GCC TTC GGG TTG TAA AGT

ACT TTC AGC GGG GAG GAA GGG AGT AAA GTT AAT ACC

TTT GCT CAT TGA CGT TAC CCG CAG AAG AAG CAC CGG

CTA ACT CCG TGC CAG CAG CCG C
```

Table 4 provides the tested primers, standard primers and 3' blocked primers wherein the 5' domain was 30 nucleotides in length and the 3' domain was 15 nucleotides in length. Each RPA product was loaded at 5 µl and 15 µl in two wells, respectively. See FIG. 7 for the gel that corresponds to Table 4.

TABLE 4

| | 3' Blocked primers eliminate primer dimer product in gDNA amplification as compared to standard (non-blocked) primers. | |
|---|---|---|
| Lane | Primer & Exp. Configuration | Results |
| M | NEB low molecular weight ladder | N/A |
| 1 | Standard primers; 5 µL loaded | Primer dimer product and amplification product present |
| 2 | 3' blocked primers; with RNaseH enzyme; 5 µL loaded | No detectable primer dimer product; amplification product present |
| 3 | 3' blocked primers; No RNaseH enzyme control; 5 µL loaded | No detectable primer dimer product or amplification product |
| 4 | Standard primers; 15 µL loaded | Primer dimer product and amplification product present |
| 5 | 3' blocked primers; with RNaseH enzyme; 15 µL loaded | No detectable primer dimer product; amplification product present |

US 12,571,016 B2

69 70

TABLE 4-continued

3' Blocked primers eliminate primer dimer product in gDNA amplification
as compared to standard (non-blocked) primers.

| Lane | Primer & Exp. Configuration | Results |
|------|------------------------------|---------|
| 6 | 3' blocked primers; No RNaseH enzyme control; 15 μL loaded | No detectable primer dimer product or amplification product |

Figure 7:
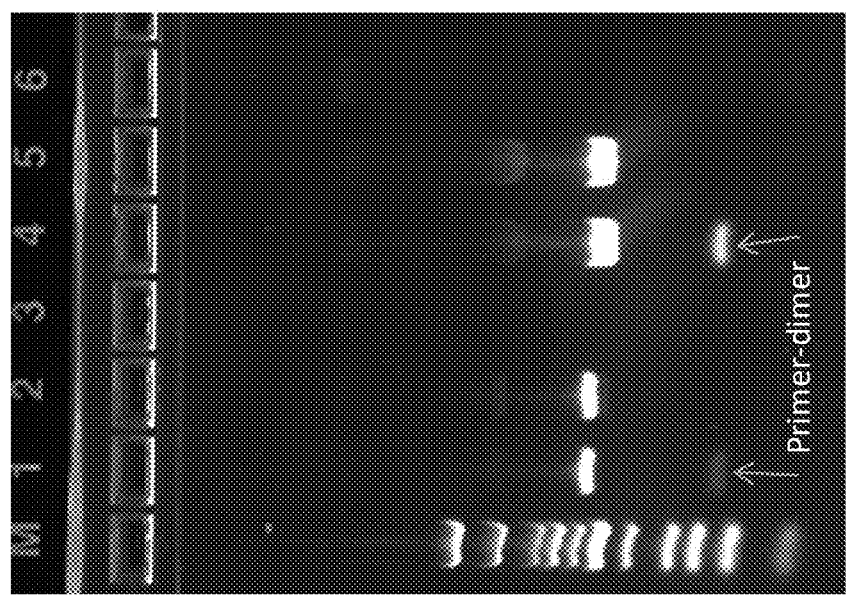
FIG. 7 is a photo of a gel showing the results of DNA template amplification wherein nonspecific amplification is reduced or eliminated using blocked primers of the invention.

As shown in FIG. 7, amplification using standard (non-blocked) RPA primers under these conditions, generated detectable primer dimers. On the other hand, primer dimers were not detectable after amplification using the 3' blocked primers of the invention, having a 5' domain after cleavage, that contains the same sequence as the standard primers. Furthermore, primer dimers were not detected when the 3' blocked primers were uncleaved (no RNase H enzyme), and therefore fail to produce detectable amplification product. Accordingly, this experiment demonstrates that the blocked forward primers and blocked reverse primers when used in methods for performing recombinase polymerase amplification of a nucleic acid template under isothermal amplification conditions efficiently amplify template DNA without substantially generating nonspecific product such as primer dimer product.

Example 3: Titration of RNase H Enzyme for Use in a Recombinase Polymerase Amplification Reaction with RNase H Cleavable 3' Blocked Primers Experiments were performed that analyzed various amounts of RNase H enzyme, including a "prohibiting" amount, a "limiting" amount and an "excess" amount for use in the methods for performing recombinase polymerase amplification of a nucleic acid template under isothermal amplification conditions with the blocked forward primers and blocked reverse primers. Not to be limited by theory, in the initial stage of amplification where low copies of template DNA is present, primer-template duplex "D-loop" is considered a rare event. A certain amount of RNase H enzyme is required to cleave the duplex to activate the primer before the D-loop dissociates. If RNase H enzyme is too low, the chance of an RNase enzyme interacting with a blocked primer bound to a template may become mathematically impossible so that amplification does not progress. In that instance, the RNase H enzyme is considered to be a "prohibiting" amount. When more RNase H enzyme is present, cleavage of the template-bound blocked primer becomes possible and more efficient, while still not fully efficient. In that instance, amplification progresses at a reduced rate, although such an amplification reaction can still achieve sufficient amplification product if allowed a longer reaction time. In that instance, the RNase H enzyme is considered a "limiting" amount. An "excess" amount of the RNase H enzyme ensures the RPA reaction proceeds based on the kinetics of the polymerase and other components in the reaction mixture and not the enzyme needed to remove the blocking group, which would otherwise be a rate limiting step for primer extension. In that instance, RNase H enzyme is present in an amount to guarantee full cleavage of the ribase-containing primer, and is "non-limiting"; RNase H enzyme will not slow down or diminish amplification as compared to a "prohibiting" or "limiting" amount of enzyme. In some embodiments, the RNase H enzyme is present in the RPA reaction mixture in an excess amount.

The titration experiments described herein empirically determine an excess amount of RNase HII enzyme with the V2 and V5 3' blocked primer configurations of the invention in the RPA methods for amplifying DNA template.

The RPA experiment was conducted following the methods of Example 1 using template library DNA (100 bp insert library with a tailed-A (57 bp) and P1B (53 bp) adapters with an expected amplicon size of about 210 bp) and 400 nm each of 3' blocked primers (V2-rU). The amplification reaction was performed at 37° C. for 50 minutes. The RNase HII was concentrated 20× from the original 5 U/uL concentration. 100 U in a 1 uL volume (20× concentrate) was tested as compared to 5-20 U in a 1-4 uL volume (standard concentration from NEB).

FIG. 8A provides the identity of samples loaded onto gels the tested RNase H enzyme and the 3' blocked primers (V2-rU) wherein the 5' domain is 25 nucleotides in length and the 3' domain is 14 nucleotides in length. Each RPA product was loaded at 150 in a wells of the gel. As shown in FIG. 8A, when amplified for 50 minutes, as low as 5 U of RNase HII produced detectable product with exemplified V2-rU 3' blocked primer configuration. All concentrations of RNase HII enzyme used produced detectable product, with increasing amounts of RNase HII enzyme yielding more product, as seen with brighter product bands, however the RNase H enzyme is saturated at 20 U, i.e. an excess amount. RNase H enzyme above 20 U, including up to 200 U had no detrimental effect on the product produced. In the control lane with 3' blocked primers and no RNase HII enzyme, no product was detected. Of note, in the control lane with standard non-blocked primers (and no RNase HII) nonspecific product bands were detected confirming results observed in Example 2.

In this experiment, based on the intensity of the product bands, 5-10 U of RNase HII enzyme is considered limiting for the V2 primer configuration in a 50 minute reaction while 20 U-200 U is considered in excess.

Titration of RNase H enzyme was further analyzed with primer configurations V2-rU, V2-rC and V5. FIG. 8B provides the identity of samples loaded onto gels, the tested RNase H enzyme and the type of 3' blocked primers. Each RPA product was loaded at 10 μl in wells of the gel. As shown in FIG. 8B, when amplified for 50 minutes, as low as 5 U of RNase HII produced detectable product with exemplified V2-rU and V2-rC 3' blocked primer configuration (lanes 3 and 6, respectively) but is "prohibiting" at 2.5 U wherein no detectible product band was generated (lanes 2, 5 and 8). In this experiment, 5-10 U of RNase HII enzyme is considered "limiting" for the V2 primer configuration in a 50 minute reaction based on the intensity of the product bands.

While relatively less efficient under other limiting reaction conditions (e.g. shorter reaction time), ribase rC (lanes 5-7) performed similarly to rU primers (lanes 2-4) in V2 configurations in amount of product generated. Accordingly, in some embodiments the ribase in the 3' blocked primers can be rC. The V5 primer with short 5' domain (lanes 8-9) is less efficient as compared to V2, and may require more RNase HII to achieve a similar level of amplification under similar reaction condition. In this experiment, 2.5-5 U of RNase H enzyme is considered "prohibiting" and 10 U is considered "limiting" for V5 primer configuration in a 50 minute reaction based on the intensity of the product bands.

For the control (lane 1) of non-blocked standard primers with no RNase HII enzyme, significant non-specific product bands were observed.

RNase H enzyme was further analyzed at different amplification reaction temperatures to determine an optimal temperature range for RNase HII enzyme.

Figure 8C:
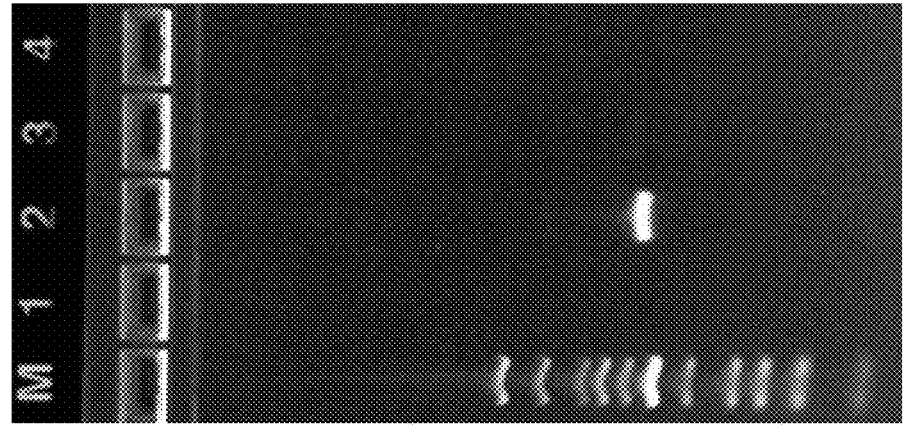
FIG. 8C is a photo of a gel showing the results of DNA amplification with a range of amplification reaction temperatures.

The RPA experiment was conducted following the methods of Example 1 using 400 nm each of 3' blocked primers (V2-rU) and 10 U in a 2 μL volume of RNase HII from NEB, wherein the reaction was incubated from a range of 37° C. to 42° C. for 50 minutes. Each RPA product was loaded at 5 μl in a wells of the gel. FIG. 8C provides the identity of samples loaded onto gels, the tested RNase H enzyme, the 3' blocked primers and reaction temperature. As shown in FIG. 8C, RNase HII performs optimally at 37° C., with a faint band present in lane 3 (40° C. reaction temperature) and no product band visible in lane 4 (42° C. reaction temperature). As will be appreciated, different RNase H enzymes may perform optimally at different temperatures and such conditions may be empirically determined with the 3' blocked primers in the RPA amplification methods.

Example 4: Use of Alternative Reaction Mixture in Recombinase Polymerase Amplification Reaction with RNase H Cleavable 3' Blocked Primers RPA experiments were performed that analyzed an exemplary alternative base RPA reaction mixture formulation as compared to the base reaction mixture in the Examples above, which were formed by hydrating a commercially available pellet (TwistDx®, Cambridge, Great Britain), adding blocked forward and reverse primers, RNase HII, additional low-TE buffer, and Mg-acetate.

Reaction mixtures prepared using commercially available pellets from TwistDx contain uvsX recombinase, uvsY recombinase loading protein, gp32 protein, Sau DNA polymerase, dNTPs, ATP, phosphocreatine and creatine kinase. An exemplary alternative reaction mixture was prepared in pellet form, that included the same components as the commercially available reaction mixture above except that Sau polymerase was replaced with a mixture of Sau polymerase and a T7 DNA polymerase, with thioredoxin. After the reaction mixture pellet was hydrated, RNase H enzyme, and 3' blocked primers were added. Except for the reaction mixture modifications noted, the RPA reaction was performed as described in Example 1 using the 3' blocked primer configurations of V1, V2-rU, V2-rC, V2-MM-rC, and V3-rC. Standard (non-blocked) primers were used as a control.

The RPA reaction was performed following the protocol in Example 1 using 1 pM of template DNA (100 bp insert library with a tailed-A (57 bp) and P1B (53 bp) adapters with an expected amplicon size of about 210 bp), 400 nm each of primers, 45 U or 20 U RNase HII enzyme (with 3' blocked primers) and 8 mM of Mg-acetate. After the reaction was performed and stopped, 15 uL of the 50 uL purified RPA reaction product was loaded into wells of the agarose gel and the DNA fragments were separated by electrophoresis.

Table 6 provides the identity of those samples loaded onto the gel. As seen in FIG. 9 and summarized in Table 6, amplification products of the expected size as well as primer dimers, were seen in amplifications using standard primers (lane 1). For the 3' blocked primers, results were similar exemplary alternative reaction reaction mixture to those obtained using the standard commercial reaction mixture. No reaction products were detectable in samples generated using V1 or V3 primers, which have the relatively short 3' domain, or samples with 20 U of RNase HII or a no RNase control. All other samples that were generated using 3' blocked primers contained the expected amplification product in detectable quantities.

TABLE 6

Pellet formulation is compatible and results in efficient DNA template amplification with the forward and reverse 3' blocked primers.

| Lane | Primer & Exp. Configuration | Results |
|------|------------------------------|---------|
| M | NEB Low MW ladder | N/A |
| 1 | Regular primers; TwistDx pellet control | Detectable amplification product and nonspecific amplification product |
| 2 | 3' blocked primers, V2-rU; TwistDx pellet control; 45U RNase H | Detectable amplification product |
| 3 | Regular primers; alternative exemplary RPA reaction mixture formulation; 45U RNase H | Detectable amplification product |
| 4 | 3' blocked primers, V1; alternative exemplary RPA reaction mixture formulation; 45U RNase H | No detectable amplification product |
| 5 | 3' blocked primers, V2-rC; alternative exemplary RPA reaction mixture formulation; 45U RNase H | Detectable amplification product |
| 6 | 3' blocked primers, V2-MM-rC; alternative exemplary RPA reaction mixture formulation; 45U RNase H | Detectable amplification product |
| 7 | 3' blocked primers, V3-rC; alternative exemplary RPA reaction mixture formulation; 45U RNase H | No detectable amplification product |
| 8 | 3' blocked primers, V2-rU; alternative exemplary RPA reaction mixture formulation; 45U RNase H | Detectable amplification product |
| 9 | 3' blocked primers, V2-rU; alternative exemplary RPA reaction mixture formulation; 20U RNaseH2 | No detectable amplification product |
| 10 | 3' blocked primers+, V2-rU; alternative exemplary RPA reaction mixture formulation; No RNase H (control) | No detectable amplification product |

In summary, the results confirmed that V1 and V3 primer configurations, which have a relatively short 3' domain (4-6 nucleotides) length are inefficient in amplifying template DNA, but that V2 primers with either the commercially available pellet and reaction mixture formulation or the alternative exemplary RPA pellet and reaction mixture formulation efficiently amplified the template DNA. Furthermore, the experiment illustrates the robustness of the 3' blocked primers to different base reaction mixture pellet and soluble reaction mixture formulations. Accordingly, In some embodiments, provided herein, is a reaction amplification method, such as RPA, performed using a dehydrated pellet formulation (which is rehydrated prior to use).

Example 5: Amplification of Template with RNase H Cleavable 3' Blocked Primers Attached to a Solid Support This example illustrates clonal amplification of a DNA template using a recombinase polymerase amplification reaction wherein at least one of the primers of a primer pair is a 3' blocked primer, wherein the 3' blocked primer is attached to a support. See FIG. 11 for exemplified primers of the invention, wherein the blocking group C3 spacer is represented as 3spC3 in the primer sequences. The 3spC3 spacer can include phosphoramidite (available from Integrated DNA Technologies, Coralville, Iowa).

As a non-limiting example, the RPA method can be performed essentially using the methods described in Example 1 in a single reaction vessel in a single continuous liquid phase, wherein a reverse 3' blocked primer with a V2 or V5 configuration is attached to a bead and the forward primer (3' blocked primer of the invention or standard non-blocked primer) is added in solution to the reaction mixture. Total reaction volume is 50 µL to 1.2 mL. The following discusses a reaction in 300 µL volume.

Beads, such as 1.25 µL from an 80 million/uL stock (100 million beads) with the attached reverse primer are added in a 1.5 mL tube (tube 1). The required bead count can vary depending on the sequencing chip (provided the bead-primer-template-MgOAc mixture volume does not exceed 40% of the reaction volume) but is typically in the range from 20 million to 1 billion beads for a reaction scale of 50 µL, up to 2.4 mL. For example, the bead count used can be from 10 to 100 million/µL. A forward primer, standard or 3' blocked primer of the invention, (1.2 µL, of a 100 µM stock) is added to the bead tube (tube 1), followed by vortexing and spinning to a final concentration of 0.4 µM in the final reaction. The immobilized blocked reverse primer sequence can be one of the following:

```
                                    (SEQ ID NO: 6)
5'-CCT ATC CCC TGT GTG CCT TGG CAG TCT CAG

CCrU CTC TAT GGG CAG TCG A/3 SpC3/-3';

(SEQ ID NO: 7)
5'-CCA CTA CGC CTC CGC TTrU CCT CTC TAT GGG

CAG /3SpC3/;
or (SEQ ID NO: 8)
5'-C CTC CGC TTT CCT CTC TrAT GGG CAG TCG

GTG AT /3SpC3/.
```

The forward primer of a standard (non-blocked) configuration, or a 3' blocked primer with a V5 configuration, is added to the bead tube (tube 1), followed by vortexing and spinning. The solution forward primer sequence can be one of the following:

```
                                    (SEQ ID NO: 9)
5'-CCA TCT CAT CCC TGC GTG TC-3';

(SEQ ID NO: 10)
5'-CCA TCT CAT CCC TGC GTG TCT CCG AC-3';

(SEQ ID NO: 11)
5'-CCA TCT CAT CCC TGC rGTG TCT CCG ACT CAG

/3SpC3/;
or (SEQ ID NO: 12)
AAC GAT CCA TCT CAT CCC TGC rGTG TCT CCG ACT

CAG /3SpC3/
```

A biotinylated forward primer (0.12 uL of a 10 µM stock) is added to the bead tube (tube 1), followed by vortexing and spinning. The biotinylated forward primer sequence can be: 5'Bio-CCA TCT CAT CCC TGC GTG TC-3' (SEQ ID NO:13).

Various volumes of polynucleotide library (at 100 pM concentration) is added to the bead tube (tube 1), followed by vortexing and spinning. The library volume can be varied depending on the desired DNA-to-bead ratio of 3:1, 2:1, 1:1, 1:1.7, 1:3, 1:5, 1:10. For example, the DNA-to-bead ratio can be 1:1 to 1:1.5.

The rehydrated recombinase mix (tube 2, reconstituted in 180 µL rehydration buffer to a volume of approximately 185 µL) is added to the bead tube (tube 1), followed by vortexing and spinning.

Various amount of RNase H (at 20× concentrate from original NEB product) is added to the reaction tube, followed by vortexing and spinning. The volume is filled to 225 µL with low-TE.

75 µL of iced 28 mM Mg-acetate in sieving agent is added to the bead tube, followed by vortexing and spinning, and put back on ice for 10 seconds, and incubated at 37° C. for 30-60 minutes on the heat block.

The reaction is stopped by adding 50 µL 500 mM EDTA, and 100 µL 1% SDS. The reaction tube is then topped off to 1 mL with TE buffer, followed by vortexing and spinning.

The beads are enriched by binding the biotinylated poly-nucleotides with paramagnetic beads conjugated with streptavidin (MyOne™ Bead from Dynabeads).

The enriched beads are loaded into an ION TORRENT ion-sensitive chip and a standard sequencing reaction is conducted.

Figure 12C:
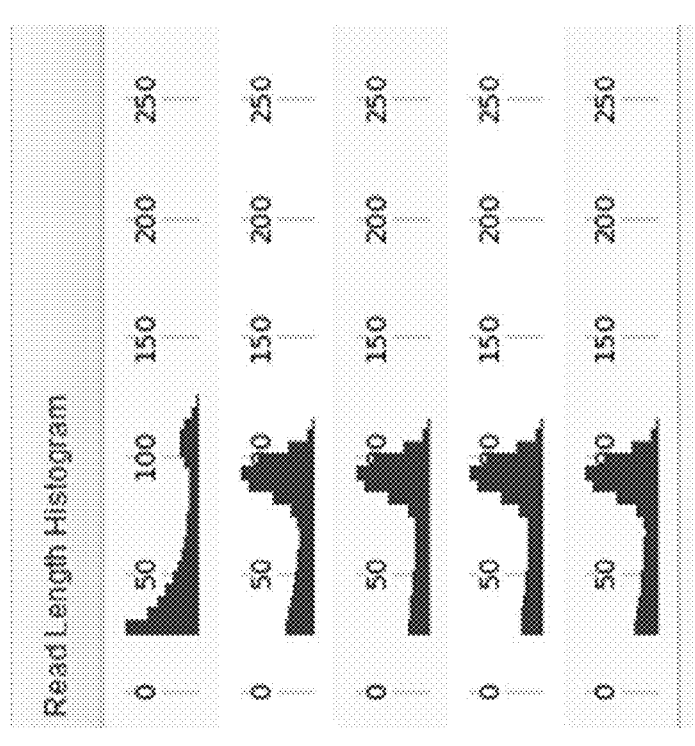
FIG. 12C is a read length histogram for sequencing results using the reaction volumes and times of FIG. 12A.

The experiment disclosed above in this Example was performed using SEQ ID NO:6 attached to beads as the universal reverse 3' blocked primer, SEQ ID NO:9 as the universal non-blocked standard primer in solution and SEQ ID NO:13 as the biotinylated forward primer for bead enrichment. Barcoded template DNA libraries (100 bp insert library with a tailed-A (57 bp) and P1B (53 bp) adapters with an expected amplicon size of about 210 bp) (See FIG. 10) were used. Each of the barcoded libraries was amplified in individual reactions, for a total of four samples, using 2 to 4 uL of 20× RNase H enzyme, See FIG. 12A.

Following amplification, the beads from each barcoded library were combined and sequenced on the same ION TORRENT sequencing chip. The amplification of template was successful on beads immobilized with a 3' blocked primer from a reaction in a single continuous liquid phase. The RPA amplification methods using an immobilized 3' blocked primer of the invention and RNase H enzyme generated monoclonally amplified templates on beads from a template library, which were subsequently sequenced. The RNase H enzyme, which may be rate limiting for the amplification step, was analyzed by using two different volumes (2 µL and 4 µL) of the 20× enzyme (See FIG. 12A) for the impact downstream on the sequencing reaction. The estimated unit concentration of the 20× concentrate is about 100 U/µl; 2 µL of RNase H contains about 200 U of enzyme and 4 µL contains about 400 U of enzyme. The results indicated that more enzyme, as compared to half as much, resulted in better amplification of the template on the beads. See FIG. 12B, wherein the samples (2 and 4) with about 400 U of enzyme resulted in more "reads", i.e. more amplified template, as compared to samples 1 and 3 with half as much (200 U) RNase H enzyme. Moreover, virtually complete amplification was reached within 40 minutes. Little further gain was achieved with a longer 60 minute amplification reaction. See FIGS. 12A to 12C.

Example 6: Amplification of Template with an Abasic (Baseless) Cleavable Blocked Primer in a RPA Amplification Reaction This example illustrates clonal amplification of a DNA template using a recombinase polymerase amplification reaction wherein at least one of the primers of a primer pair is a 3' blocked primer, wherein the blocked primer contains an abasic cleavable moiety that is apurinic, apyrimidinic or a spacer. That cleavable moiety is hydrolyzed by an apurinic/apyrimidinic (AP) endonuclease when the blocked primer is hybridized to the DNA template forming a double stranded duplex. Accordingly, the blocked primers comprise a 5' domain, an abasic cleavable moiety (e.g. baseless), a 3' domain and a blocking moiety (i.e. the primer is not extendable by a polymerase).

Class I and II AP endonucleases create a nick in the phosphodiester backbone at the 5' side of the abasic site leaving a polymerase extendable 3'-OH on the remaining 5' domain of the primer for extension. Examples of AP endonucleases include endonuclease IV (commercially available from Thermo Fisher, Carlsbad, CA), APE 1 (commercially available from Thermo Fisher) and APE 2.

The blocked primers with a cleavable abasic site can be synthesized with an internal abasic furan (e.g., tetrahydrofuran) or spacer that replaces a nucleotide at the desired cleavage site. Alternatively, the primers containing an abasic site can be synthesized with a uracil base replacing a nucleotide at the desired cleavage site. Prior to use in the methods, that primer can be treated with Uracil-DNA Glycosylase (UDG) to convert the Uracil to an abasic site; UDG removes uracil residues from the sugar moiety of single- and double-stranded. DNA without destroying the phosphodiester backbone.

As a non-limiting example, the RPA method can be performed essentially using the methods described in Example 1 in a single reaction vessel in a single continuous liquid phase, wherein a blocked (non-extendable) primer containing an abasic cleavable moiety and a biotin blocking moiety with a V2 configuration is added in solution to the reaction mixture, wherein Endo IV or APE 1 are used as endonucleases replacing RNase H in Example 1. Amplification using the abasic cleavable blocked (non-extendable) primers with Endo IV or APE 1 was compared to amplification using ribobase cleavable blocked (non-extendable) primers of the invention with a V2 or V3 configuration and RNase H enzyme.

The abasic containing primers were synthesized with a uracil between the 5' domain and the 3' domain of the blocked primers. The blocked forward and reverse primer sequence were as follows, wherein the uracil is converted to an abasic site prior to use:

```
Forward AP-15D:
                                  (SEQ ID NO: 28)
GAA TCT GTC CAT AAG GTC AGT AAC GAT CCA UCT CAT CCC TGC GTG T-3'biotin Reverse AP-15D:
                                  (SEQ ID NO. 29)
CCT ATC CCC TGT GTG CCT TGG CAG TCT CAG CCU CTC TAT GGG CAG TCG-3'biotin
```

The ribobase containing blocked primes used in a control RPA reaction with RNase HII enzyme were selected from the primer pairs of SEQ ID NO. 18 and SEQ ID NO. 19; SEQ ID NO. 20 and SEQ ID NO. 21; and SEQ ID NO. 23 and SEQ ID NO. 24. See FIG. 10.

Prior to use in the RPA methods, the internal uracil of SEQ ID NO. 28 and 29 was converted to an abasic site by treatment with UDG. 0.2 uL of each uracil-containing blocked primer (100 uM stock), 0.4 uL UDG (1 U/uL, Thermo Fisher Scientific), and 1.2 uL RPA rehydration buffer (same formulation as described for RPA reaction), were combined for a total of 2 uL mixture. The mixture was incubated at 37° C. in a thermocycler for 15 min for conversion to AP-containing primers. The 2 uL treated primer mixture was then added to RPA reaction (50 uL reaction) as the primer mix, so that each primer was 400 nM in the RPA reaction. The primer mix volume can be adjusted for other desired primer concentrations.

Hence, the RPA method was performed using SEQ ID NO. 28 and 29, containing an abasic site at the internal uracil, and the AP endonuclease endo IV (sourced from NEB and Thermo Fisher) or APE 1 (NEB). Template DNA libraries with an expected amplicon size of about 123 bp were used starting with 1 pM of template. Each of the libraries was amplified in individual reactions, for a total of four samples, using 4 µL of commercial concentrations of Endo IV from NEB and Thermo Fisher and 2 µL, or 5 µL of 10× Endo IV (Thermo Fisher). See FIG. 13. The RPA reaction mixture was incubated for 17 hours at 37° C.

The amplification of template was successful with a blocked primer containing an abasic site from a reaction in a single continuous liquid phase when using 10× Endo IV. However, nonspecific products were also present, along with the template. The RPA amplification method using a primer with an abasic residue and endonuclease IV cleavage, could be optimized to reduce or eliminate the nonspecific products. Amplification of template was not successful when using Endo IV at the concentration provided by the commercial vendor. Not to be limited by theory, the results indicate the Endo IV enzyme, similar to RNase H, may be rate limiting for the amplification step, wherein more enzyme, i.e., 10×, resulted in better amplification of the template. In some embodiments, Endo IV is a viable endonuclease when paired with abasic 3' blocked primers for use in the RPA methods for amplification of template DNA.

The RPA method was also performed using SEQ ID NO. 28 and 29, containing an abasic site at the internal uracil, and the AP endonuclease APE 1 (NEB) as compared to use of ribobase blocked primers (SEQ ID NO. 18 and 19) and RNase H enzyme (NEB). Template DNA libraries with an expected amplicon size of about 123 bp were used starting with 1 pM of template. Each of the libraries was amplified in individual reactions, for a total of 10 samples, using 40 U of APE 1, 20 U or 45 U of RNase 100 nm to 800 nm each of SEQ ID NO 18 and 19 for the RNase H containing reaction mixture and 100 nm or 400 nm of SEQ ID NO. 28 and 29 for the APE 1 containing reaction mixture. See FIG. 14. The RPA reaction mixture was incubated for 30 minutes at 37° C.

Amplification of the template was successful for all ten amplification reactions including the reactions with the abasic cleavable blocked primers and APE 1 enzyme. No non-specific amplification product was observed, including primer dimers. See FIG. 14. In some embodiments, APE 1 is a viable endonuclease when paired with abasic blocked primers of the invention for use in the RPA methods for amplification of template DNA.

A third experiment was conducted using RNase HII enzyme as a control with the primer pairs SEQ ID NO. 18 and 19; SEQ ID NO. 20 and 21 and SEQ ID NO. 22 and 23 (See FIG. 10) as compared with the use of Endo IV or APE 1 enzyme and primer pair SEQ ID NO. 28 and 29, with and without the internal uracil converted to a cleavable abasic moiety. The product from the above RPA reaction was obtained using 1 pM of template, as above, 100 nm each of blocked primers, 20 U of RNase HII, 200 U or 50 U of Endo IV and 40 U of APE 1, wherein a portion of the 500_, purified RPA reaction product was loaded into wells of the agarose gels and the DNA fragments separated by electrophoresis. See FIG. 15. The RPA reaction mixture was incubated for 2 hours at 37° C.

The results indicate both Endo IV (when used at a 200 U concentration) and APE 1 are viable endonucleases, when paired with abasic blocked primers of the invention, for the amplification of DNA template in a RPA amplification reaction. Non-specific product was observed with the use of Endo IV, see FIG. 15 at lane 6 of gel, but exonuclease activities of the enzyme or contamination of the commercial enzyme may be the source of the non-specific amplification. Accordingly, In some embodiments, provided herein, is a reaction amplification method, such as RPA, performed using abasic cleavable blocked primers and the endonuclease APE 1 or Endo IV for cleavage at the abasic site of the blocked primer. Following cleavage of the primer at the abasic site by either Endo IV or APE 1, the 3' end of the 5' domain is extended and amplification of the template results as disclosed herein for an RPA amplification reaction.

---

What is claimed is:

1. A method for amplifying a nucleic acid template, comprising:

a) forming a reaction mixture by combining a nucleic acid template having a forward primer binding sequence and a reverse primer binding sequence, a polymerase, a recombinase, a single-stranded binding protein, a recombinase loading protein, a forward primer that is not extendable by the polymerase, a reverse primer that is not extendable by the polymerase, and an RNase H enzyme comprising a divalent cation, wherein the forward primer binding sequence is complementary or identical to at least a portion of the forward primer and the reverse primer binding sequence is complementary or identical to at least a portion of the reverse primer, and wherein the forward primer and the reverse primer comprise a 5' domain and a 3' domain separated by a nucleotide comprising one or more nucleotides that are cleavable by the RNase H enzyme, wherein the 5' domain is 10 to 40 nucleotides in length and the 3' domain is 10 to 25 nucleotides in length; and b) incubating the reaction mixture under substantially isothermal amplification conditions between 35° C. and 45° C. for 15 minutes to 60 minutes, thereby amplifying the nucleic acid template.

2. The method of claim 1, wherein the nucleic acid template is a member of a nucleic acid library comprising a population of nucleic acid templates each comprising a forward primer binding sequence, and wherein the forward primer is a universal forward primer that binds the universal forward primer binding sequence.

3. The method of claim 2, wherein the nucleic acid templates each comprise a universal reverse primer binding sequence and wherein the reverse primer is a universal reverse primer that binds the universal reverse primer binding sequence.

4. The method of claim 1, wherein either or both of the forward primer and the reverse primer are immobilized on a solid support.

5. The method of claim 4, wherein the solid support is a bead.

6. The method of claim 1, wherein the 5' domain is 15 to 30 nucleotides in length.

7. The method of claim 1, wherein the 3' domain is 14 to 25 nucleotides in length.

8. The method of claim 1, wherein the 3' domain is 15 to 25 nucleotides in length.

9. The method of claim 8, wherein a 3' nucleotide of the 3' domain of the forward primer is mismatched to the forward primer binding sequence.

10. The method of claim 1, wherein the RNase H enzyme is *E. coli* RNase HII.

11. The method of claim 1, wherein the reaction mixture comprises uvsY.

12. The method of claim 1, wherein the recombinase is selected from the group consisting of uvsX, RecA, RadA, RadB, Rad51, a homologue thereof, a functional analog thereof and a combination thereof.

13. The method of claim 1, wherein the reaction mixture comprises uvsY accessory protein and uvsX recombinase.

14. The method of claim 1, wherein the amplifying is from 15 to 45 minutes.

15. The method of claim 1, wherein the RNase H enzyme is RNase HII and the incubating temperature is between 35° C. and 40° C.

16. The method of claim 1, wherein RNase Henzyme is present at a concentration from 5 U to 200 U/50 μL.

17. The method of claim 1, wherein the RNase H enzyme is present at a concentration from 10 to 90 U/50 μL.

18. The method of claim 1, wherein the reaction mixture comprises magnesium or manganese ions.

19. The method of claim 1, wherein the one or more nucleotides that are cleavable by the RNase H Enzyme is rU, rG or rA.

20. The method of claim 1, wherein the 3' domain of the non-extendable primers is 14 to 20 nucleotides in length and the one or more nucleotides that are cleavable by the RNase H enzyme is rU, rG or rA.

21. The method of claim 1, wherein the polymerase is Sau polymerase, T7 polymerase with reduced 3' to 5' exonuclease activity, Bsu polymerase, or a combination thereof.

* * * * *

SEQUENCE LISTING

```
<160> NUMBER OF SEQ ID NOS: 29

<210> SEQ ID NO 1
<211> LENGTH: 202
<212> TYPE: DNA
<213> ORGANISM: Artificial Sequence
<220> FEATURE:
<223> OTHER INFORMATION: Synthetic DNA

<400> SEQUENCE: 1
acacggtcca gactcctacg ggaggcagca gtggggaata ttgcacaatg ggcgcaagcc      60
tgatgcagcc atgccgcgtg tatgaagaag gccttcgggt tgtaaagtac tttcagcggg     120
gaggaaggga gtaaagttaa tacctttgct cattgacgtt acccgcagaa gaagcaccgg     180
ctaactccgt gccagcagcc gc                                              202

<210> SEQ ID NO 2
<211> LENGTH: 30
<212> TYPE: DNA
<213> ORGANISM: Artificial Sequence
<220> FEATURE:
<223> OTHER INFORMATION: Synthetic DNA

<400> SEQUENCE: 2
acacggtcca dactcctacg ggaggcagca                                       30

<210> SEQ ID NO 3
<211> LENGTH: 30
<212> TYPE: DNA
<213> ORGANISM: Artificial Sequence
<220> FEATURE:
<223> OTHER INFORMATION: Synthetic DNA

<400> SEQUENCE: 3
gcggctgctg gcacggagtt agccggtgct                                       30

<210> SEQ ID NO 4
<211> LENGTH: 47
<212> TYPE: DNA
<213> ORGANISM: Artificial Sequence
<220> FEATURE:
<223> OTHER INFORMATION: Synthetic DNA

<400> SEQUENCE: 4
acacggtcca dactcctacg ggaggcagca rgtggggaat attgcac                    47

<210> SEQ ID NO 5
<211> LENGTH: 47
<212> TYPE: DNA
<213> ORGANISM: Artificial Sequence
<220> FEATURE:
<223> OTHER INFORMATION: Synthetic DNA

<400> SEQUENCE: 5
gcggctgctg gcacggagtt agccggtgct ructtctgcg ggtaacg                    47
```

<210> SEQ ID NO 6
<211> LENGTH: 50
<212> TYPE: DNA
<213> ORGANISM: Artificial Sequence
<220> FEATURE:
<223> OTHER INFORMATION: Synthetic DNA

<400> SEQUENCE: 6 cctatccoct gtgtgccttg gcagtctcag ccructctat gggcagtcga                50

<210> SEQ ID NO 7
<211> LENGTH: 34
<212> TYPE: DNA
<213> ORGANISM: Artificial Sequence
<220> FEATURE:
<223> OTHER INFORMATION: Synthetic DNA

<400> SEQUENCE: 7
ccactacgcc tccgcttruc ctctctatgg gcag                                 34

<210> SEQ ID NO 8
<211> LENGTH: 34
<212> TYPE: DNA
<213> ORGANISM: Artificial Sequence
<220> FEATURE:
<223> OTHER INFORMATION: Synthetic DNA

<400> SEQUENCE: 8
cctccgcttt cctctctrat gggcagtcgg tgat                                 34

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA

<400> SEQUENCE: 9
ccatctcatc cctgcgtgtc                                                 20

<210> SEQ ID NO 10
<211> LENGTH: 26
<212> TYPE: DNA
<213> ORGANISM: Artificial Sequence
<220> FEATURE:
<223> OTHER INFORMATION: Synthetic DNA

<400> SEQUENCE: 10
ccatctcatc cctgcgtgtc tccgac                                          26

<210> SEQ ID NO 11
<211> LENGTH: 31
<212> TYPE: DNA
<213> ORGANISM: Artificial Sequence
<220> FEATURE:
<223> OTHER INFORMATION: Synthetic DNA

<400> SEQUENCE: 11
ccatctcatc cctgcrgtgt ctccgactca g                                    31

<210> SEQ ID NO 12
<211> LENGTH: 37
<212> TYPE: DNA
<213> ORGANISM: Artificial Sequence
<220> FEATURE:

-continued

<223> OTHER INFORMATION: Synthetic DNA

<400> SEQUENCE: 12
aacgatccat ctcatccctg crgtgtctcc gactcag                             37

<210> SEQ ID NO 13
<211> LENGTH: 20
<212> TYPE: DNA
<213> ORGANISM: Artificial Sequence
<220> FEATURE:
<223> OTHER INFORMATION: Synthetic DNA

<400> SEQUENCE: 13
ccatctcatc cctgcgtgtc                                                20

<210> SEQ ID NO 14
<211> LENGTH: 57
<212> TYPE: DNA
<213> ORGANISM: Artificial Sequence
<220> FEATURE:
<223> OTHER INFORMATION: Synthetic DNA

<400> SEQUENCE: 14
gaatctgtcc ataaggtcag taacgatcca tctcatccct gcgtgtctcc gactcag      57

<210> SEQ ID NO 15
<211> LENGTH: 53
<212> TYPE: DNA
<213> ORGANISM: Artificial Sequence
<220> FEATURE:
<223> OTHER INFORMATION: Synthetic DNA

<400> SEQUENCE: 15
cctatcccct gtgtgccttg gcagtctcag cctctctatg ggcagtcggt gat          53

<210> SEQ ID NO 16
<211> LENGTH: 31
<212> TYPE: DNA
<213> ORGANISM: Artificial Sequence
<220> FEATURE:
<223> OTHER INFORMATION: Synthetic DNA

<400> SEQUENCE: 16
ccatctcatc cctgcgtgtc tccgractca c                                  31

<210> SEQ ID NO 17
<211> LENGTH: 31
<212> TYPE: DNA
<213> ORGANISM: Artificial Sequence
<220> FEATURE:
<223> OTHER INFORMATION: Synthetic DNA

<400> SEQUENCE: 17
cctatcccct gtgtgccttg gcargtctca c                                  31

<210> SEQ ID NO 18
<211> LENGTH: 49
<212> TYPE: DNA
<213> ORGANISM: Artificial Sequence
<220> FEATURE:
<223> OTHER INFORMATION: Synthetic DNA

<400> SEQUENCE: 18
gaatctgtcc ataaggtcag taacgatcca trctcatccc tgcgtgtca              49

<210> SEQ ID NO 19
<211> LENGTH: 54
<212> TYPE: DNA
<213> ORGANISM: Artificial Sequence
<220> FEATURE:
<223> OTHER INFORMATION: Synthetic DNA

<400> SEQUENCE: 19
cctatcccct gtgtgccttg gcagtctcag cctctrctat gggcagtcgg tgaa          54

<210> SEQ ID NO 20
<211> LENGTH: 48
<212> TYPE: DNA
<213> ORGANISM: Artificial Sequence
<220> FEATURE:
<223> OTHER INFORMATION: Synthetic DNA

<400> SEQUENCE: 20
gaatctgtcc ataaggtcag taacgatcca trctcatccc tgcgtgtc              48

<210> SEQ ID NO 21
<211> LENGTH: 52
<212> TYPE: DNA
<213> ORGANISM: Artificial Sequence
<220> FEATURE:
<223> OTHER INFORMATION: Synthetic DNA

<400> SEQUENCE: 21
cctatcccct gtgtgccttg gcagtctcag cctctrctat gggcagtcgg tg            52

<210> SEQ ID NO 22
<211> LENGTH: 47
<212> TYPE: DNA
<213> ORGANISM: Artificial Sequence
<220> FEATURE:
<223> OTHER INFORMATION: Synthetic DNA

<400> SEQUENCE: 22
gaatctgtcc ataaggtcag taacgatcca ructcatccc tgcgtgt              47

<210> SEQ ID NO 23
<211> LENGTH: 38
<212> TYPE: DNA
<213> ORGANISM: Artificial Sequence
<220> FEATURE:
<223> OTHER INFORMATION: Synthetic DNA

<400> SEQUENCE: 23
gaatctgtcc ataaggtcag taacgatcca trctcatc                38

<210> SEQ ID NO 24
<211> LENGTH: 42
<212> TYPE: DNA
<213> ORGANISM: Artificial Sequence
<220> FEATURE:
<223> OTHER INFORMATION: Synthetic DNA

<400> SEQUENCE: 24
cctatcccct gtgtgccttg gcagtctcag cctctrctat gg              42

<210> SEQ ID NO 25
<211> LENGTH: 42
<212> TYPE: DNA
<213> ORGANISM: Artificial Sequence
<220> FEATURE:
<223> OTHER INFORMATION: Synthetic DNA -continued

```
<400> SEQUENCE: 25
gaatctgtcc ataaggtcag taacgatcca ructcatccc tg                              42

<210> SEQ ID NO 26
<211> LENGTH: 32
<212> TYPE: DNA
<213> ORGANISM: Artificial Sequence
<220> FEATURE:
<223> OTHER INFORMATION: Synthetic DNA

<400> SEQUENCE: 26
gaatctgtcc ataagrgtca gtaacgatcc at                                         32

<210> SEQ ID NO 27
<211> LENGTH: 34
<212> TYPE: DNA
<213> ORGANISM: Artificial Sequence
<220> FEATURE:
<223> OTHER INFORMATION: Synthetic DNA

<400> SEQUENCE: 27
cctatcccct gtgtgccrut ggcagtctca gcct                                       34

<210> SEQ ID NO 28
<211> LENGTH: 46
<212> TYPE: DNA
<213> ORGANISM: Artificial Sequence
<220> FEATURE:
<223> OTHER INFORMATION: Synthetic DNA

<400> SEQUENCE: 28
gaatctgtcc ataaggtcag taacgatcca uctcatccct gcgtgt                          46

<210> SEQ ID NO 29
<211> LENGTH: 48
<212> TYPE: DNA
<213> ORGANISM: Artificial Sequence
<220> FEATURE:
<223> OTHER INFORMATION: Synthetic DNA

<400> SEQUENCE: 29
cctatcccct gtgtgccttg gcagtctcag ccuctctatg ggcagtcg                        48
```